United States Patent
Kipps et al.

(10) Patent No.: US 10,913,798 B2
(45) Date of Patent: Feb. 9, 2021

(54) MODULATORS OF ROR1-ROR2 BINDING

(71) Applicant: The Regents of the University of California, Oakland, CA (US)

(72) Inventors: Thomas J. Kipps, San Diego, CA (US); Jian Yu, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 158 days.

(21) Appl. No.: 15/568,737

(22) PCT Filed: Apr. 25, 2016

(86) PCT No.: PCT/US2016/029250
§ 371 (c)(1),
(2) Date: Oct. 23, 2017

(87) PCT Pub. No.: WO2016/172726
PCT Pub. Date: Oct. 27, 2016

(65) Prior Publication Data
US 2018/0112002 A1 Apr. 26, 2018

Related U.S. Application Data

(60) Provisional application No. 62/152,424, filed on Apr. 24, 2015.

(51) Int. Cl.
| | | |
|---|---|---|
| G01N 33/68 | (2006.01) | |
| G01N 33/53 | (2006.01) | |
| G01N 33/58 | (2006.01) | |
| C07K 16/28 | (2006.01) | |
| C07K 16/22 | (2006.01) | |
| A61K 39/00 | (2006.01) | |

(52) U.S. Cl.
CPC .......... *C07K 16/2857* (2013.01); *C07K 16/22* (2013.01); *C07K 16/2803* (2013.01); *A61K 2039/505* (2013.01); *C07K 2317/24* (2013.01); *C07K 2317/73* (2013.01); *C07K 2317/92* (2013.01); *C07K 2317/94* (2013.01); *G01N 33/53* (2013.01); *G01N 33/6845* (2013.01); *G01N 2500/02* (2013.01)

(58) Field of Classification Search
CPC .............. G01N 33/53; G01N 2500/00; G01N 2500/02; G01N 33/6845
See application file for complete search history.

(56) References Cited

U.S. PATENT DOCUMENTS

| | | | | |
|---|---|---|---|---|
| 2002/0155121 A1* | 10/2002 | Devico | ................ | C07K 14/005 424/186.1 |
| 2013/0289121 A1 | 10/2013 | Torres et al. | | |

FOREIGN PATENT DOCUMENTS

| | | |
|---|---|---|
| EP | 2 659 910 A1 | 11/2013 |
| EP | 2 659 910 B1 | 11/2013 |
| WO | WO-2014/031174 A1 | 2/2014 |

OTHER PUBLICATIONS

Paganoni et al, (Neuroscience 2010, 165(4): 1261, pp. 1-27.*
Cook et al., Oncogene, 2014, 33:4021-4035.*
Zhang et al., The American Journal of Pathology, 2012, 181(6): 1903-1910.*
Anastas, J.N. et al. (Jan. 2013). "WNT signalling pathways as therapeutic targets in cancer," Nat Rev Cancer 13(1):11-26.
Baskar, S. et al. (Jan. 15, 2008). "Unique cell surface expression of receptor tyrosine kinase ROR1 in human B-cell chronic lymphocytic leukemia," Clin Cancer Res 1492):396-404.
Bos, J.L. et al. (Jun. 1, 2007). "GEFs and GAPs: critical elements in the control of small G proteins," Cell 129(5):865-877.
Broome, H.E. et al. (Oct. 2011, e-published Aug. 2, 2011). "ROR1 is expressed on hematogones (non-neoplastic human B-lymphocyte precursors) and a minority of precursor-B acute lymphoblastic leukemia," Leuk Res 35(10):1390-1394.
Cierpicki, T. et al. (Jan. 2015). "Targeting protein-protein interactions in hematologic malignancies: still a challenge or a great opportunity for future therapies?" Immunol Rev 263(1):279-301.
Cui, B. et al. (Jun. 15, 2013). "Targeting ROR1 inhibits epithelial-mesenchymal transition and metastasis," Cancer Res 73(12):3649-3660.
Daneshmanesh, A.H. et al. (Sep. 1, 2008). "Ror1, a cell surface receptor tyrosine kinase is expressed in chronic lymphocytic leukemia and may serve as a putative target for therapy," Int J Cancer 123(5):1190-1195.
Extended European Search Report dated Aug. 8, 2018, for EP Patent Application No. 16784106.3, 11 pages.
Fukuda, T. et al. (Feb. 2008, e-published Feb. 19, 2008). "Antisera induced by infusions of autologous Ad-CD154-leukemia B cells identify ROR1 as an oncofetal antigen and receptor for Wnt5a," PNAS USA 105(8):3047-3052.
Gentile, A. et al. (Apr. 15, 2011, e-published Apr. 12, 2011). "Ror1 is a pseudokinase that is crucial for Met-driven tumorigenesis," Cancer Res 71(8):3132-3141.
Henry, C. et al. (Nov. 24, 2015). "Targeting the ROR1 and ROR2 receptors in epithelial ovarian cancer inhibits cell migration and invasion," Oncotarget 6(37):40310-40326.
International Search Report dated Nov. 15, 2016, for PCT Application No. PCT/US2016/029250, filed Apr. 25, 2016, 5 pages.
Katoh, M. et al. (Nov. 2005). "Comparative genomics on ROR1 and ROR2 orthologs," Onco Rep 14(5):1381-1384.
Niehrs, C. (Dec. 2012, e-published Nov. 15, 2012). "The complex world of WNT receptor signalling," Nat Rev Mol Cell Biol 13(12):767-779.

(Continued)

*Primary Examiner* — Hong Sang
(74) *Attorney, Agent, or Firm* — Mintz, Levin, Cohn, Ferris, Glovsky and Popeo, P.C.

(57) ABSTRACT

Provided herein are, inter alia, methods of identifying agents that are capable inhibiting the binding (e.g., coupling) between a ROR1 protein and a ROR2 protein. By interfering with ROR1-ROR2 coupling (binding) the agents identified using the methods provided herein inhibit non-canonical Wnt5a signaling. Thus, the agents identified by the methods provided herein may, inter alia, be useful for cancer diagnosis and therapy.

14 Claims, 35 Drawing Sheets

Specification includes a Sequence Listing.

(56) References Cited

OTHER PUBLICATIONS

Oishi, I. et al. (Jan. 1999). "Spatio-temporally regulated expression of receptor tyrosine kinases, mRor1, mRor2, during mouse development: implications in development and function of the nervous system," *Genes Cell* 4(1):41-56.
Paganoni, S. et al. (Feb. 17, 2010, e-published Dec. 1, 2009). "Ror1-Ror2 complexes modulate synapse formation in hippocampal neurons," *Neuroscience* 165(4):1261-1274.
Rebagay, G. et al. (Apr. 18, 2012). "ROR1 and ROR2 in Human Malignancies: Potentials for Targeted Therapy," *Front Oncol* 2:34.
Toledo, E.M. et al. (Nov. 2008, e-published Aug. 19, 2008). "Wnt signaling in neuroprotection and stem cell differentiation," *Prog Neurobiol* 86(3):281-296.
Written Opinion dated Nov. 15, 2016, for PCT Application No. PCT/US2016/029250, filed Apr. 25, 2016, 7 pages.
Yamaguchi, T. et al. (Mar. 20, 2012). "NKX2-1/TITF1/TTF-1-Induced ROR1 is required to sustain EGFR survival signaling in lung adenocarcinoma," Cancer Cell 21(3):348-361.
Yu, J. et al. (Feb. 2016). "Wnt5a induces ROR1/ROR2 heterooligomerization to enhance leukemia chemotaxis and proliferation," *J Clin Invest* 126(2):585-598.
Zhang, S. et al. (Dec. 2012, e-published Oct. 4, 2012). "The onco-embryonic antigen ROR1 is expressed by a variety of human cancers," *Am, J Pathol* 181(6):1903-1910.
Zhang, S. et al. (Dec. 2, 2014, e-published Nov. 19, 2014). "Ovarian cancer stem cells express ROR1, which can be targeted for anti-cancer-stem-cell therapy," *PNAS USA* 111(48):17266-17271.

\* cited by examiner

FIG. 12A - cont.
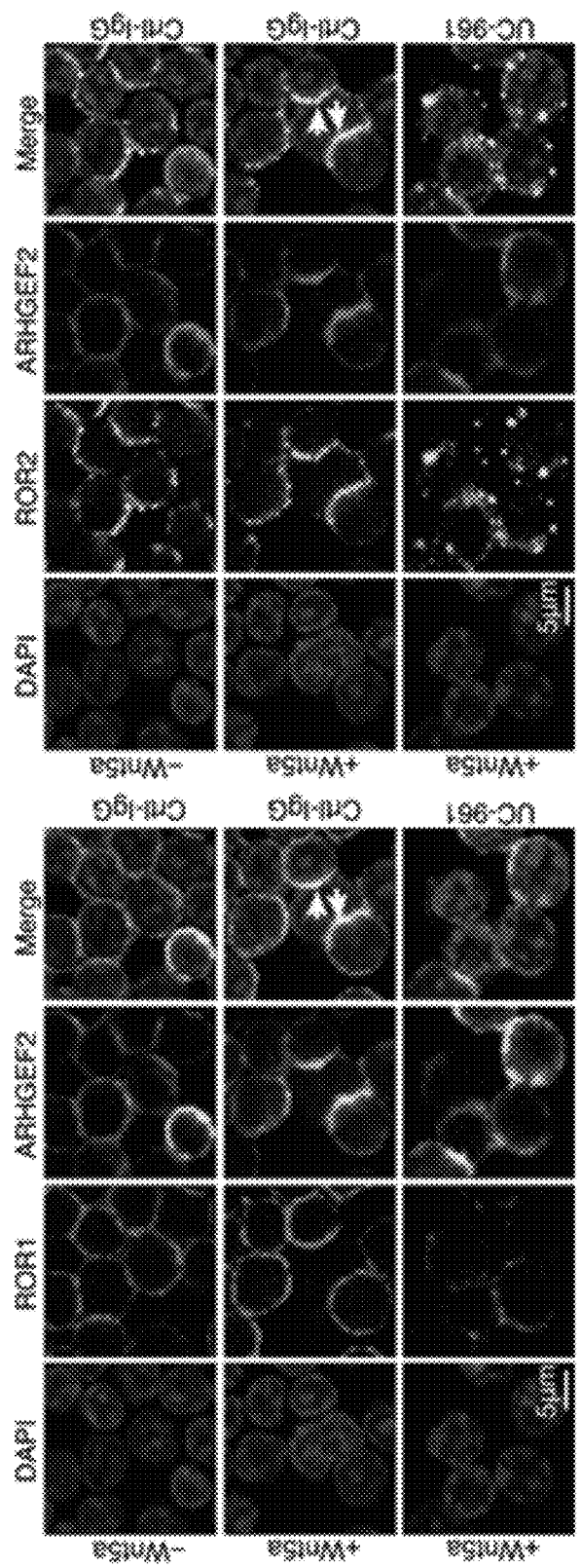

FIG. 12A - cont.
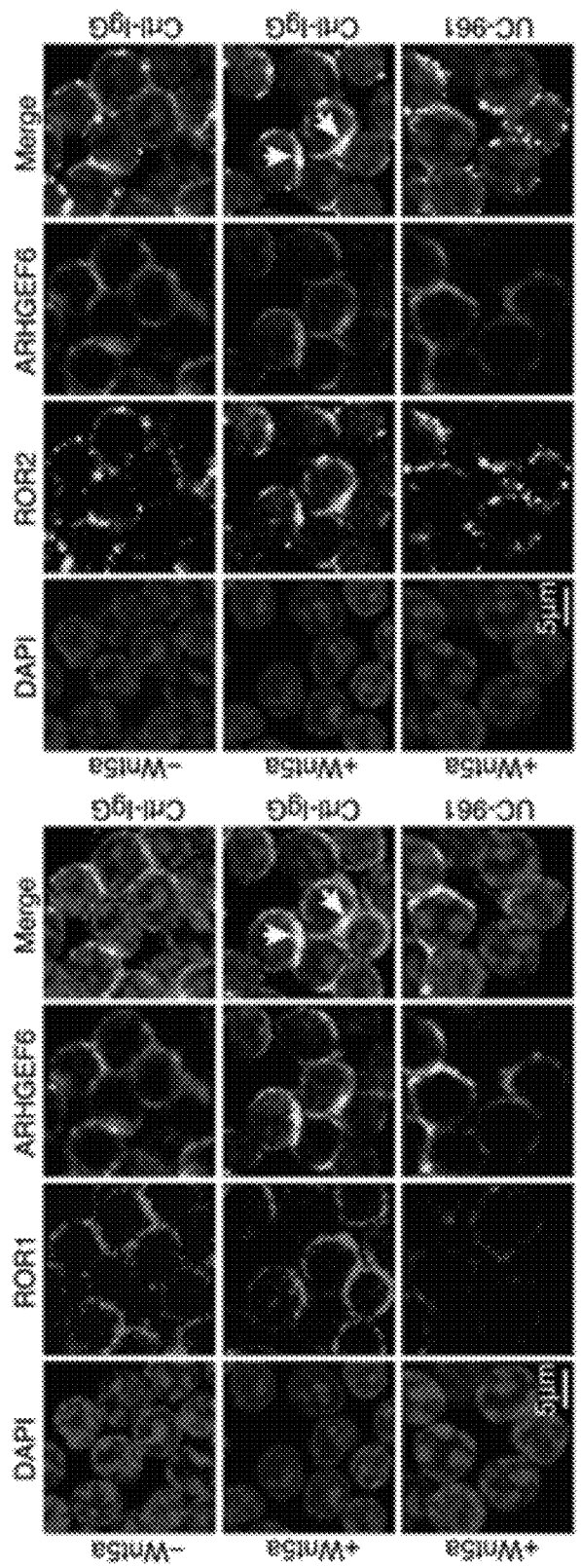

MODULATORS OF ROR1-ROR2 BINDING

CROSS-REFERENCES TO RELATED APPLICATIONS

This application is a national stage entry under 35 U.S.C. 371 of international application no. PCT/US2016/029250 filed Apr. 25, 2016, which claims priority to, and the benefit of, U.S. provisional application 62/152,424, filed Apr. 24, 2015, the disclosure of which is incorporated by reference in its entirety.

REFERENCE TO A "SEQUENCE LISTING," A TABLE, OR A COMPUTER PROGRAM LISTING APPENDIX SUBMITTED ON A COMPACT DISK

The Sequence Listing written in file 048537-558N01US_ST25.TXT, created Feb. 18, 2020, 93,810 bytes, machine format IBM-PC, MS-Windows operating system, is hereby incorporated by reference.

BACKGROUND OF THE INVENTION

The Receptor-tyrosine kinase-like Orphan Receptors, ROR1 and ROR2, are evolutionarily conserved type I proteins[1-8]. Studies on the developmental expression patterns of these proteins in *Caenorhabditis elegans, Drosophila melanogaster, Xenopus laevis*, and *Mus musculus* have shown striking conservation[9]. ROR1 and ROR2 are expressed at highest levels during the early stages of embryogenesis, being represented in most of the major systems in tissues derived from all three germ layers, but most prominently the neural crest, whereas expression of ROR1 appears more restricted to the neural mesenchyme [10,11]. Complete knockout of either ROR1 or ROR2, however, results in pervasive developmental abnormalities involving also the heart, lungs, urogenital tracts, and other organs, suggesting that each potentially contributes broadly to organogenesis [12,13].

Although low-levels of ROR2 can be found on some adult tissues, post-partum expression of ROR1 is not apparent, except on a small subset of precursor B-cells called hematogones [14]. However, ROR1 can be found on the leukemia cells of patients with chronic lymphocytic leukemia (CLL) [15-17], and ROR1 or ROR2 is expressed by neoplastic cells of a variety of different cancers [18,19]. Cancer-cell expression of ROR1 or ROR2 has been associated with enhanced cancer-cell migration, the epithelial-mesenchymal transition (EMT), increased associated-risk for relapsed disease and metastasis, and unfavorable prognosis [20,21]. More recently, ROR1 was identified on ovarian cancer-stem-cells, which have enhanced capacity for migration/spheroid formation in vitro and engraftment/metastasis in vivo [22].

ROR1 and ROR2 each may function as a receptor for Wnt5a [15,23], which may induce non-canonical Wnt signaling, potentially leading to enhanced tumor-cell growth, directional migration, and/or tissue-cell polarity during organogenesis [18,24-26]. On the other hand, ROR2 also can repress transcription of Wnt-target genes and modulate Wnt signaling by sequestering canonical Wnt ligands, thereby serving as a tumor suppressor in different cell contexts [27]. Although the activity of ROR1 or ROR2 is thought to be influenced by associated proteins [28,29], ROR1 and ROR2 are considered to function independently from one another.

There is a need in the art for effective modulators of the molecular pathways associated with ROR1, ROR2 and/or Wnt 5a. There is also a need in the art for anticancer therapeutics. Provided herein are solutions to these and other needs in the art.

BRIEF SUMMARY OF THE INVENTION

In one aspect, a method of identifying an inhibitor of ROR1-ROR2 binding is provided. The method includes (i) combining a test agent with a ROR1 protein and a ROR2 protein in a reaction vessel. (ii) A decrease in binding of the ROR1 protein to the ROR2 protein relative to a standard control is detected and thereby an inhibitor of ROR1-ROR2 binding is identified.

In one aspect, an antibody identified by the method provided herein including embodiments thereof is provided.

In another aspect, a method of inhibiting a ROR1-ROR2 interaction is provided. The method includes (i) contacting a compound identified by the method provided herein including embodiments thereof with a ROR1-ROR2 complex, wherein the complex includes a ROR1 protein and a ROR2 protein. (ii) The compound is allowed to inhibit the interaction between the ROR1 protein and the ROR2 protein, thereby inhibiting a ROR1-ROR2 interaction.

In another aspect, a method of treating cancer in a subject in need thereof is provided. The method includes administering to a subject a therapeutically effective amount of an antibody, small molecule, peptide or nucleic acid identified by a method provided herein including embodiments thereof.

In another aspect, a method of identifying an inhibitor of a protein complex including ROR1 and ROR2 proteins is provided. The method includes (i) combining a test agent in a reaction vessel including ROR1 and ROR2; and (ii) detecting a disruption of a protein complex including ROR1 and ROR2 relative to a standard control, thereby identifying an inhibitor of the protein complex including ROR1 and ROR2 proteins. In embodiments, the detecting includes detecting a decreased level of ROR1 and/or ROR2 in the protein complex in the presence of the test agent, wherein a decreased level of ROR1 and/or ROR2 in the complex relative to a standard control indicates the test agent is an inhibitor of a protein complex including ROR1 and ROR2 proteins. In embodiments, the detecting includes detecting an increased level of unbound ROR1 and/or unbound ROR2 in the protein complex in the presence of the test agent, wherein an increased level of unbound ROR1 and/or ROR2 relative to a standard control indicates the test agent is an inhibitor of a protein complex including ROR1 and ROR2 proteins.

In embodiments, the ROR1 and/or the ROR2 proteins include a detectable moiety. In embodiments, the detecting includes detecting a level of a guanine exchange factor (GEF) in the presence of the test agent, wherein a decreased level of the GEF relative to a standard control indicates the test agent is an inhibitor of a protein complex having ROR1 and ROR2 proteins. In embodiments, the GEF is RhoA, Rac1, AHRGEF1, AHRGEF2 or AHRGEF6. In embodiments, the GEF includes a detectable moiety. In embodiments, the combining occurs in the presence of a Wnt5a protein. In embodiments, the reaction vessel is a column including a solid support.

In embodiments, the protein complex comprising ROR1 and ROR2 is present in the absence of a cell. In embodiments, the ROR1 and the ROR2 are present on the surface of a cell. In embodiments, the cell is a tumor cell. In embodiments, the tumor cell is a chronic lymphocytic leukemia (CLL) cell. In embodiments, the CLL cell is a MEC1 cell. In embodiments, the cell forms part of an in vitro cell culture. In embodiments, the cell forms part of an organism. In embodiments, the organism is a mammal. In embodiments, the organism is a mouse.

In embodiments, the test agent is an antibody, a small molecule, a peptide, a protein or a nucleic acid. In embodiments, the test agent is an antibody. In embodiments, the antibody is an anti-ROR1 antibody. In embodiments, the antibody is an anti-ROR2 antibody. In embodiments, the antibody binds to an ROR1 protein or an ROR2 protein. In embodiments, the antibody binds to a KNG domain. In embodiments, the antibody is a humanized antibody. In embodiments, the antibody is a chimeric antibody. In embodiments, the antibody is a scFv.

BRIEF DESCRIPTION OF THE DRAWINGS

FIG. 1A: CD154-induced proliferation of CFSE-labeled CLL cells (n=6) with or without exogenous Wnt5a and treated with Ctrl-IgG or UC-961, as indicated in the upper left of each histogram. The results of assays on one representative CLL sample are shown with the percent of cells having less fluorescence than un-stimulated cells indicated in the lower left of each histogram. FIG. 1B: The bars indicate the mean proportions of CLL cells with diminished CFSE fluorescence from each of 6 different patients for each culture condition indicated at the bottom. FIG. 1C: The bars indicate the mean proportions of CLL cells (n=6) migrating in response to CXCL12 and/or Wnt5a with Ctrl-IgG or UC-961. FIG. 1D: Activated Rac1 and RhoA were measured in CLL cells, which were cultured in serum-free media (serum starved) and then treated with Wnt5a for the times indicated above each lane. Whole-cell lysates also were examined via immunoblot analysis for total Rac1 or RhoA. FIG. 1E: Wnt5a-induced activation of Rac1 (top panels) or RhoA (bottom panels) in CLL cells treated with Ctrl-IgG or UC-961, as indicated on top of each set of blots. FIG. 1F: Activated Rac1 in serum-starved CLL cells treated with or without Wnt5a and/or CD154 for 30 min. FIG. 1G: Activated RhoA in serum-starved CLL cells treated with or without Wnt5a and/or CXCL12 for 30 min. FIG. 1H: Analysis of CD154-induced proliferation of CLL cells (n=6) with or without exogenous Wnt5a and treated with a Rac1 inhibitor (NSC-23766) or a RhoA inhibitor (Y-27632). The results of assays on CFSE-labeled CLL cells of one representative sample are presented as in panel FIGS. 1A and 1I. The mean proportions of CLL cells with diminished CSFE fluorescence for 6 patient samples treated as indicated in the upper left are presented as in panel b. FIG. 1J: The mean proportions of CLL cells (n=6) migrating in response to CXCL12 and/or Wnt5a, with or without NSC-23766 or Y-27632. Data are shown as mean±SEM; *P<0.05; P<0.01,*P<0.001. For each of the immunoblots, the number beneath each lane is the ratio of band densities for activated versus total GTPase normalized for untreated samples.

FIG. 2A: Immunoblot analysis for ROR1 or ROR2 in lysates of ZAP70$^{Neg}$/mu-IgVH (CLL-1-4) or ZAP70$^{+}$/um-IgVH (CLL-5-8) CLL cells, or peripheral blood mononuclear cells (PBMC) of healthy subjects. Purified recombinant extracellular ROR1 or ROR2 (ROR1-ex or ROR2-ex) were loaded onto separate lanes as specificity controls. FIG. 2B: Detection of ROR1 or ROR2 on CD5$^{+}$CD19$^{+}$ CLL cells by flow cytometry. FIG. 2C: PBMC of healthy donors were stained with anti-ROR2-Alexa-488, anti-CD19-PE, and anti-CD5-APC mAbs and analyzed by flow cytometry. The gating strategy is indicated in the center contour plot for each subgroup specified on the top of each histogram depicting the fluorescence of cells incubated with the anti-ROR2 mAb (shaded) versus an Alexa-488-conjugated Ctrl-IgG (open histograms). The ΔMFI for each of the CD19$^{+}$ cell-subsets are indicated in the top right. FIG. 2D: The ΔMFI for ROR2 of CLL samples (n=80) or each of the gated lymphocyte subsets in PBMC of healthy donors (n=15). FIG. 2E: Immunoblot analysis of anti-ROR1 or anti-ROR2 ip from lysates of freshly-isolated CLL cells detecting the association of ROR1 with ROR2. FIG. 2F: Immunoblot analysis of anti-ROR1 ip from lysates of CLL cells cultured in serum-free media and then treated without (−) or with (+) Wnt5a. FIG. 2G: Wnt5a levels were assessed via ELISA in the plasma of CLL patients (n=9) or aged-matched healthy control subjects (Normal, n=9). Data are shown as mean±SEM; *P<0.05; ***P<0.001.

FIG. 3A: Co-localization (arrow) of ROR1 and ROR2 detected by confocal microscopy in freshly isolated CLL cells+/−Ctrl-IgG or UC-961, as indicated on the right margin of each row (Scale bar: 2 μm). FIG. 3B: Confocal microscopy of serum-starved CLL cells stained for ROR1 and ROR2 after treatment with or without Wnt5a and Ctrl-IgG or UC-961, presented as in FIG. 3A. FIG. 3C: Mean proportions of cells migrating toward CXCL12 with or without Wnt5a for CLL cells (n=6) transfected with control siRNA (Ctrl-siRNA) or siRNA specific for ROR1 or ROR2. Data are shown as mean±SEM; *P<0.05; **P<0.01. FIG. 3D: Activated RhoA or Rac1 were measured by Rho-family protein activity pull-down assays on lysates of CLL cells transfected with Ctrl-siRNA or siRNA specific for ROR1 or ROR2 and cultured with or without Wnt5a. Whole-cell lysates also were examined via immunoblot for total RhoA or Rac1 (bottom row). The numbers below each lane are the densities of activated to total GTPase normalized for untreated samples, as in FIG. 1D.

FIG. 4A: Co-localization (arrow) of ARHGEF1 with ROR1 and ROR2 in CLL cells cultured without (−) or with (+) Wnt5a, as indicated on the left margin or each row (Scale bar: 5 μm). FIG. 4B: Co-localization of ARHGEF2 with ROR1-ROR2 in CLL cells cultured without (−) or with (+) Wnt5a, as in FIG. 4A. FIG. 4C: Co-localization of ARHGEF6 with ROR1-ROR2 in CLL cells cultured without (−) or with (+) Wnt5a, as in FIG. 4A. FIG. 4D: In vitro exchange over time (in minutes) of RhoA (top two rows of graphs) or Rac1 (bottom two row of graphs) of ip from lysates of CLL cells cultured with or without Wnt5a, using mAbs specific for ARHGEF1, ARHGEF2, or ARHGEF6, as indicated in the bottom right of each graph. The line depicts GTPase-activation observed using buffer alone. FIG. 4E. In vitro exchange assay on RhoA or Rac1 of ip from lysates of CLL cells cultured with UC-961 or Ctrl-IgG, using mAbs specific for ARHGEF1, ARHGEF2, or ARHGEF6, as indicated in the bottom of each graph. The line depicts GTPase-activation using buffer alone. FIG. 4F: Activation RhoA or Rac1 following treatment without (−) or with (+) Wnt5a of CLL cells transfected with Ctrl-siRNA or siRNA specific for ARHGEF1, ARHGEF2, or ARHGEF6. Whole-cell lysates also were examined via immunoblot analysis for total RhoA or Rac1. The numbers beneath each lane is the ratio of band densities for activated versus total GTPase normalized for untreated samples.

FIG. 5A: Schematic representation of the structure of ROR1 and truncated forms of ROR1 was shown. Interaction of ROR1 with ROR2 was confirmed by immunoblot analysis of anti-ROR1 ip using lysates from MEC1 (Ctrl.), MEC1-ROR1 (ROR1), or MEC1 cells transfected with truncated forms of ROR1. FIG. 5B: Co-localization (e.g., arrow) of ARHGEF1, ARHGEF2 or ARHGEF6 with ROR1 and ROR2 in MEC1-ROR1 cells (Scale bar: 2 μm). FIG. 5C: Activated Rac1 or RhoA were measured in MEC1 (Ctrl.), MEC1-ROR1 (ROR1), and MEC1 cells expressing truncated forms of ROR1. Whole-cell lysates also were examined via immunoblot for total Rac1 or RhoA. The numbers beneath each lane are the ratios of band densities for activated versus total GTPase normalized for MEC1 samples. FIG. 5D: Inhibition of Rac1- or RhoA-activation by UC-961 and anti-Wnt5a mAbs in MEC1 or MEC1-ROR1 cells. The numbers beneath each lane are the ratios of band densities normalized for MEC1, as in FIG. 5C. FIG. 5E: The mean numbers of MEC1 (circles), MEC1-ROR1 (squares), or MEC1 cells expressing each of the truncated forms of ROR1 (as indicated in the legend) in triplicate wells at the days indicated below the graph. FIG. 5F: The mean numbers of MEC1-ROR1 cells cultured with Ctrl-IgG (squares), UC-961 (triangles) or anti-Wnt5a (inverted triangles) in triplicate wells at the times indicated. FIG. 5G: The bars indicate the mean proportions of MEC1, MEC1-ROR1, or MEC1 cells transfected with each of the truncated forms of ROR1 (as indicated in the legend) migrating with (+) or without (−) CCL21, as indicated at the bottom. FIG. 5H: Bars depict the mean proportions of MEC1-ROR1 cells migrating with (+) or without (−) CCL21 in the presence of Ctrl-IgG, UC-961 or anti-Wnt5a. Data in FIGS. 5E-5H are shown as mean±SEM; *P<0.05; **P<0.01. FIG. 5I: Cartoon diagram modeling molecular mechanisms by which Wnt5a enhances proliferation and migration by inducing formation of a ROR1-ROR2 heterodimer, which recruits GEFs that activate Rac1 and RhoA.

FIG. 6A: Representative spleens of $Rag2^{-/-}\gamma_c^{-/-}$ mice 3 weeks after receiving an intravenous infusion of $1\times10^6$ MEC1 or MEC1-ROR1 cells. The spleen of an age-matched, non-engrafted $Rag2^{-/-}\gamma_c^{-/-}$ mouse (Nor) is shown for comparison. FIG. 6B: MEC1 or MEC1-ROR1 cells were collected from the marrow of the femur or tibia or from the spleens of mice engrafted 3-weeks earlier with MEC1 or MEC1-ROR1 cells, as indicated on the right margin. The fluorescence of cells stained with 4A5-Alexa-647 (ordinate) and anti-CD19-PE (abscissa) are shown in the contour plots. The percentages at the top right of each contour plot indicate the proportions of cells with fluorescence above the threshold indicated by the dotted line. FIG. 6C: Representative spleens of $Rag2^{-/-}\gamma_c^{-/-}$ mice 3 weeks after receiving an intravenous infusion of $1\times10^6$ MEC1-ROR1 cells and then treatment with either Ctrl-IgG or UC-961. The spleen of an age-match non-engrafted $Rag2^{-/-}\gamma_c^{-/-}$ mouse (Nor) is shown for comparison. FIG. 6D: MEC1-ROR1 cells were collected from the marrow of the femur and tibia or the spleens of mice engrafted 3-weeks earlier with MEC1-ROR1 cells and then treated with either Ctrl-IgG or UC-961, as indicated on the right. Cells were stained with 4A5-Alexa-647 and anti-CD19-PE to identify the MEC1-ROR1 cells, as in FIG. 6B. The percentages in the top right of each contour plot indicate the proportions of cells with fluorescence above the threshold indicated by the dotted line. FIG. 6E: The bars indicate the average numbers of CD19+ human leukaemia cells harvested from the marrow (left) or spleen (right) of mice engrafted 3-weeks earlier with MEC1 cells (open bars) or MEC1-ROR1 cells (black bars). Some groups of animals were treated with Ctrl-IgG or UC-961, as indicated at the bottom of each histogram. Data are shown as mean±SEM for each group of animals (n=5); P<0.01; *P<0.001.

FIG. 8A: Mass spectrum showing unique peptide of ROR2 (SEQ ID NO:24) identified by 2D-nanoLC-MS/MS from the protein lysates prepared from CLL cells following ip with anti-ROR1 mAb versus Ctrl-IgG. FIG. 8B: Total RNA was extracted from each of 3 CLL patient samples. ROR2 cDNA was amplified by RT-PCR and confirmed by DNA sequencing. Total RNA was used as PCR template to ensure there was no genomic DNA contamination. Sequence legend: ACGTGCACATGAGGTCCATT (SEQ ID NO:1; CACCGGGTGTGGGATTTACA (SEQ ID NO:2); TGCCCCGCACACATTGTTGGTCCTAT-TTGTAAATCCCA (SEQ ID NO:3); CPAHIVGPICKSH (SEQ ID NO:4). FIG. 8C: The ΔMFI for ROR1 of CLL samples (n=80) or each of the gated lymphocyte-subsets in PBMC of healthy donors (n=15), as indicated at the bottom. FIG. 8D: ROR1-ex and ROR2-ex proteins were purified and analyzed by SDS-PAGE and Coomassie staining. FIG. 8E: Chinese hamster ovary (CHO) cells were transfected with pcDNA3.1 (Vector, left panel) or pcDNA3.1-encoding ROR2 (ROR2, right panel) and then stained with a Alexa-488-labeled isotype control mAb (open histograms) or an anti-ROR2-Alexa-488 mAb for analysis by flow cytometry.

FIG. 10A: CLL cells were transfected with non-specific control siRNA (Ctrl-siRNA), or siRNA specific for ROR1 (ROR1-siRNA) or ROR2 (ROR2-siRNA), as indicated at the top of each lane. The cells were examined 48 h later for ROR1 or ROR2 via immunoblot analysis. The numbers beneath each lane is the ratio of band densities for ROR1 or ROR2 versus β-actin normalized with respect to Ctrl-siRNA treated samples. FIG. 10B: Flow cytometry of CLL cells transfected with Ctrl-siRNA (black histogram) or either ROR1-siRNA or ROR2-siRNA (grey histograms) and then stained with anti-CD5-Alexa-647 (left panel) or anti-ROR2-Alexa-488 (right panel). The open histograms are representative of the fluorescence of control or transfected CLL cells stained with an Alexa-488-labeled isotype Ctrl-IgG (Isotype).

FIG. 11A: Mass spectra showing unique peptides of ARHGEF1, ARHGEF2, or ARHGEF6 identified by 2D-nanoLC-MS/MS from the protein lysates prepared from CLL cells following ip with anti-ROR1 mAb versus Ctrl-IgG. Sequence legend: KQLL-FPAEEDNGAGPPRD (SEQ ID NO:5); KAAAQG-PEGDIQEQELQSEELGLRA (SEQ ID NO:6); WQIWELL-STDNPDALPE (SEQ ID NO:7). FIG. 11B: Immunoblot analysis of ip generated using lysates of freshly isolated CLL cells with a mAb specific for ROR1, ARHGEF1, ARHGEF2, or ARHGEF6, as indicated above each lane. The immunoblots were probed with antibodies specific for ROR1, ARHGEF1, ARHGEF2, or ARHGEF6, as indicated on the left margin of each subpanel.

FIG. 12A: Co-localization (e.g., arrow) of ROR1 with ARHGEF1, ARHGEF2, or ARHGEF6 detected by confocal microscopy in serum-starved CLL cells+/−Wnt5a (as indicated on the left margin) and Ctrl-IgG or UC-961 (Scale bar: 5 µm).

FIG. 12B: In vitro exchange over time (in minutes) of Rac1 (left panel) or RhoA (right panel) of ip from lysates of CLL cells cultured with or without Wnt5a, using mAbs specific for ARHGEF1 (left subpanel) or ARHGEF6 (right subpanel), as indicated in the bottom right of each graph. The line depicts GTPase-activation using buffer alone. FIG. 12C: CLL cells were transiently transfected with non-specific Ctrl-siRNA or siRNA specific for ARHGEF1 (ARHGEF1-siRNA), ARHGEF2 (ARHGEF2-siRNA), or ARHGEF6 (ARHGEF6-siRNA), as indicated at the top of each lane. The cells were examined 48 h later for expression of ARHGEF1, ARHGEF2, or ARHGEF6 by immunoblot analysis. The numbers beneath each lane is the ratio of band densities for each GEF versus β-actin normalized with respect to Ctrl-siRNA samples. FIG. 12D: Activation of Rac1 or RhoA in CLL cells transfected with Ctrl-siRNA, ARHGEF1-siRNA, or ARHGEF6-siRNA following treatment without (−) or with (+) Wnt5a, as indicated at the top of the lanes. Whole-cell lysates also were examined via immunoblot analysis for total Rac1 or RhoA. The numbers beneath each lane is the ratio of band densities for activated versus total GTPase normalized for untreated, Ctrl-siRNA-transfected samples.

FIG. 13A: Fluorescence of MEC1 cells, or MEC1 cells transfected with vectors encoding ROR1 or truncated forms of ROR1, stained with a fluorochrome-labeled isotype control mAb (open histogram) or 4A5-Alexa-647 (top row) or anti-ROR2-Alexa-488 (bottom row) (shaded histograms). FIG. 13B: Expression of Wnt5a was determined by immunoblot analysis of lysates from primary CLL cells or MEC1 cells. Recombinant Wnt5a (100 ng) was used as a positive control and β-actin served as a loading control for cell lysates.

FIG. 14A: Co-localization (e.g., arrow) of ROR1 and ROR2 in MEC1 cells transfected with each of the various ROR1 constructs, as indicated on the right of each row of figures (Scale bar: 2 µm). FIG. 14B: Co-localization (e.g., arrow) of ROR1 and ARHGEF1, ARHGEF2, or ARHGEF6 in MEC1 cells transfected with each of the various ROR1 constructs, as indicated on the right of each row of figures (Scale bar: 2 µm). FIG. 14C: Co-localization (e.g., arrows) of ROR2 and ARHGEF1, ARHGEF2, or ARHGEF6 in MEC1 cells transfected with each of the various ROR1 constructs, as indicated on the right of each row of figures (Scale bar: 2 µm).

DETAILED DESCRIPTION OF THE INVENTION

I. Definitions

Figure 1A:
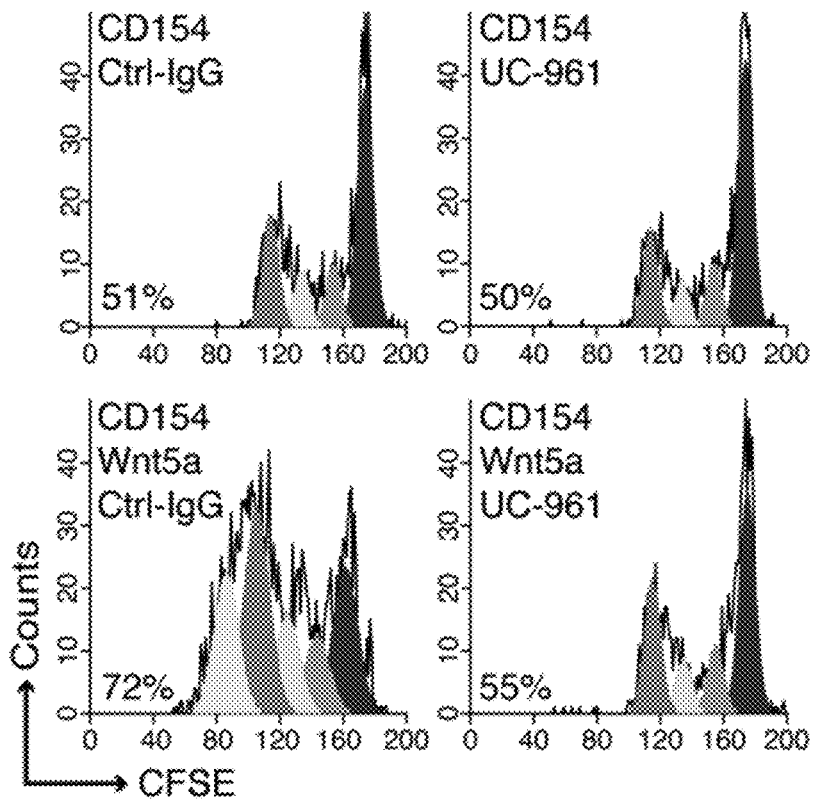
FIGS. 1A-1J. Wnt5a enhances CLL proliferation and migration through ROR1-dependent activation of Rac1 and RhoA.
Figure 1B:
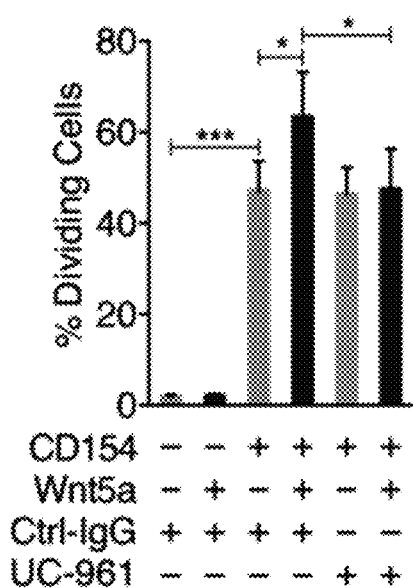

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization described below are those well-known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document.

"Nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acid as used herein also refers nucleic acids that have the same basic chemical structure as a naturally occurring nucleic acid. Such analogues have modified sugars and/or modified ring substituents, but retain the same basic chemical structure as the naturally occurring nucleic acid. A nucleic acid mimetic refers to chemical compounds that have a structure that is different the general chemical structure of a nucleic acid, but that functions in a manner similar to a naturally occurring nucleic acid. Examples of such analogues include, without limitation, phosphorothiolates, phosphoramidates, methyl phosphonates, chiral-methyl phosphonates, 2-O-methyl ribonucleotides, and peptide-nucleic acids (PNAs).

"Synthetic mRNA" as used herein refers to any mRNA derived through non-natural means such as standard oligonucleotide synthesis techniques or cloning techniques. Such mRNA may also include non-proteinogenic derivatives of naturally occurring nucleotides. Additionally, "synthetic mRNA" herein also includes mRNA that has been expressed through recombinant techniques or exogenously, using any expression vehicle, including but not limited to prokaryotic cells, eukaryotic cell lines, and viral methods. "Synthetic mRNA" includes such mRNA that has been purified or otherwise obtained from an expression vehicle or system.

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding 15 sequence if it is positioned so as to facilitate translation. Generally, "operably linked" means that the DNA sequences being linked are near each other, and, in the case of a secretory leader, contiguous and in reading phase.

The terms "polypeptide," "peptide" and "protein" are used interchangeably herein to refer to a polymer of amino acid residues, wherein the polymer may be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. The terms apply to macrocyclic peptides, peptides that have been modified with non-peptide functionality, peptidomimetics, polyamides, and macrolactams. A "fusion protein" refers to a chimeric protein encoding two or more separate protein sequences that are recombinantly expressed as a single moiety.

The term "peptidyl" and "peptidyl moiety" means a monovalent peptide.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In embodiments, there may be at least 1, at least 2, at least 3, at least 4, at least 5, at least 6, at least 7, at least 8, at least 9, at least 10, at least 15, at least 20, at least 25, at least 30, at least 35, or at least 40 conservative substitutions. In embodiments, there may be 1, 2, 3, 4, 5, 6, 7, 8, 9, 10, 15, 20, 25, 30, 35, or 40 conservative substitutions.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences of the invention or individual domains of the polypeptides of the invention), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=-4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=-4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross-reactive with the antibodies raised against the polypeptide encoded by the second nucleic acid, as described below. A polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

An amino acid or nucleotide base "position" is denoted by a number that sequentially identifies each amino acid (or nucleotide base) in the reference sequence based on its position relative to an N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to a reference sequence. In embodiments, the comparison to the reference sequence is a sequence alignment between the given amino acid or polynucleotide sequence and the reference sequence.

The term "recombinant" when used with reference to, for example, a cell, nucleic acid, or protein, indicates that the cell, nucleic acid, or protein, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express genes otherwise modified from those found in the native form of a cell (e.g. genes encoding a mutation in a native or non-native transporter protein, such as a transporter motif sequence as described herein). For example, a recombinant protein may be a protein that is expressed by a cell or organism that has been modified by the introduction of a heterologous nucleic acid (e.g. encoding the recombinant protein).

The word "expression" or "expressed" as used herein in reference to a DNA nucleic acid sequence (e.g. a gene) means the transcriptional and/or translational product of that sequence. The level of expression of a DNA molecule in a cell may be determined on the basis of either the amount of corresponding mRNA that is present within the cell or the amount of protein encoded by that DNA produced by the cell (Sambrook et al., 1989 *Molecular Cloning: A Laboratory Manual,* 18.1-18.88).

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The term "isolated" refers to a nucleic acid, polynucleotide, polypeptide, protein, or other component that is partially or completely separated from components with which it is normally associated (other proteins, nucleic acids, cells, etc.). In embodiments, an isolated polypeptide or protein is a recombinant polypeptide or protein.

A "cell culture" is an in vitro population of cells residing outside of an organism. The cell culture can be established from primary cells isolated from a cell bank or animal, or secondary cells that are derived from one of these sources and immortalized for long-term in vitro cultures.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., spodoptera) and human cells.

The terms "transfection", "transduction", "transfecting" or "transducing" can be used interchangeably and are defined as a process of introducing a nucleic acid molecule and/or a protein to a cell. Nucleic acids may be introduced to a cell using non-viral or viral-based methods. The nucleic acid molecule can be a sequence encoding complete proteins or functional portions thereof. Typically, a nucleic acid vector, comprising the elements necessary for protein expression (e.g., a promoter, transcription start site, etc.). Non-viral methods of transfection include any appropriate method that does not use viral DNA or viral particles as a delivery system to introduce the nucleic acid molecule into the cell. Exemplary non-viral transfection methods include calcium phosphate transfection, liposomal transfection, nucleofection, sonoporation, transfection through heat shock, magnetifection and electroporation. For viral-based methods, any useful viral vector can be used in the methods described herein. Examples of viral vectors include, but are not limited to retroviral, adenoviral, lentiviral and adeno-associated viral vectors. In some aspects, the nucleic acid molecules are introduced into a cell using a retroviral vector following standard procedures well known in the art. The terms "transfection" or "transduction" also refer to introducing proteins into a cell from the external environment. Typically, transduction or transfection of a protein relies on attachment of a peptide or protein capable of crossing the cell membrane to the protein of interest. See, e.g., Ford et al. (2001) Gene Therapy 8:1-4 and Prochiantz (2007) Nat. Methods 4:119-20.

The term "plasmid" refers to a nucleic acid molecule that encodes for genes and/or regulatory elements necessary for the expression of genes. Expression of a gene from a plasmid can occur in cis or in trans. If a gene is expressed in cis, gene and regulatory elements are encoded by the same plasmid. Expression in trans refers to the instance where the gene and the regulatory elements are encoded by separate plasmids.

The term "episomal" refers to the extra-chromosomal state of a plasmid in a cell. Episomal plasmids are nucleic acid molecules that are not part of the chromosomal DNA and replicate independently thereof.

The term "exogenous" refers to a molecule or substance (e.g., nucleic acid or protein) that originates from outside a given cell or organism. Conversely, the term "endogenous" refers to a molecule or substance that is native to, or originates within, a given cell or organism.

A "vector" is a nucleic acid that is capable of transporting another nucleic acid into a cell. A vector is capable of directing expression of a protein or proteins encoded by one or more genes carried by the vector when it is present in the appropriate environment.

As used herein, the terms "specific binding" or "specifically binds" refer to two molecules forming a complex (e.g., a protein complex comprising a ROR1 and a ROR2 protein, or a protein complex comprising ROR1 and/or a ROR2 protein bound to an antibody) that is relatively stable under physiologic conditions.

Methods for determining whether a ligand (e.g., antibody) binds to a protein (antigen) and/or the affinity for a ligand to a protein are known in the art. For example, the binding of a ligand to a protein can be detected and/or quantified using a variety of techniques such as, but not limited to, Western blot, dot blot, surface plasmon resonance method (e.g., BIAcore system; Pharmacia Biosensor AB, Uppsala, Sweden and Piscataway, N.J.), bio-layer interferometry (BLI) technology (e.g., Octet system; Pall ForteBio Menlo Park, Calif.), isothermal titration calorimetry (ITC), or enzyme-linked immunosorbent assays (ELISA).

Immunoassays which can be used to analyze immunospecific binding and cross-reactivity of the ligand include, but are not limited to, competitive and non-competitive assay systems using techniques such as Western blots, RIA, ELISA (enzyme linked immunosorbent assay), "sandwich" immunoassays, immunoprecipitation assays, immunodiffusion assays, agglutination assays, complement-fixation assays, immunoradiometric assays, and fluorescent immunoassays.

A "label" or a "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins (e.g., antibodies) or other entities which can be made detectable, e.g., by incorporating a radiolabel into a peptide or covalently attaching a fluorophore to an antibody specifically reactive with a target peptide. Any appropriate method known in the art for conjugating an antibody to the label may be employed, e.g., using methods described in Hermanson, Bioconjugate Techniques 1996, Academic Press, Inc., San Diego.

A "labeled protein or polypeptide" is one that is bound, either covalently, through a linker or a chemical bond, or noncovalently, through ionic, van der Waals, electrostatic, or hydrogen bonds to a label such that the presence of the labeled protein or polypeptide may be detected by detecting the presence of the label bound to the labeled protein or polypeptide. Alternatively, methods using high affinity interactions may achieve the same results where one of a pair of binding partners binds to the other, e.g., biotin, streptavidin.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which standard controls are most appropriate in a given situation and be able to analyze data based on comparisons to standard control values. Standard controls are also valuable for determining the significance (e.g. statistical significance) of data. For example, if values for a given parameter are widely variant in standard controls, variation in test samples will not be considered as significant.

The terms "inhibitor," "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90%, 95% or more in comparison to a control in the absence of the antagonist or an antagonist can decrease expression or activity by an amount that is within a range defined by any two of the aforementioned percentages in comparison to a control in the absence of the antagonist. In certain instances, expression or activity is 1.5-fold, 2-fold, 3-fold, 4-fold, 5-fold, or 10-fold lower than the expression or activity in the absence of the antagonist or expression or activity is within a range defined by any two of the aforementioned values lower than the expression or activity in the absence of the antagonist.

As defined herein, the term "inhibition", "inhibit", "inhibiting" and the like in reference to a protein-inhibitor (e.g., test agent as provided herein) interaction means negatively affecting (e.g., decreasing) the activity or function of the protein (e.g., decreasing the binding of ROR1 to ROR2 or vice versa e.g., in a protein complex comprising ROR1 and ROR2) relative to the activity or function of the protein in the absence of the inhibitor (e.g., test agent). In embodiments inhibition refers to reduction of a disease or symptoms of disease. Thus, inhibition includes, at least in part, partially or totally blocking stimulation, decreasing, preventing, or delaying activation, or inactivating, desensitizing, or down-regulating signal transduction or enzymatic activity or the amount of a protein. Similarly an "inhibitor" is a compound or protein that inhibits ROR1 or ROR2 activity, e.g., by binding, partially or totally blocking, decreasing, preventing, delaying, inactivating, desensitizing, or down-regulating enzymatic activity (e.g., ROR1 or ROR2 catalytic activity).

The term "small molecule" as used herein refers to a compound having a molecule weight of 500 Daltons or less, but greater than 1 Dalton. Although small molecules may be of biological original, small molecules are typically non-physiologic.

Antibodies are large, complex molecules (molecular weight of ~150,000 or about 1320 amino acids) with intricate internal structure. A natural antibody molecule contains two identical pairs of polypeptide chains, each pair having one light chain and one heavy chain. Each light chain and heavy chain in turn consists of two regions: a variable ("V") region involved in binding the target antigen, and a constant ("C") region that interacts with other components of the immune system. The light and heavy chain variable regions come together in 3-dimensional space to form a variable region that binds the antigen (for example, a receptor on the surface of a cell). Within each light or heavy chain variable region, there are three short segments (averaging 10 amino acids in length) called the complementarity determining regions ("CDRs"). The six CDRs in an antibody variable domain (three from the light chain and three from the heavy chain) fold up together in 3-dimensional space to form the actual antibody binding site which docks onto the target antigen. The position and length of the CDRs have been precisely defined by Kabat, E. et al., Sequences of Proteins of Immunological Interest, U.S. Department of Health and Human Services, 1983, 1987. The part of a variable region not contained in the CDRs is called the framework ("FR"), which forms the environment for the CDRs.

As used herein, the terms "complementarity determining region" and "CDR" refer to the regions that are primarily responsible for antigen-binding. There are three CDRs in a light chain variable region (CDRL1, CDRL2, and CDRL3), and three CDRs in a heavy chain variable region (CDRH1, CDRH2, and CDRH3). In embodiments, the residues forming the six CDRs are residues 24-34 (CDRL1), 50-56 (CDRL2) and 89-97 (CDRL3) in the light chain variable region and 31-35 (CDRH1), 50-65 (CDRH2) and 95-102 (CDRH3) in the heavy chain variable region. Kabat et al., (1991) Sequences of Proteins of Immunological Interest, 5th Ed. Public Health Service, National Institutes of Health, Bethesda, Md., herein incorporated by reference. In embodiments, the residues forming the six CDRs are residues 26-32 (CDRL1), 50-52 (CDRL2) and 91-96 (CDRL3) in the light chain variable region and 26-32 (CDRH1), 53-55 (CDRH2) and 96-101 (CDRH3) in the heavy chain variable region. Chothia and Lesk (1987) J. Mol. Biol. 196: 901-917, herein incorporated by reference. Unless specified, as used herein, the numbering of CDR residues is according to Kabat.

Accordingly, the term "antibody" is used according to its commonly known meaning in the art. Antibodies exist, e.g., as intact immunoglobulins or as a number of well-characterized fragments produced by digestion with various peptidases. Thus, for example, pepsin digests an antibody below the disulfide linkages in the hinge region to produce F(ab)′$_2$, a dimer of Fab which itself is a light chain joined to $V_H$-$C_{H1}$ by a disulfide bond. The F(ab)′$_2$ may be reduced under mild conditions to break the disulfide linkage in the hinge region, thereby converting the F(ab)′$_2$ dimer into an Fab′ monomer. The Fab′ monomer is essentially Fab with part of the hinge region (see Fundamental Immunology (Paul ed., 3*d* ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)). As used herein, the term "antibody fragments" refers to a portion of an antibody. Examples of antibody fragments include, but are not limited to, linear antibodies, single-chain antibody molecules, Fv, Fab and F(ab').sub.2 fragments, and multispecific antibodies formed from antibody fragments. In embodiments, the antibody fragments retain at least part of the heavy and/or light chain variable region.

For preparation of monoclonal or polyclonal antibodies, any technique known in the art can be used (see, e.g., Kohler & Milstein, *Nature* 256:495-497 (1975); Kozbor et al., *Immunology Today* 4:72 (1983); Cole et al., pp. 77-96 in *Monoclonal Antibodies and Cancer Therapy* (1985)). "Monoclonal" antibodies (mAb) refer to antibodies derived from a single clone. Techniques for the production of single chain antibodies (U.S. Pat. No. 4,946,778) can be adapted to produce antibodies to polypeptides disclosed herein. Moreover, phage display technology can be used to identify antibodies and heteromeric Fab fragments that specifically bind to selected antigens.

A humanized antibody is a genetically engineered antibody in which at least one CDR (or functional fragment thereof) from a mouse antibody ("donor antibody", which can also be rat, hamster or other non-human species) are grafted onto a human antibody ("acceptor antibody"). In embodiments, more than one mouse CDR is grafted (e.g. all six mouse CDRs are grafted). The sequence of the acceptor antibody can be, for example, a mature human antibody sequence (or fragment thereof), a consensus sequence of a human antibody sequence (or fragment thereof), or a germline region sequence (or fragment thereof). Thus, a humanized antibody may be an antibody having one or more CDRs from a donor antibody and a variable region framework (FR). In addition, in order to retain high binding affinity, amino acids in the human acceptor sequence may be replaced by the corresponding amino acids from the donor sequence, for example where: (1) the amino acid is in a CDR; (2) the amino acid is in the human framework region (e.g. the amino acid is immediately adjacent to one of the CDR's). See, U.S. Pat. Nos. 5,530,101 and 5,585,089, incorporated herein by reference, which provide detailed instructions for construction of humanized antibodies. Although humanized antibodies often incorporate all six CDRs (e.g. as defined by Kabat, but often also including hypervariable loop H1 as defined by Chothia) from a mouse antibody, they can also be made with fewer mouse CDRs and/or less than the complete mouse CDR sequence (e.g. a functional fragment of a CDR) (e.g., Pascalis et al., J. Immunol. 169:3076, 2002; Vajdos et al., Journal of Molecular Biology, 320: 415-428, 2002; Iwahashi et al., Mol. Immunol. 36:1079-1091, 1999; Tamura et al, Journal of Immunology, 164:1432-1441, 2000).

Typically a humanized antibody as provided herein may include (i) a light chain comprising at least one CDR (often three CDRs) from a mouse antibody (also referred to herein as a mouse CDR) and a human variable region framework; and (ii) a heavy chain comprising at least one CDR (often three CDRs) from the mouse antibody and a human variable region framework (FR). The light and heavy chain variable region frameworks (FRs) may each be a mature human antibody variable region framework sequence (or fragment thereof), a germline variable region framework sequence (combined with a J region sequence) (or fragment thereof), or a consensus sequence of a human antibody variable region framework sequence (or fragment thereof A chimeric antibody is an antibody in which the variable region of a mouse (or other rodent) antibody is combined with the constant region of a human antibody; their construction by means of genetic engineering is well-known. Such antibodies retain the binding specificity of the mouse antibody, while being about two-thirds human. The proportion of nonhuman sequence present in mouse, chimeric and humanized antibodies suggests that the immunogenicity of chimeric antibodies is intermediate between mouse and humanized antibodies. Other types of genetically engineered antibodies that may have reduced immunogenicity relative to mouse antibodies include human antibodies made using phage display methods (Dower et al., WO91/17271; McCafferty et al., WO92/001047; Winter, WO92/20791; and Winter, FEBS Lett. 23:92, 1998, each of which is incorporated herein by reference) or using transgenic animals (Lonberg et al., WO93/12227; Kucherlapati WO91/10741, each of which is incorporated herein by reference).

Other approaches to design humanized antibodies may also be used to achieve the same result as the methods in U.S. Pat. Nos. 5,530,101 and 5,585,089 described above, for example, "superhumanization" (see Tan et al. J. Immunol. 169: 1119, 2002, and U.S. Pat. No. 6,881,557) or the method of Studnicak et al., Protein Eng. 7:805, 1994. Moreover, other approaches to produce genetically engineered, reduced-immunogenicity mAbs include "reshaping", "hyperchimerization" and veneering/resurfacing, as described, e.g., in Vaswami et al., Annals of Allergy, Asthma and Immunology 81:105, 1998; Roguska et al. Protein Eng. 9:895, 1996; and U.S. Pat. Nos. 6,072,035 and 5,639,641; Methods Mol Biol. 2009; 525:405-23, Deimmunization of monoclonal antibodies. Jones T D 1, Crompton L J, Carr F J, Baker M P.

The epitope of a mAb is the region of its antigen to which the mAb binds. Two antibodies bind to the same or overlapping epitope if each competitively inhibits (blocks) binding of the other to the antigen. That is, a 1×, 5×, 10×, 20× or 100× excess of one antibody or an amount of one antibody that is within a range defined by any two of the aforementioned amounts inhibits binding of the other by at least 30% but preferably 50%, 75%, 90% or even 99% or within a range defined by any two of the aforementioned values, as measured in a competitive binding assay (see, e.g., Junghans et al., Cancer Res. 50:1495, 1990). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

A "ROR1 protein" as referred to herein includes any of the recombinant or naturally-occurring forms of the tyrosine-protein kinase transmembrane receptor (ROR1) also known as neurotrophic tyrosine kinase receptor-related 1 (NTRKR1) or variants or homologs thereof that maintain ROR1 kinase activity (e.g. within at least 50%, 80%, 90%, 95%, 96%, 97%, 98%, 99% or 100% activity or within a range of activity defined by any two of the aforementioned values compared to ROR1). In some aspects, the variants or homologs have at least 90%, 95%, 96%, 97%, 98%, 99% or 100% amino acid sequence identity or within a range of identities defined by any two of the aforementioned values across the whole sequence or a portion of the sequence (e.g. a 50, 100, 150 or 200 continuous amino acid portion or within a range defined by any two of the aforementioned lengths) compared to a naturally occurring ROR1 protein. In embodiments, the ROR1 protein is substantially identical to the protein identified by the UniProt reference number Q01973 (SEQ ID NO:8) or a variant or homolog having substantial identity thereto. In embodiments, the ROR1 protein is substantially identical to the protein identified by the UniProt reference number Q9Z139 (SEQ ID NO:9) or a variant or homolog having substantial identity thereto.

A "ROR2 protein" as referred to herein includes any of the recombinant or naturally-occurring forms of the tyrosine-protein kinase transmembrane receptor (ROR2) also known as neurotrophic tyrosine kinase receptor-related 1 (NTRKR2) or variants or homologs thereof that maintain ROR2 kinase activity (e.g. within at least 50%, 80%, 90%, 95%, 96%, 97%, 98%, 99% or 100% activity or within a range of activity defined by any two of the aforementioned values compared to ROR2). In some aspects, the variants or homologs have at least 90%, 95%, 96%, 97%, 98%, 99% or 100% amino acid sequence identity or within a range of identities defined by any two of the aforementioned values across the whole sequence or a portion of the sequence (e.g. a 50, 100, 150 or 200 continuous amino acid portion or within a range defined by any two of the aforementioned lengths) compared to a naturally occurring ROR2 protein. In embodiments, the ROR2 protein is substantially identical to the protein identified by the UniProt reference number Q01974 (SEQ ID NO:10) or a variant or homolog having substantial identity thereto. In embodiments, the ROR2 protein is substantially identical to the protein identified by the UniProt reference number Q9Z138 (SEQ ID NO:11) or a variant or homolog having substantial identity thereto.

The terms "siRNA," "small interfering RNA" and the like refer, in the usual and customary sense, to RNA molecules of typically 20-25 base pairs in length, which operate within the RNA interference pathway by interfering with the expression of specific genes with complementary nucleotide sequences. Without wishing to be bound by any theory, it is believed that siRNA assists in degradation of mRNA after transcription, thereby removing transcripts which would otherwise be expressed. The term "siRNA is specific for ROR1 or ROR2" means that the siRNA reduces or prevents expression of ROR1 or ROR2 upon contact in an expression system, e.g., in a cell.

A "Wnt5a protein" as referred to herein includes any of the recombinant or naturally-occurring forms of the wingless-type MMTV integration site family, member 5a (Wnt5a) or variants or homologs thereof that maintain Wnt5a activity (e.g. within at least 50%, 80%, 90%, 95%, 96%, 97%, 98%, 99% or 100% activity compared to Wnt5a or within a range of activity defined by any two of the aforementioned values compared to Wnt5a). In some aspects, the variants or homologs have at least 90%, 95%, 96%, 97%, 98%, 99% or 100% amino acid sequence identity or within a range of identities defined by any two of the aforementioned values across the whole sequence or a portion of the sequence (e.g. a 50, 100, 150 or 200 continuous amino acid portion or within a range of defined by any two of the aforementioned lengths) compared to a naturally occurring Wnt5a protein. In embodiments, the Wnt5a protein is substantially identical to the protein identified by the UniProt reference number P41221 (SEQ ID NO:12) or a variant or homolog having substantial identity thereto. In embodiments, the Wnt5a protein is substantially identical to the protein identified by the UniProt reference number P22725 (SEQ ID NO:13) or a variant or homolog having substantial identity thereto.

A "RhoA protein" or "RhoA" as referred to herein includes any of the recombinant or naturally-occurring forms of the Ras homolog gene family member A (RhoA) or variants or homologs thereof that maintain RhoA GTPase (guanosine triphosphatase) activity (e.g. within at least 50%, 80%, 90%, 95%, 96%, 97%, 98%, 99% or 100% activity or within a range of activity defined by any two of the aforementioned values compared to RhoA). In some aspects, the variants or homologs have at least 90%, 95%, 96%, 97%, 98%, 99% or 100% amino acid sequence identity or within a range of identities defined by any two of the aforementioned values across the whole sequence or a portion of the sequence (e.g. a 50, 100, 150 or 200 continuous amino acid portion or within a range of defined by any two of the aforementioned lengths) compared to a naturally occurring RhoA protein. In embodiments, the RhoA protein is substantially identical to the protein identified by the UniProt reference number P61586 (SEQ ID NO:14) or a variant or homolog having substantial identity thereto. In embodiments, the RhoA protein is substantially identical to the protein identified by the UniProt reference number Q9QUI0 (SEQ ID NO:15) or a variant or homolog having substantial identity thereto.

A "Rac1 protein" or "Rac1" as referred to herein includes any of the recombinant or naturally-occurring forms of the Ras-related C3 botulinum toxin substrate 1 (Rac1) or variants or homologs thereof that maintain Rac1 GTPase (guanosine triphosphatase) activity (e.g. within at least 50%, 80%, 90%, 95%, 96%, 97%, 98%, 99% or 100% activity or within a range of activity defined by any two of the aforementioned values compared to Rac1). In some aspects, the variants or homologs have at least 90%, 95%, 96%, 97%, 98%, 99% or 100% amino acid sequence identity or within a range of identities defined by any two of the aforementioned values across the whole sequence or a portion of the sequence (e.g. a 50, 100, 150 or 200 continuous amino acid portion or within a range of lengths defined by any two of the aforementioned values) compared to a naturally occurring Rac1 protein. In embodiments, the Rac1 protein is substantially identical to the protein identified by the UniProt reference number P63000 (SEQ ID NO:16) or a variant or homolog having substantial identity thereto. In embodiments, the Rac1 protein is substantially identical to the protein identified by the UniProt reference number P63001 (SEQ ID NO:17) or a variant or homolog having substantial identity thereto.

A "ARHGEF1 protein" or "ARHGEF1" as referred to herein includes any of the recombinant or naturally-occurring forms of the Rho guanine nucleotide exchange factor 1 (ARHGEF1) or variants or homologs thereof that maintain ARHGEF1 activity (e.g. within at least 50%, 80%, 90%, 95%, 96%, 97%, 98%, 99% or 100% activity or within a range of activity defined by any two of the aforementioned values compared to ARHGEF1). In some aspects, the variants or homologs have at least 90%, 95%, 96%, 97%, 98%, 99% or 100% amino acid sequence identity or within a range of identities defined by any two of the aforementioned values across the whole sequence or a portion of the sequence (e.g. a 50, 100, 150 or 200 continuous amino acid portion or within a range of lengths defined by any two of the aforementioned values) compared to a naturally occurring ARHGEF1 protein. In embodiments, the ARHGEF1 protein is substantially identical to the protein identified by the UniProt reference number Q92888 (SEQ ID NO:18) or a variant or homolog having substantial identity thereto. In embodiments, the ARHGEF1 protein is substantially identical to the protein identified by the UniProt reference number Q61210 (SEQ ID NO:19) or a variant or homolog having substantial identity thereto.

A "ARHGEF2 protein" or "ARHGEF2" as referred to herein includes any of the recombinant or naturally-occurring forms of the Rho guanine nucleotide exchange factor 2 (ARHGEF2) or variants or homologs thereof that maintain ARHGEF2 activity (e.g. within at least 50%, 80%, 90%, 95%, 96%, 97%, 98%, 99% or 100% activity or within a range of activity defined by any two of the aforementioned values compared to ARHGEF2). In some aspects, the variants or homologs have at least 90%, 95%, 96%, 97%, 98%, 99% or 100% amino acid sequence identity or within a range of identities defined by any two of the aforementioned values across the whole sequence or a portion of the sequence (e.g. a 50, 100, 150 or 200 continuous amino acid portion or within a range of lengths defined by any two of the aforementioned values) compared to a naturally occurring ARHGEF2 protein. In embodiments, the ARHGEF2 protein is substantially identical to the protein identified by the UniProt reference number Q92974 (SEQ ID NO:20) or a variant or homolog having substantial identity thereto. In embodiments, the ARHGEF2 protein is substantially identical to the protein identified by the UniProt reference number Q60875 (SEQ ID NO:21) or a variant or homolog having substantial identity thereto.

A "ARHGEF6 protein" or "ARHGEF6" as referred to herein includes any of the recombinant or naturally-occurring forms of the Rho guanine nucleotide exchange factor 6 (ARHGEF6) or variants or homologs thereof that maintain ARHGEF6 activity (e.g. within at least 50%, 80%, 90%, 95%, 96%, 97%, 98%, 99% or 100% activity or within a range of activity defined by any two of the aforementioned values compared to ARHGEF6). In some aspects, the variants or homologs have at least 90%, 95%, 96%, 97%, 98%, 99% or 100% amino acid sequence identity or within a range of identities defined by any two of the aforementioned values across the whole sequence or a portion of the sequence (e.g. a 50, 100, 150 or 200 continuous amino acid portion or within a range of lengths defined by any two of the aforementioned values) compared to a naturally occurring ARHGEF6 protein. In embodiments, the ARHGEF6 protein is substantially identical to the protein identified by the UniProt reference number Q15052 (SEQ ID NO:22) or a variant or homolog having substantial identity thereto. In embodiments, the ARHGEF6 protein is substantially identical to the protein identified by the UniProt reference number Q8K4I3 (SEQ ID NO:23) or a variant or homolog having substantial identity thereto.

The terms "UC-961," "Cirmtuzumab" and the like refer, in the usual and customary sense, to a monoclonal antibody drug agent which is capable of binding to ROR1, e.g., expressed on the surface of CLL cells. Binding of UC-961 to ROR1 may block cell growth and survival.

The term "fluorescence resonance energy transfer," "FRET" and the like refer, in the usual and customary sense, to a mechanism of energy transfer between two light-sensitive species (e.g., detectable moieties such as chromophores or fluorophores). Energy transfer between such molecules can be mediated through non-radiative dipole-dipole coupling, the efficiency of which is inversely proportional to the sixth-power of the distance. Thus, FRET can be exquisitely sensitive to the distance between the donor and acceptor light-sensitive species, as known in the art.

The term "KNG domain of ROR1" and the like refer, in the usual and customary sense, to the extracellular kringle (KNG) domain of ROR1. The term "KNG domain of ROR2" and the like refer, in the usual and customary sense, to the KNG domain of ROR2. As known in the art, kringle domains are autonomous protein domains that fold into characteristic large loops stabilized by disulfide linkages. In embodiments, the KNG domain corresponds to amino acid residues 310-392 of SEQ ID NO: 8. In embodiments, the KNG domain corresponds to amino acid residues 314-395 of SEQ ID NO:10.

As used herein, the term "cancer" refers to all types of cancer, neoplasm or malignant tumors found in mammals, including leukemias, lymphomas, melanomas, neuroendocrine tumors, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g. hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, pre-invasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

The term "associated" or "associated with" in the context of a substance or substance activity or function associated with a disease (e.g., diabetes, cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma)) means that the disease (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma) is caused by (in whole or in part), or a symptom of the disease is caused by (in whole or in part) the substance or substance activity or function.

II. Methods

ROR1-associated proteins in primary CLL cells were examined. It was unexpectedly found that ROR1 couples with ROR2 in response to Wnt5a to recruit guanine exchange factors (GEFs) that activate Rho GTPases.

Wnt5a can activate GTPases RhoA and Rac1 in chronic lymphocytic leukemia (CLL) cells to enhance leukemia-cell migration and proliferation, respectively. It has been found that Wnt5a is present at high levels in the plasma of patients with CLL relative to that of healthy donors and that of freshly isolated leukemia cells.

Thus in one aspect, a method of determining an expression level of a Wnt5a protein in a subject that has or is at risk for developing cancer is provided. The method includes (i) obtaining a biological sample from the subject; (ii) determining an expression level of a Wnt5a protein in the biological sample. In embodiments, the determining includes: (a) contacting the Wnt5a protein with a Wnt5a protein binding agent in the biological sample, thereby forming a Wnt5a protein-binding agent complex; and (b) detecting said Wnt5a protein-binding agent complex. "Wnt5a protein binding agent" as provided herein refers to a substance capable of binding a Wnt5a protein. The Wnt5a protein binding agent may be a nucleic acid or a protein. In embodiments, the Wnt5a protein binding agent is an aptamer. In embodiments, the Wnt5a protein binding agent is peptide. In embodiments, the Wnt5a protein binding agent is a small molecule. In embodiments, the Wnt5a protein binding agent is an antibody. In embodiments, the Wnt5a protein binding agent includes a detectable moiety. In embodiments, the method includes further selecting a subject that has or is at risk for developing cancer. In embodiments, the biological sample is a blood-derived biological sample of the subject. In embodiments, the blood-derived biological sample is whole blood, serum or plasma. In embodiments, the cancer is chronic lymphocytic leukemia (CLL).

Without being bound by any particular mechanism of action, evidence has been found that ROR1-associated proteins in chronic lymphocytic leukemia (CLL), including ROR2, can be found on CLL and CD5 B cells. Wnt5a induces ROR1-ROR2 coupling (binding), which recruits ARHGEF1, ARHGEF2 and ARHGEF6, and activated RhoA and Rac1, enhancing CLL-cell migration and proliferation. Using the CLL-cell-line MEC1 (which lacks ROR1 but expresses ROR2 and Wnt5a) it has been found that, compared to parental cells, MEC1 made to express ROR1 had ROR1-ROR2 complexes, which recruited guanine exchange factors, increased cytokine-directed migration, and enhanced engraftment in immune-deficient mice. The extracellular Kringle domain is required for ROR1-ROR2 coupling (binding) and the cysteine-rich domain or intracellular proline-rich domain is required for Wnt5a-induced recruitment of guanine exchange factors to ROR1-ROR2. Further, it has been found that coupling (binding) of ROR1 with ROR2 accounts for its noted biologic activity in blocking non-canonical Wnt signaling by Wnt5a, which, it has been found, enhances the proliferation, survival, and metastasis of cancer cells in vivo.

There are no assays known to be available with which to test for agents that can interfere with the coupling (binding) of ROR1 with ROR2, as this has not previously been recognized as a requirement for non-canonical Wnt-signaling. Such an assay is provided herein.

To that end, it has also now been established that antibodies (such as our anti-ROR1 mAb, UC-961) can inhibit the capacity of ROR1 to couple with ROR2, and thereby block the effect that Wnt5a can have on cancer cells in inducing activation of RhoA and Rac1.

These discoveries allow for the following to be provided by this invention:
1) Assays to monitor the capacity of Wnt5a to couple ROR1 with ROR2.
2) Antibodies to ROR1 or ROR2 that can inhibit the capacity of ROR1 to couple with ROR2 and thereby block Wnt5a-induced signaling.
3) Screening of polypeptides or small molecules that can inhibit the capacity of ROR1 to couple with ROR2.
4) Characterization and ranking of the relative effectiveness of molecules intended to block the coupling (binding) of ROR1 with ROR2 that is required for Wnt5a-induced non-canonical Wnt signaling.

Screening for ROR1-ROR2 coupling (binding) inhibitors may be performed with fluorescence confocal microscopy or Fluorescence Resonance Energy Transfer (FRET) assay to monitor for co-localization of ROR1 with ROR2 or by other means, such as a cell-based assay. Screening could be automated so that it could be used to screen for antibodies or other agents (small molecules, peptides, drugs, etc.), which interfere with the coupling (binding) of ROR1 and ROR2. Agents that interfere with such coupling (binding) would be expected to interfere with the non-canonical Wnt signaling induced by Wnt5a.

Provided herein are, inter alia, methods of identifying agents capable of inhibiting the binding between ROR1 and ROR2 (e.g., the formation or maintenance of a protein complex comprising ROR1 and ROR2). The identified agents may inhibit ROR1-ROR2-binding and/or the formation or maintenance of a protein complex comprising ROR1 and ROR2 by interacting with ROR1, thereby preventing binding of ROR1 to ROR2. Alternatively, the identified agents may inhibit the binding by interacting with ROR2, thereby preventing binding of ROR1 to ROR2. Through their ability to inhibit the binding of ROR1 to ROR2 and/or the formation or maintenance of a protein complex comprising ROR1 and ROR2, the agents identified by the methods provided herein may be useful as cancer diagnostics or cancer therapeutics.

For the aspects and embodiments provided herein referring to "the binding between ROR1 and ROR2" it is understood that this phrase includes the formation or maintenance of a protein complex including ROR1 and ROR2. Thus, in one aspect a method of identifying an inhibitor of ROR1-ROR2 binding and/or the formation or maintenance of a protein complex comprising ROR1 and ROR2 is provided. The method includes (i) combining a test agent with a ROR1 protein and a ROR2 protein in a reaction vessel. (ii) A decrease in binding of the ROR1 protein to the ROR2 protein and/or the formation or maintenance of a protein complex comprising ROR1 and ROR2 relative to a standard control is detected and thereby an inhibitor of ROR1-ROR2 binding and/or the formation or maintenance of a protein complex comprising ROR1 and ROR2 is identified.

In one aspect, a method of identifying an inhibitor of ROR1-ROR2 binding is provided. The method includes (i) combining a test agent with a ROR1 protein and a ROR2 protein in a reaction vessel. (ii) A decrease in binding of the ROR1 protein to the ROR2 protein relative to a standard control is detected and thereby an inhibitor of ROR1-ROR2 binding is identified. The term "binding" as provided herein refers to the association between a ROR1 protein and a ROR2 protein. The association can be direct (e.g., by covalent bond) or indirect (e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like)). Thus, the term "binding" includes the formation or maintenance of a protein complex comprising ROR1 and ROR2. The binding of ROR1 to ROR2 and/or the formation or maintenance of a protein complex comprising ROR1 and ROR2 as provided herein may also be referred to as "heterooligomerization" or "coupling." In embodiments, ROR1-ROR2 binding and/or the formation or maintenance of a protein complex comprising ROR1 and ROR2 is preceded by binding of Wnt5a to ROR1 or ROR2. In embodiments, ROR1-ROR2 binding and/or the formation or maintenance of a protein complex comprising ROR1 and ROR2 increases the level of a guanine exchange factor (GEF) or a GTPase. The interaction between the ROR1 protein and the ROR2 protein and/or the formation or maintenance of a protein complex comprising ROR1 and ROR2 may be inhibited by binding of the test agent to a KNG domain. In embodiments, the KNG domain forms part of the ROR1 protein. In embodiments, the KNG domain forms part of the ROR2 protein.

For the methods provided herein including embodiments thereof, the ROR1 protein and the ROR2 protein may be expressed by a cell. In embodiments, the reaction vessel includes a cell. In embodiments, the ROR1 protein and the ROR2 protein are expressed on the surface of a cell. The cell may form part of an in vitro cell culture. In embodiments, the in vitro cell culture includes a Wnt5 protein. Thus, in embodiments, the combining step occurs in the presence of a Wnt5a protein. In embodiments, the cell expresses an endogenous Wnt5a protein. In embodiments, the formation or maintenance of a protein complex comprising ROR1 and ROR2 occurs in the presence of a Wnt5a protein. In embodiments, the cell expresses an exogenous Wnt5a protein. Thus, in embodiments, the cell is transfected with a vector encoding a Wnt5a protein.

In embodiments, the reaction vessel includes a cell culture. A "cell culture" as provided herein refers to an environment including appropriate cellular nutrients and capable of maintaining cells in vitro. The environment may be a liquid environment, a solid environment and/or a semisolid environment (e.g. agar, gel etc.) in an appropriate vessel (e.g., cell culture dish). A cell culture medium may be employed. A "cell culture medium" as used herein, is used according to its generally accepted meaning in the art. A cell culture medium (also referred to in the art and herein as a "culture medium") includes liquids (e.g., growth factors, minerals, vitamins etc.) or gels designed to support the growth (e.g. division, differentiation, maintenance etc.) of cells. In embodiments, the compositions provided herein including embodiments, further include a physiologically acceptable solution. A "physiologically acceptable solution" as provided herein refers to any acceptable aqueous solution (e.g., buffer) in which the compositions provided herein may be contained without losing their biological properties. In embodiments, the physiologically acceptable solution is a cell culture medium. Thus, in embodiments, the cell forms part of an in vitro cell culture.

In embodiments, the cell is a cancer cell. In embodiments, the cancer cell is a chronic lymphocytic leukemia (CLL) cell. In embodiments, the CLL cell is a chronic B cell leukemia cell. In embodiments, the CLL cell is a MEC1 cell. In the customary sense, a MEC1 cell as provided herein refers to a cell as deposited with the Leibniz Institute DSMZ-German Collection of Microorganisms and Cell Cultures and having the accession number ACC 497. In embodiments, the MEC1 cell expresses a ROR1 protein and a ROR2 protein. In further embodiments, the ROR1 protein is an exogenous protein and the ROR2 protein is an endogenous protein. In other words, the MEC1 cell may endogenously express a ROR2 protein and by transfection with a vector expressing a ROR1 protein form a MEC1 cell expressing a ROR1 protein and a ROR2 protein.

In embodiments, the ROR1 protein and the ROR2 protein are isolated proteins and the method is performed in a cell-free environment. In embodiments, the combining includes binding (allowing binding of) an isolated ROR1 protein to a solid support thereby forming a bound ROR1 protein and contacting the bound ROR1 protein with an isolated ROR2 protein and a test agent. Thus, in embodiments, the reaction vessel is a column including a solid support. A "solid support" as provided herein refers to any material that can be modified to contain discrete individual sites appropriate for the attachment or association of an isolated ROR1 protein or an isolated ROR2 protein or fragment thereof as provided herein including embodiments thereof and is amenable to the methods provided herein including embodiments thereof. Examples of solid supports include without limitation, glass and modified or functionalized glass (e.g., carboxymethyldextran functionalized glass), plastics (including acrylics, polystyrene and copolymers of styrene and other materials, polypropylene, polyethylene, polybutylene, polyurethanes, Teflon™, etc.), polysaccharides (e.g., sepharose, agarose), nylon or nitrocellulose, composite materials, ceramics, and plastic resins, silica or silica-based materials including silicon and modified silicon (e.g., patterned silicon), carbon, metals, quartz (e.g., patterned quartz), inorganic glasses, plastics, optical fiber bundles, and a variety of other polymers. In general, the substrates allow optical detection and do not appreciably fluoresce.

In embodiments, the detecting includes detecting a level of the ROR1 protein bound to the ROR2 protein in the presence of the test agent, wherein a decreased level of the ROR1 protein bound to the ROR2 protein relative to a standard control indicates the test agent is an inhibitor of ROR1-ROR2 binding. The standard control may be the level of binding of a ROR1 protein to a ROR2 protein in the absence of the test agent. In embodiments, the standard control is the level of binding of a ROR1 protein to a ROR2 protein in the presence of an agent unable to inhibit binding of the ROR1 protein to the ROR2 protein. In embodiments, the standard control is the level of binding of a ROR1 protein to a ROR2 protein in the presence of an agent unable to bind to the ROR1 protein or the ROR2 protein. In embodiments, the standard control is the level of binding of a ROR1 protein to a ROR2 protein in the presence of an agent unable to bind to the KNG domain of a ROR1 protein. In embodiments, the standard control is the level of binding of a ROR1 protein to a ROR2 protein in the presence of a ROR1 antibody. In further embodiments, said ROR1 antibody is a 4A5 antibody.

In embodiments, the detecting includes detecting a level of the formation or maintenance of a protein complex comprising ROR1 and ROR2 in the presence of the test agent, wherein a decreased level of the ROR1 protein or the ROR2 protein in the complex relative to a standard control indicates the test agent is an inhibitor of ROR1-ROR2 binding. The standard control may be the level of the formation or maintenance of a protein complex comprising ROR1 and ROR2 in the absence of the test agent. In embodiments, the standard control is the formation or maintenance of a protein complex comprising ROR1 and ROR2 in the presence of an agent previously shown to not inhibit binding of the ROR1 protein to the ROR2 protein. In embodiments, the standard control is the level of the formation or maintenance of a protein complex comprising ROR1 and ROR2 in the presence of an agent previously shown to not bind to the ROR1 protein or the ROR2 protein. In embodiments, the standard control is the level of the formation or maintenance of a protein complex comprising ROR1 and ROR2 in the presence of an agent previously shown to not bind to the KNG domain of a ROR1 protein. In embodiments, the standard control is the level of the formation or maintenance of a protein complex comprising ROR1 and ROR2 in the presence of a ROR1 antibody. In further embodiments, said ROR1 antibody is a 4A5 antibody.

In embodiments, the detecting includes detecting a level of unbound ROR1 protein or unbound ROR2 protein in the presence of the test agent, wherein an increased level of unbound ROR1 protein or an increased level of unbound ROR2 protein relative to a standard control indicates the test agent is an inhibitor of ROR1-ROR2 binding. The term "unbound ROR1 protein" as provided herein refers to a ROR1 protein, which does not form part of a complex or is not bound to a ROR2 protein. The term "unbound ROR2 protein" as provided herein refers to a ROR2 protein, which does not form part of a complex or is not bound to a ROR1 protein. In embodiments, the standard control is the level of unbound ROR1 protein or unbound ROR2 protein in the absence of the test agent. In embodiments, the standard control is the level of unbound ROR1 protein or unbound ROR2 protein in the presence of an agent unable to inhibit binding of the ROR1 protein to the ROR2 protein. In embodiments, the standard control is the level of unbound ROR1 protein or unbound ROR2 protein in the presence of an agent unable to bind to the ROR1 protein or the ROR2 protein. In embodiments, the standard control is the level of binding of a ROR1 protein to a ROR2 protein in the presence of an agent unable to bind to the KNG domain of a ROR1 protein. In embodiments, the standard control is the level of binding of a ROR1 protein to a ROR2 protein in the presence of a ROR1 antibody. In further embodiments, said ROR1 antibody is a 4A5 antibody.

In embodiments, the detecting includes detecting a level of unbound ROR1 protein or unbound ROR2 protein in a protein complex comprising ROR1 and ROR2 in the presence of the test agent, wherein an increased level of unbound ROR1 protein or an increased level of unbound ROR2 protein relative to a standard control indicates the test agent is an inhibitor of the formation or maintenance of a protein complex comprising ROR1 and ROR2. In embodiments, the standard control is the level of unbound ROR1 protein or unbound ROR2 protein in a protein complex comprising ROR1 and ROR2 in the absence of the test agent. In embodiments, the standard control is the level of unbound ROR1 protein or unbound ROR2 protein in a protein complex comprising ROR1 and ROR2 in the presence of an agent previously shown to not inhibit the formation or maintenance of a protein complex comprising ROR1 and ROR2. In embodiments, the standard control is the level of the formation or maintenance of a protein complex comprising ROR1 and ROR2 in the presence of an agent previously shown to not bind to the KNG domain of a ROR1 protein. In embodiments, the standard control is the level of binding of the formation or maintenance of a protein complex comprising ROR1 and ROR2 in the presence of a ROR1 antibody. In further embodiments, said ROR1 antibody is a 4A5 antibody.

In embodiments, the detecting includes detecting a level of a guanine exchange factor (GEF) protein activity or a guanosine triphosphatase (GTPase) protein activity in the presence of the test agent, wherein a decreased level of the GEF protein activity or the GTPase protein activity relative to a standard control indicates the test agent is an inhibitor of ROR1-ROR2 binding (e.g., the formation or maintenance of a protein complex comprising ROR1 and ROR2). In embodiments, the standard control is the level of GEF protein activity or GTPase protein activity in the absence of the test agent. In embodiments, the GEF protein is ARHGEF1, ARHGEF2 or ARHGEF6. In embodiments, the GEF protein is ARHGEF1. In embodiments, the GEF protein is ARHGEF2. In embodiments, the GEF protein is ARHGEF6. In embodiments, the GTPase protein is RhoA or Rac1. In embodiments, the GTPase protein is RhoA. In embodiments, the GTPase protein is Rac1.

In embodiments, the ROR1 protein and the ROR2 protein include a detectable moiety. In embodiments, the GEF protein or the GTPase protein include a detectable moiety. A detectable moiety is as defined herein. In embodiments, the detectable moiety is a bioluminescent molecule. In embodiments, the detectable moiety is a photoactive molecule. In embodiments, the detectable moiety is a fluorophore. In embodiments, the detectable moiety is an antibody including a fluorophore. In embodiments, the detectable moiety and the ROR1 protein form a fusion protein. In embodiments, the detectable moiety and the ROR2 protein form a fusion protein. A wide variety of detectable moieties can be used, with the choice of label depending on the sensitivity required, ease of conjugation with the antibody, stability requirements, and available instrumentation and disposal provisions. Suitable detectable moieties include, but are not limited to, radionuclides, fluorescent dyes (e.g., fluorescein, fluorescein isothiocyanate (FITC), Oregon Green™, rhodamine, Texas red, tetrarhodimine isothiocynate (TRITC), Cy3, Cy5, etc.), fluorescent markers (e.g., green fluorescent protein (GFP), phycoerythrin, etc.), autoquenched fluorescent compounds that are activated by tumor-associated proteases, enzymes (e.g., luciferase, horseradish peroxidase, alkaline phosphatase, etc.), nanoparticles, biotin, digoxigenin, and the like. In embodiments, the detectable moiety is amenable to a Fluorescence Resonance Energy Transfer (FRET) assay or to a fluorescent colocalization assay. Thus, in embodiments, the reaction vessel forms part of a fluorescent detection device.

The step of detection as provided herein may include immunoassay techniques and protocols generally known and described in the art. See Price and Newman, "Principles and Practice of Immunoassay," 2nd Edition, Grove's Dictionaries, 1997; and Gosling, "Immunoassays: A Practical Approach," Oxford University Press, 2000. A variety of immunoassay techniques, including competitive and non-competitive immunoassays, can be used (see, e.g., Self et al., Curr. Opin. Biotechnol., 7:60-65 (1996)). The term immunoassay encompasses techniques including, without limitation, enzyme immunoassays (EIA) such as enzyme multiplied immunoassay technique (EMIT), enzyme-linked immunosorbent assay (ELISA), IgM antibody capture ELISA (MAC ELISA), and microparticle enzyme immunoassay (META); capillary electrophoresis immunoassays (CEIA); radioimmunoassays (RIA); immunoradiometric assays (IRMA); fluorescence polarization immunoassays (FPIA); and chemiluminescence assays (CL). If desired, such immunoassays can be automated. Immunoassays can also be used in conjunction with laser induced fluorescence (see, e.g., Schmalzing et al., *Electrophoresis*, 18:2184-93 (1997); Bao, *J. Chromatogr. B. Biomed. Sci.*, 699:463-80 (1997)). Liposome immunoassays, such as flow-injection liposome immunoassays and liposome immunosensors, are also suitable for use in the present invention (see, e.g., Rongen et al., *J. Immunol. Methods*, 204:105-133 (1997)). In addition, nephelometry assays, in which the formation of protein/antibody complexes results in increased light scatter that is converted to a peak rate signal as a function of the marker concentration, are suitable for use in the methods of the present invention. Nephelometry assays are commercially available from Beckman Coulter (Brea, Calif.; Kit #449430) and can be performed using a Behring Nephelometer Analyzer (Fink et al., *J. Clin. Chem. Clin. Biochem.*, 27:261-276 (1989)).

Specific immunological binding of the antibody or binding reagent to a ROR1 protein or a ROR2 protein can be detected directly or indirectly. Direct labels include fluorescent or luminescent tags, metals, dyes, radionuclides, and the like, attached to the antibody. An antibody labeled with iodine-125 ($^{125}$I) can be used. A chemiluminescence assay using a chemiluminescent antibody specific for the protein marker is suitable for sensitive, non-radioactive detection of protein levels. An antibody labeled with fluorochrome is also suitable. Examples of fluorochromes include, without limitation, DAPI, fluorescein, Hoechst 33258, R-phycocyanin, B-phycoerythrin, R-phycoerythrin, rhodamine, Texas red, and lissamine. Indirect labels include various enzymes well known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. An urease detection system can be used with a substrate such as urea-bromocresol purple (Sigma Immunochemicals; St. Louis, Mo.).

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously.

In embodiments, the detecting step includes detecting ROR1-ROR2 binding by confocal microscopy. Optical images viewed (and, optionally, recorded) by a camera or other recording device (e.g., a photodiode and data storage device) are optionally further processed in any of the embodiments herein, e.g., by digitizing the image and storing and analyzing the image on a computer. A variety of commercially available peripheral equipment and software is available for digitizing, storing and analyzing a digitized video or digitized optical images.

One conventional system carries light from the specimen field to a cooled charge-coupled device (CCD) camera, in common use in the art. A CCD camera includes an array of picture elements (pixels). The light from the specimen is imaged on the CCD. Particular pixels corresponding to regions of the specimen are sampled to obtain light intensity readings for each position. Multiple pixels are processed in parallel to increase speed. The apparatus and methods of the invention are easily used for viewing any sample, e.g., by fluorescent or dark field microscopic techniques.

The test agents provided herein may be any compound capable of inhibiting the binding of a ROR1 protein to a ROR2 protein (e.g., the formation or maintenance of a protein complex comprising ROR1 and ROR2). In embodiments, the test agent is an antibody, a small molecule, a peptide, a protein or a nucleic acid. In embodiments, the test agent is an antibody. The antibody may be an anti-ROR1 antibody. In embodiments, the antibody is an anti-ROR2 antibody. Thus, in embodiments, the antibody binds to a ROR1 protein or a ROR2 protein. In embodiments, the antibody binds to a KNG domain. In embodiments, the antibody is a humanized antibody. In embodiments, the antibody is a chimeric antibody. In embodiments, the antibody is a scFv. In embodiments, the test agent is a small molecule. In embodiments, the test agent is a peptide. In embodiments, the test agent is a protein. In embodiments, the test agent is a nucleic acid.

In one aspect, an antibody identified by the method provided herein including embodiments thereof is provided. In embodiments, the antibody is an anti-ROR1 antibody. In embodiments, the antibody binds the KNG domain of a ROR1 protein. In embodiments, the antibody is cirmtuzumab.

In another aspect, a method of inhibiting a ROR1-ROR2 interaction (e.g., the formation or maintenance of a protein complex comprising ROR1 and ROR2) is provided. The method includes (i) contacting a compound identified by the method provided herein including embodiments thereof with a ROR1-ROR2 complex, wherein the complex includes a ROR1 protein and a ROR2 protein. (ii) The compound is allowed to inhibit the interaction between the ROR1 protein and the ROR2 protein, thereby inhibiting a ROR1-ROR2 interaction (e.g., the formation or maintenance of a protein complex comprising ROR1 and ROR2).

The agents identified herewith may be, inter alia, useful for the treatment of cancer. Thus, in another aspect, a method of treating cancer in a subject in need thereof is provided. The method includes administering to a subject a therapeutically effective amount of an antibody, small molecule, peptide or nucleic acid identified by a method provided herein including embodiments thereof.

"Patient" or "subject in need thereof" refers to a living organism suffering from or prone to a disease or condition that can be treated by administration of a composition or pharmaceutical composition as provided herein. Non-limiting examples include humans, other mammals, bovines, rats, mice, dogs, monkeys, goat, sheep, cows, deer, and other non-mammalian animals. In embodiments, a patient is human.

The terms "disease" or "condition" refer to a state of being or health status of a patient or subject capable of being treated with a compound, pharmaceutical composition, or method provided herein. In embodiments, the disease is cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma).

The terms "treating", or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, include prevention of an injury, pathology, condition, or disease. In embodiments, "treating" refers to treatment of cancer.

An "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "therapeutically effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances, and the like., that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

By "co-administer" it is meant that a composition described herein is administered at the same time, just prior to, or just after the administration of one or more additional therapies. The compound of the invention can be administered alone or can be co-administered to the patient. Co-administration is meant to include simultaneous or sequential administration of the compound individually or in combination (more than one compound or agent). Thus, the preparations can also be combined, when desired, with other active substances (e.g. to reduce metabolic degradation).

The compositions disclosed herein can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions disclosed herein can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao Pharm. Res. 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions can also be delivered as nanoparticles.

Pharmaceutical compositions may include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule, and/or reducing, eliminating, or slowing the progression of disease symptoms.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

III. Examples

The following examples illustrate certain specific embodiments of the invention and are not meant to limit the scope of the invention.

Embodiments herein are further illustrated by the following examples and detailed protocols. However, the examples are merely intended to illustrate embodiments and are not to be construed to limit the scope herein. The contents of all references and published patents and patent applications cited throughout this application are hereby incorporated by reference.

We surprisingly show herewith that CLL cells express ROR2 coupled with ROR1, apparently in response to Wnt5a, which we found present at relatively high levels in the plasma of patients with CLL. When cultured in media lacking Wnt5a, the ROR1-ROR2 complex dissociated, but could be re-formed by treatment with Wnt5a, which induced recruitment of GEFs and the activation of RhoA and Rac1. Activation of RhoA was associated with enhanced chemokine-induced migration, whereas activation of Rac1 was associated with enhanced leukaemia-cell proliferation in response to membrane-bound CD154 and IL-4/10. Inhibiting expression of either ROR1 or ROR2 impaired the capacity of Wnt5a to enhance chemotaxis, as could treatment with UC-961. The dependency on coupling ROR2 with ROR1 to achieve optimal non-canonical Wnt signaling also was observed with MEC1 cells, a CLL-cell line that expresses Wnt5a and ROR2, but lacks expression of ROR1. Transfection of MEC1 to express ROR1 allowed for its coupling with ROR2, which was associated with recruitment of GEFs, greater activation of RhoA and Rac1, enhanced cellular chemokine-directed migration, and enhanced growth relative to that of parental MEC1 cells; such changes could be inhibited by treatment with UC-961 or neutralizing antibodies to Wnt5a. Collectively, our studies indicate that neither ROR1 nor ROR2 is sufficient to allow for Wnt5a-induced activation of RhoA or Rac1, countering the widely-held notion that each could serve independently as a receptor for Wnt5a to induce non-canonical Wnt signaling[27,31-33].

We found the KNG domain was required for ROR1 to couple with ROR2. KNG domains contain intra-domain disulfide bridges, which define polypeptide loops that often are involved in protein-protein interactions[34]. As such, the KNG domain of ROR1, and possibly ROR2, may interact with one another to form a heterodimeric complex in response to Wnt5a (e.g. FIG. 5I). Although the failure of the ΔKNG-ROR1 to couple with ROR2 also could be due to steric constraints introduced by truncation of the ROR1 extracellular domain, ΔCRD-ROR1, lacking the larger extra-cellular CRD, could couple with the ROR2. Because the CRD is the putative site for Wnt binding[35,36], Wnt5a binding to ROR2 may be sufficient to allow for ROR2 to couple with ROR1. Alternatively, the CRD may have residues that ordinarily inhibit such coupling unless bound to Wnt5a. In any case, neither ΔCRD-ROR1 nor any one of the other truncated forms of ROR1 allowed for recruitment of GEFs to ROR1-ROR2 or enhanced activation of RhoA and Rac1 in transfected MEC1 cells. Because each of the truncated forms of ROR1, except for ΔKNG-ROR1, allowed for ROR1 to complex with ROR2, the coupling of ROR1 with ROR2 does not appear sufficient for Wnt5a-induced non-canonical signaling. Moreover, the intracellular domains of ROR1 appear necessary, including the proline-rich domain (PRD), which contains several putative SH3-binding sites, which may permit docking of GEFs and/or scaffolding proteins to the ROR1-ROR2 complex. That ΔPRD-ROR1 did not allow for recruitment of GEFs to the ROR1-ROR2 complex implies that the PRD domain of ROR2 is not sufficient to recruit such factors, or to induce enhanced activation of RhoA or Rac1 in response to Wnt5a.

These observations define a model that may explain some apparent divergent attributes of ROR2 or Wnt5a in development or neoplasia. Although largely overlapping, the developmental tissue-expression of ROR2 is not entirely congruous with that of ROR1, but appears more broadly distributed. Conceivably only cells that co-express both ROR1 and ROR2 during development have enhanced non-canonical Wnt signaling in response to Wnt5a; loss of ROR1 could thus serve as a developmental switch, allowing cells to escape the influence of Wnt5a on the activation of Rho GTPases. This also might explain how ROR2 or Wnt5a may suppress canonical Wnt signaling in development and/or act as tumour suppressors. Like MEC1, cells may require co-expression of both ROR1 and ROR2 to trigger optimal Wnt5a-induced activation of RhoA and Rac1. In the absence of ROR1, Wnt5a instead may induce ROR2 to bind other Frizzled (Fzd) receptors[37-39] which otherwise couple with LRP5/6 in response to canonical Wnt factors, such as Wnt3a[27,32,38,39]. Conceivably, ROR2/Fzd complexes may compete with the formation of LPR/Fzd complexes, thereby inhibiting the capacity of other Wnt factors to induce canonical Wnt signaling[27,32,38,39]. Moreover, the capacity of ROR2 or Wnt5a to act as tumour/growth-suppressors versus tumour/growth-promoters may depend in part upon the relative expression of ROR1, LPR5/6, and Fzd receptors, which can couple with ROR2 in response to Wnt5a.

ROR2 appears more widely expressed on post-partum tissues than ROR1, which appears confined to a rare subpopulation of precursor B cells, called hematogones[14]. In this study, we found ROR2 on normal CD5 B cells, which are the presumed normal counterpart to CLL40. Conceivably, acquisition of ROR1 by such cells may be an important step in leukaemogenesis, allowing the neoplastic B cells to activate RhoA and Rac1 in response to Wnt5a, which we found at relatively high-levels in the plasma of patients with CLL. We found that treatment of CLL cells with the anti-ROR1 mAb, UC-961, could disrupt the coupling of ROR1 with ROR2 and interfere with activation Rho GTPases in response to Wnt5a, thereby abrogating the capacity of Wnt5a to enhance chemokine-induced migration or CD154-induced-proliferation. Similarly, UC-961 eliminated the advantages that MEC1-ROR1 cells had over parental MEC1 cells in proliferation or chemokine-induced migration in vitro, or engraftment of immune-deficient mice in vivo.

Example 1—Wnt5a Enhances CLL Proliferation and Migration

Figure 7:
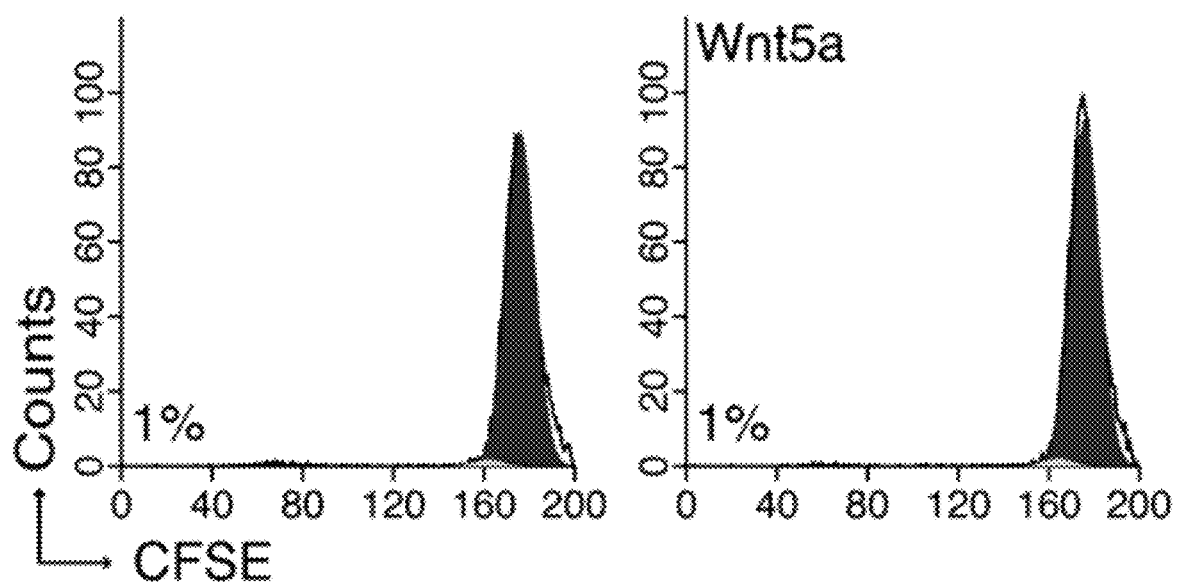
FIG. 7. CFSE assay for CLL proliferation induced by Wnt5a without CD154. Fluorescence of CFSE-labeled CLL cells (n=6) co-cultured for 6 days with HeLa cells without (left panel) or with (right panel) exogenous Wnt5a. The results of assays on one representative CLL sample are shown with the percent of dividing cells indicated in the lower left of each panel.

CLL cells can be induced to proliferate upon culture with cells expressing CD154 (HeLa$_{CD154}$) in the presence of exogenous interleukin (IL)-4 and IL-10 (FIG. 1a, b). Addition of exogenous Wnt5a significantly enhanced the proportion of dividing cells and the numbers of cell divisions that could be deduced from the fluorescence of cells labeled with carboxyfluorescein succinimidyl ester (CFSE); the enhanced proliferation induced by Wnt5a could be inhibited by an anti-ROR1 mAb (UC-961) to levels comparable to those observed in cultures without Wnt5a (FIG. 1a, b). CLL cells co-cultured with HeLa cells were not induced to proliferate, even in the presence of IL-4/10 and/or Wnt5a (FIG. 7).

Figure 1C:
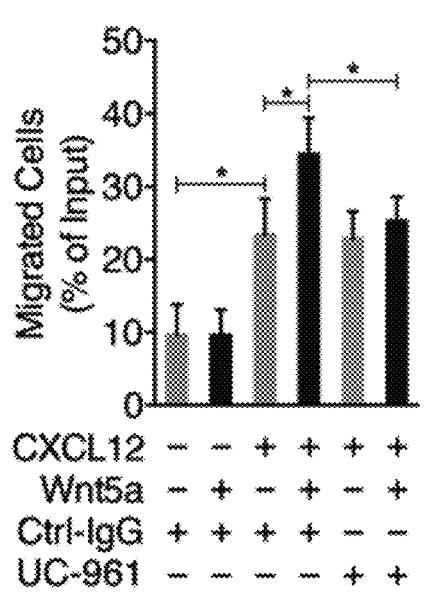

We confirmed that exogenous Wnt5a also could enhance migration of CLL cells toward chemokines, e.g. CXCL12 (FIG. 1c) [41]. The capacity of Wnt5a to enhance migration could be inhibited by UC-961. However, exogenous Wnt5a without CXCL12 did not induce CLL-cell migration, and UC-961 did not inhibit the migration of CLL cells to CXCL12 without Wnt5a (FIG. 1c).

Figure 1D:
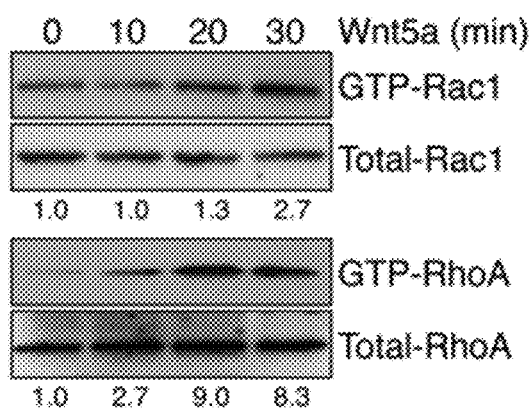
Figure 1E:
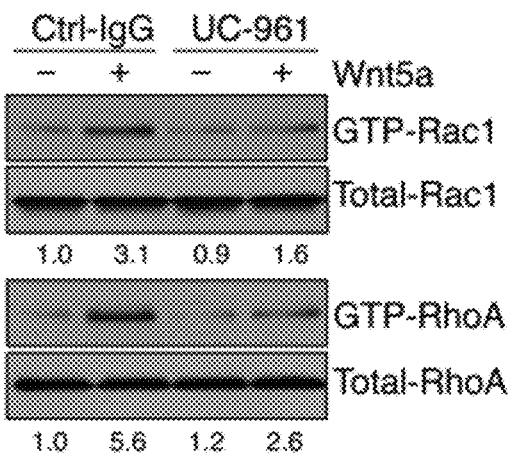
Figure 1F:
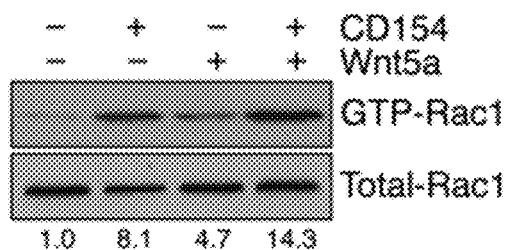
Figure 1G:
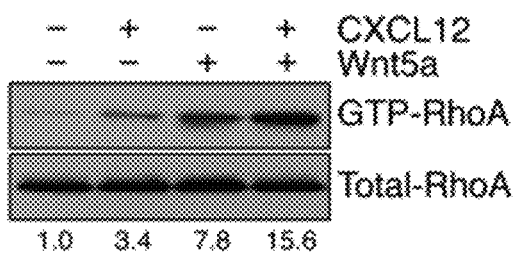
Figure 1H:
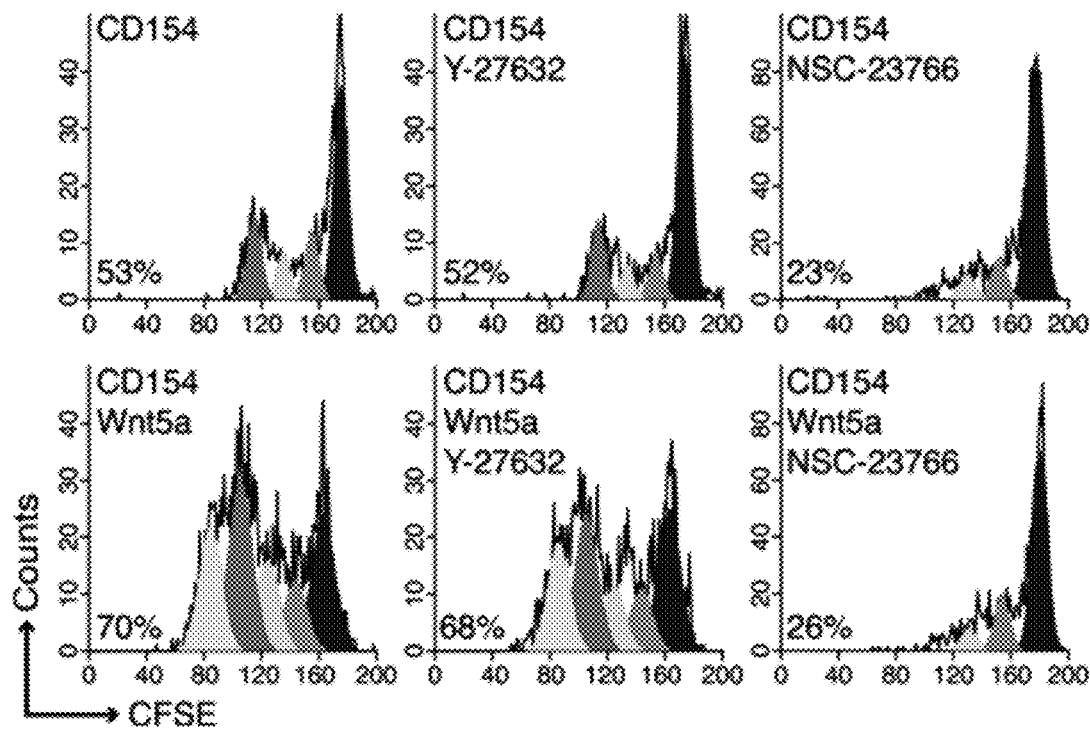
Figure 1I:
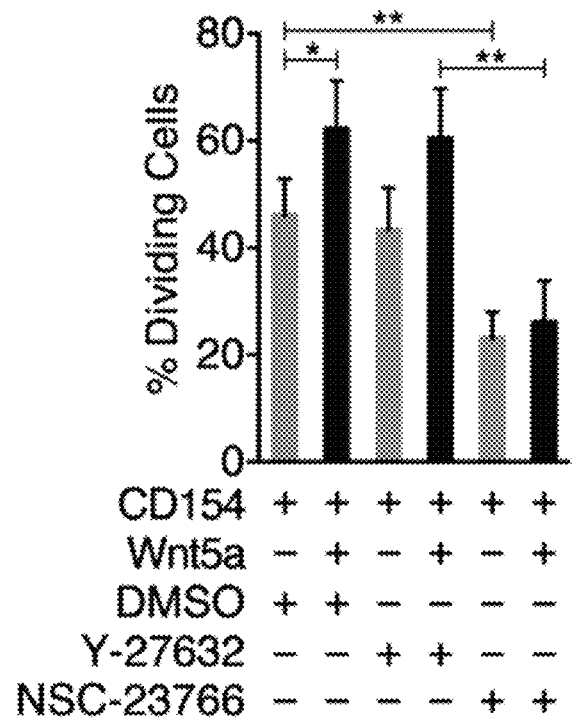
Figure 1J:
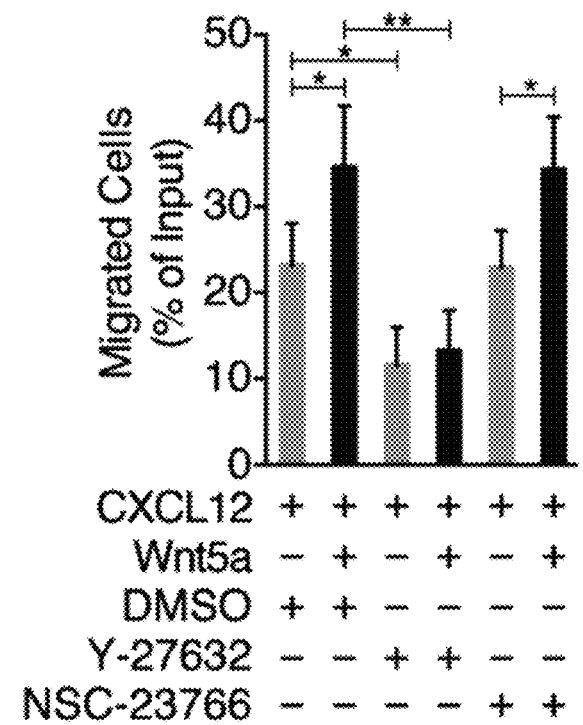

Rho family proteins play important roles in regulating proliferation and/or migration [42], and Wnt5a has been reported to activate Rac1 and RhoA in other cell types [38,43]. We observed that Wnt5a could induce activation of Rac1 and RhoA within 30 min (FIG. 1d). Addition of UC-961 could inhibit Wnt5a-induced activation of Rac1 and RhoA (FIG. 1e). Co-culture of CLL cells with HeLa$_{CD154}$, but not HeLa cells, also induced activation of Rac1 (FIG. 1f). Also, CXCL12 activated RhoA in CLL cells (FIG. 1g) [44]. In each case, exogenous Wnt5a enhanced the level of Rac1 or RhoA activated by CD154 or CXCL12, respectively (FIG. 1f, g). NSC-23766, an inhibitor of Rac1 GTPase, but not Y-27632, a selective inhibitor of p160ROCK, could inhibit the proliferation induced by HeLa$_{CD154}$, with or without exogenous Wnt5a. On the other hand, Y-27632, but not NSC-23766, could inhibit chemotaxis to CXCL12, with or without exogenous Wnt5a, supporting the notion that activation of Rac1 or RhoA can promote CLL-cell proliferation or migration, respectively (FIG. 1h-j).

Example 2—Detection of ROR2 on CLL and CD5 B Cells

Figure 2A:
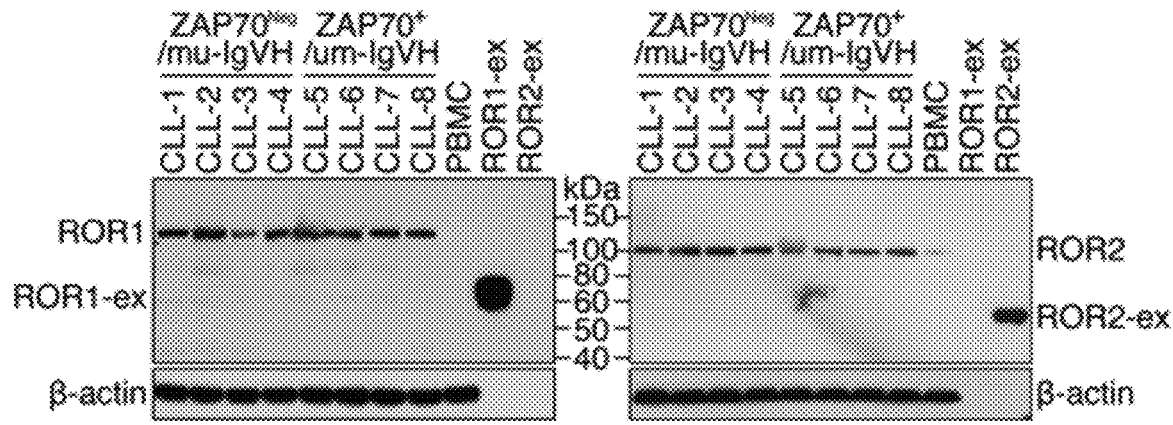
FIGS. 2A-2G. ROR1 couples with ROR2.
Figure 2B:
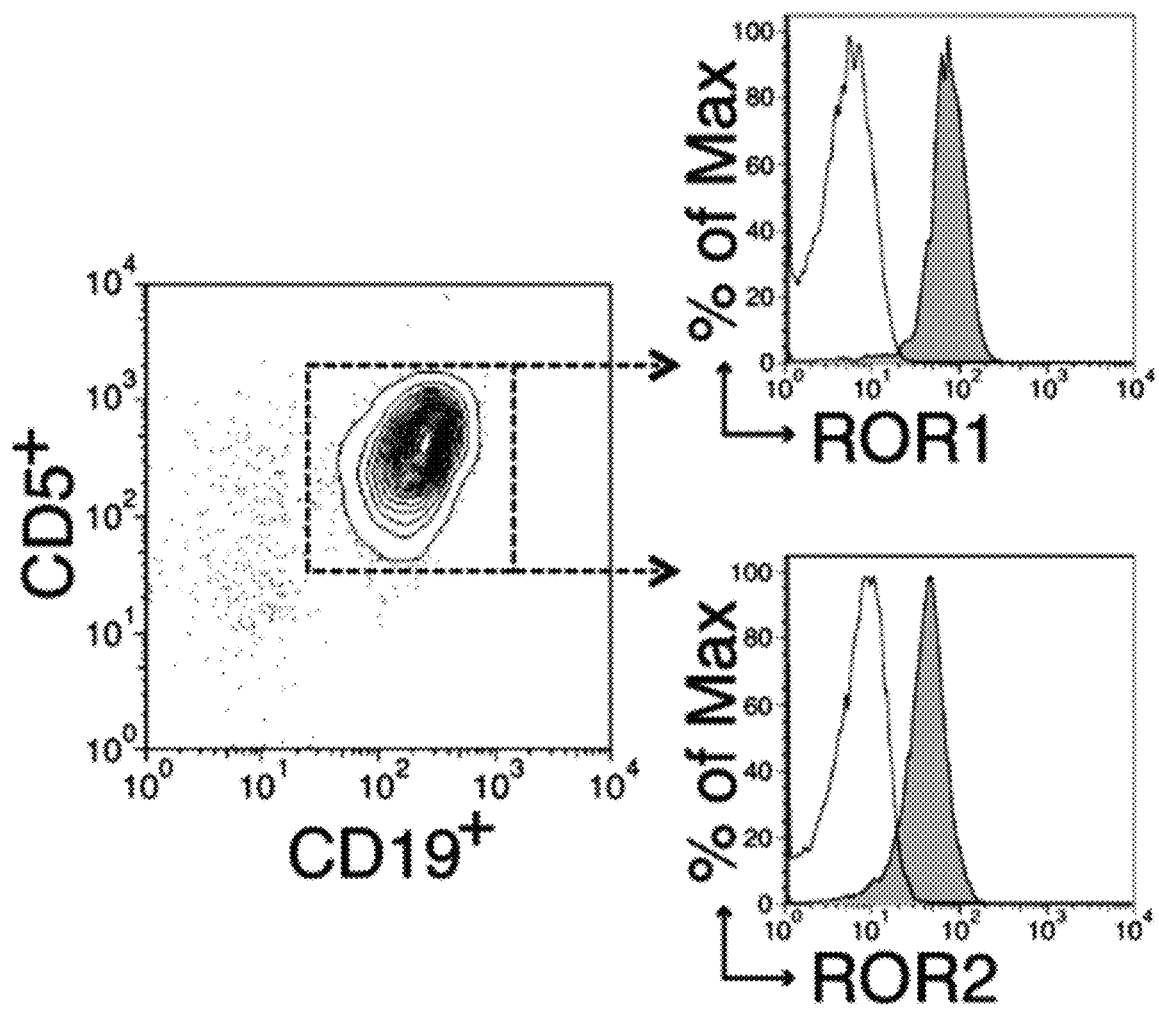
Figure 8A:
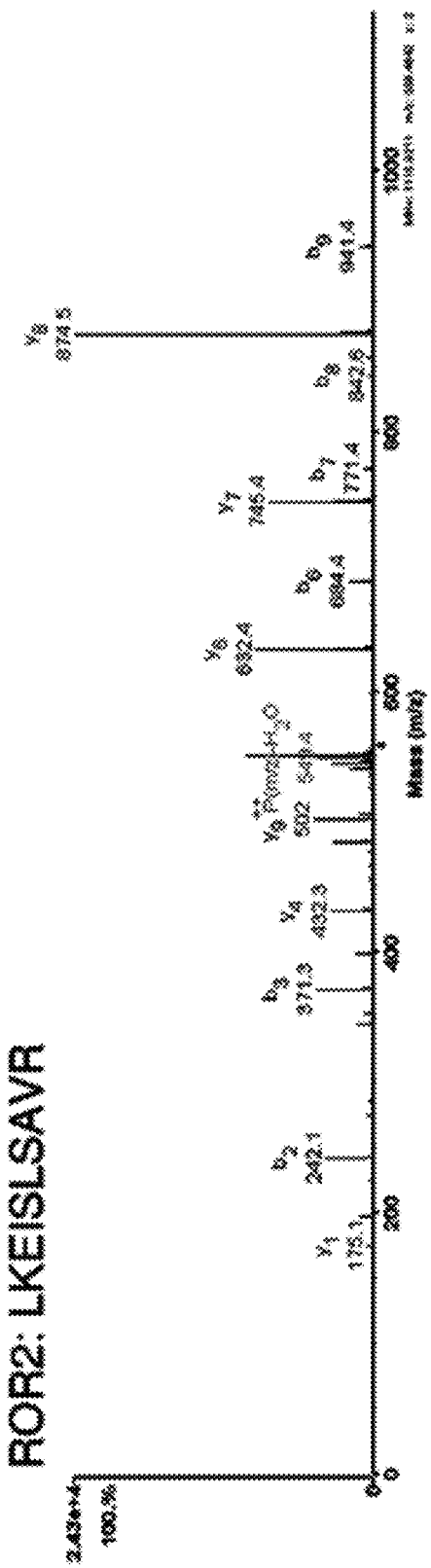
FIGS. 8A-8E. ROR2 expression in CLL cells.
Figure 8B:
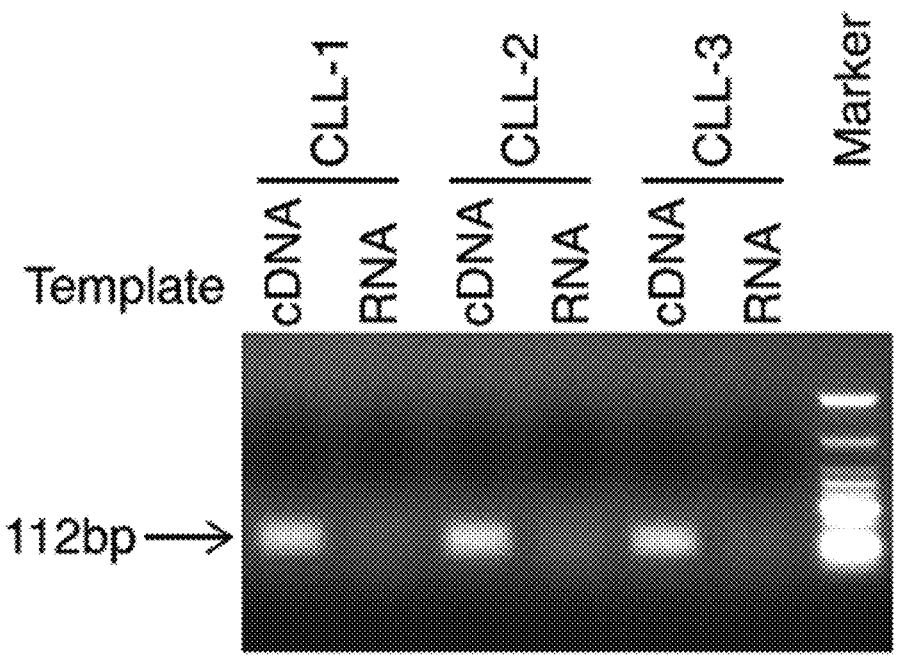
Figure 8B:
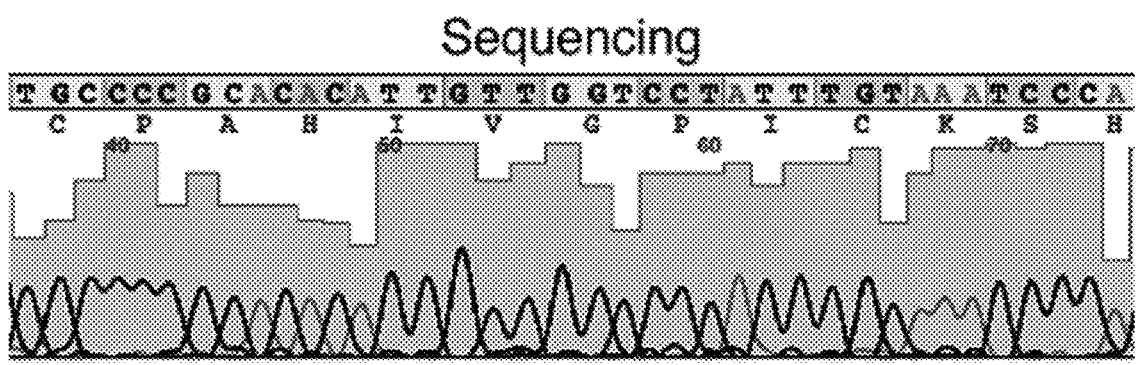
Figure 8C:
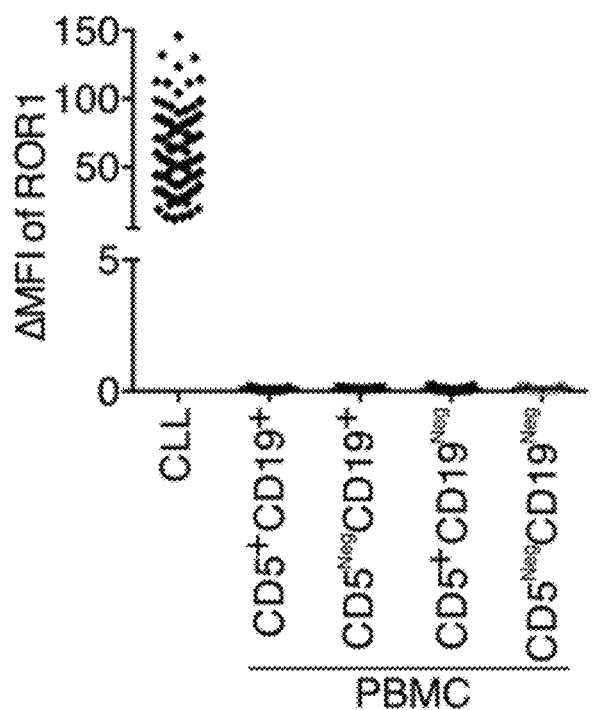
Figure 8D:
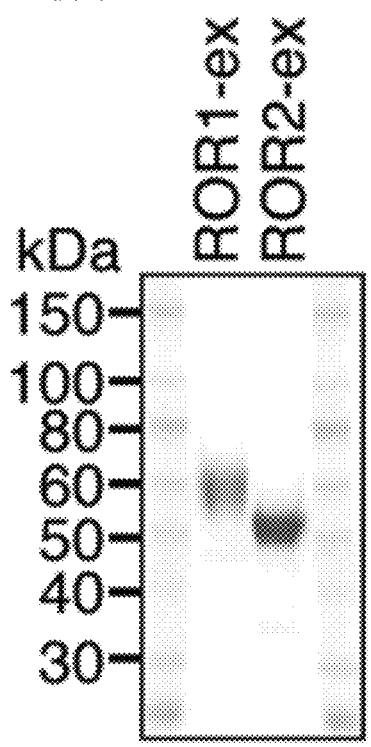
Figure 8E:
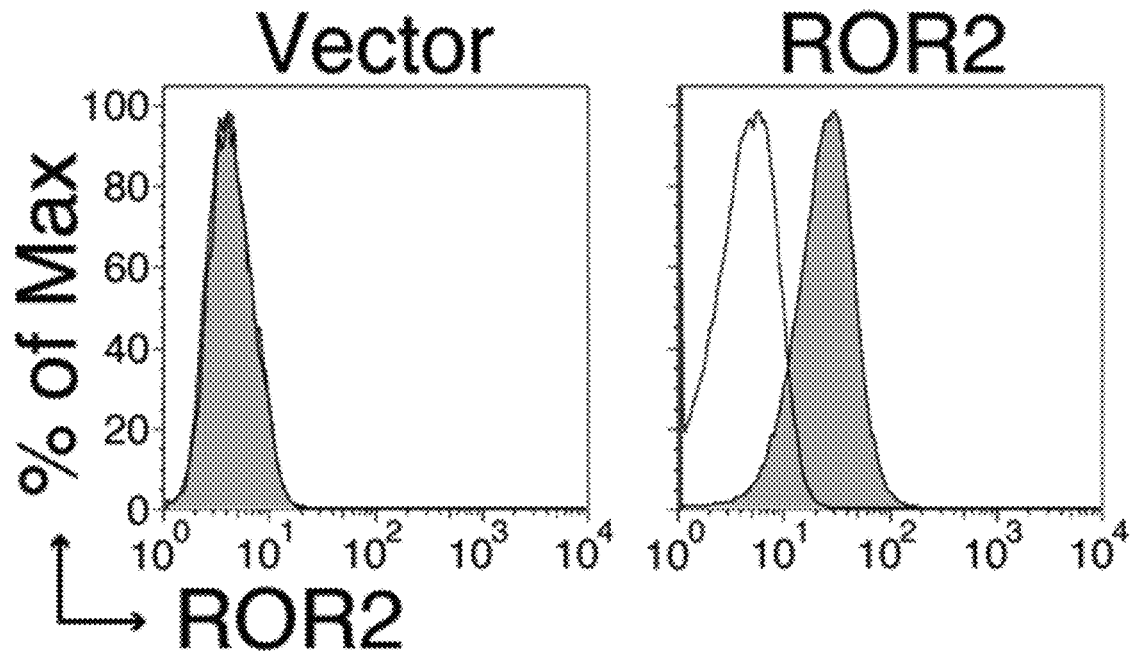

We performed mass spectrometry-based proteomic analysis on anti-ROR1 immune precipitates (ip) of CLL-cell lysates. Surprisingly, we detected ROR2 in addition to ROR1 (FIG. 8A). Detecting ROR2 was unexpected, as one group reported CLL cells specifically lacked expression of ROR2 [17]. However, we detected ROR2 mRNA in isolated CLL cells (FIG. 8B), and both ROR1 and ROR2 in all samples examined by immunoblot analysis (FIG. 2a). Surface expression of both proteins also was detected on CD5$^+$CD19$^+$ CLL cells via flow cytometry (FIGS. 2B, 2D and 8C).

Figure 2C:
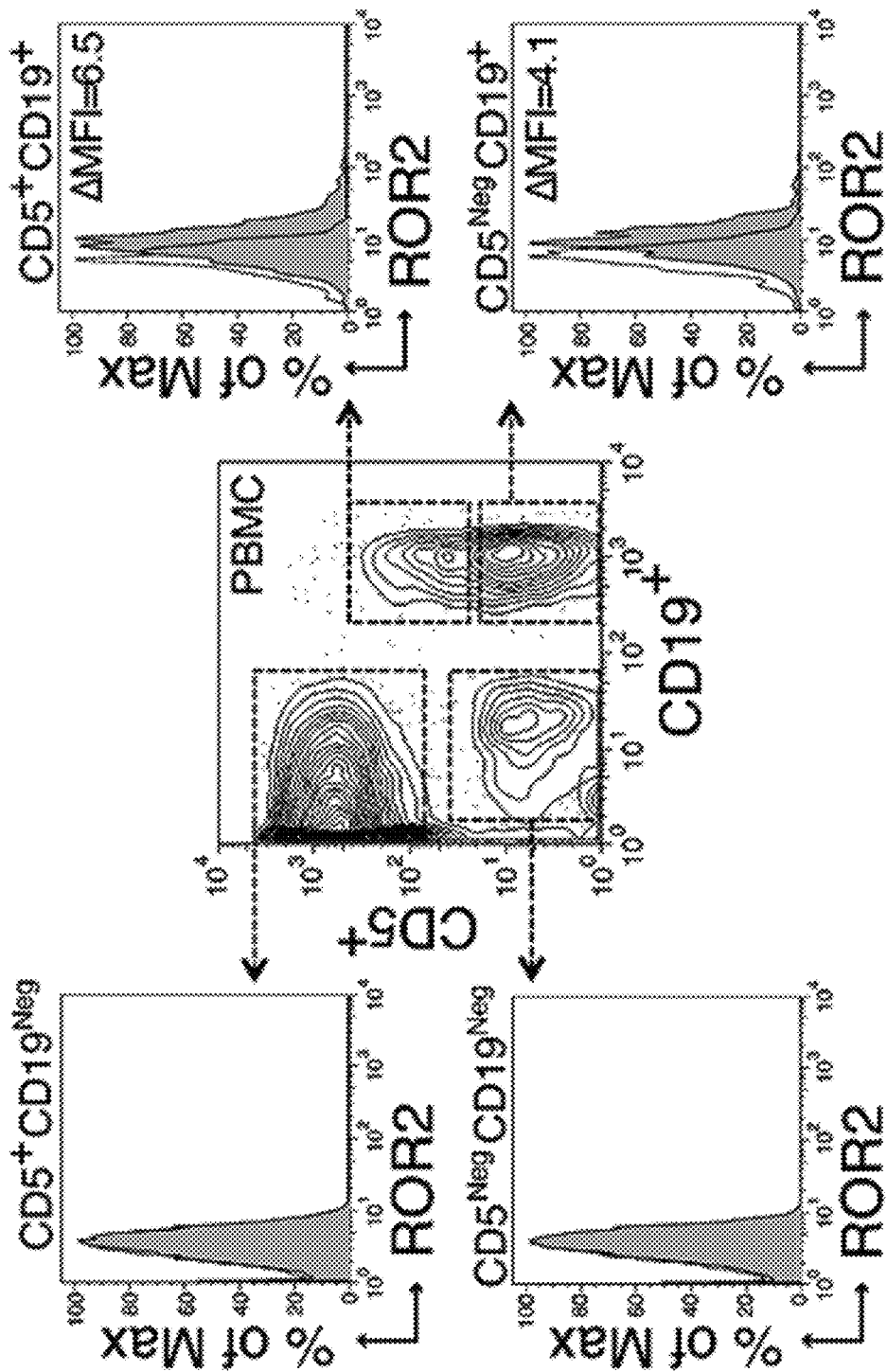
Figure 2D:
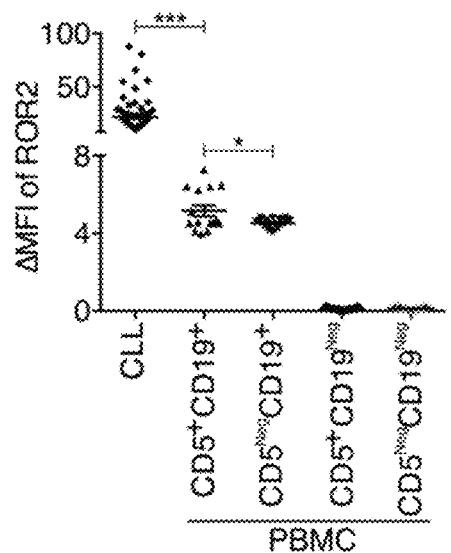

We found that CD19$^+$ blood B cells of healthy adults also expressed ROR2, including B cells that co-expressed CD5 (FIG. 2c). We subtracted the mean-fluorescence intensity (MFI) of cells stained with a fluorochrome-labeled, isotype-control mAb from the MFI of cells stained with anti-ROR2 to determine the ΔMFI. The mean ROR2 ΔMFI in CD5$^+$CD19$^+$ B cells of healthy subjects, 5.1±0.3 (n=15), was higher than that of CD5$^{Neg}$CD19$^+$ B cells, 4.5±0.1, but still significantly lower than the mean ROR2 ΔMFI□for CLL cells (21.8±1.8, n=80) (FIG. 2d). We did not detect ROR2 on CD19$^{Neg}$ blood lymphocytes (FIG. 2c, d) or ROR1 on the mononuclear cells of healthy donors (FIG. 8C).

Figure 2E:
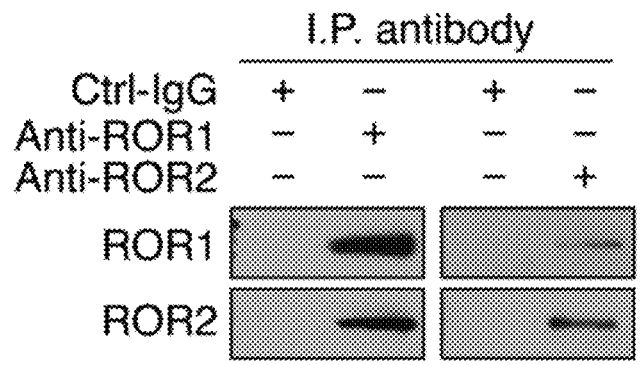
Figure 2F:
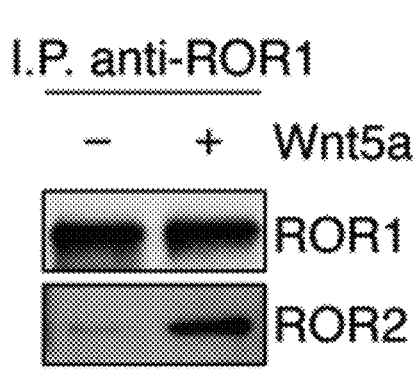
Figure 2G:
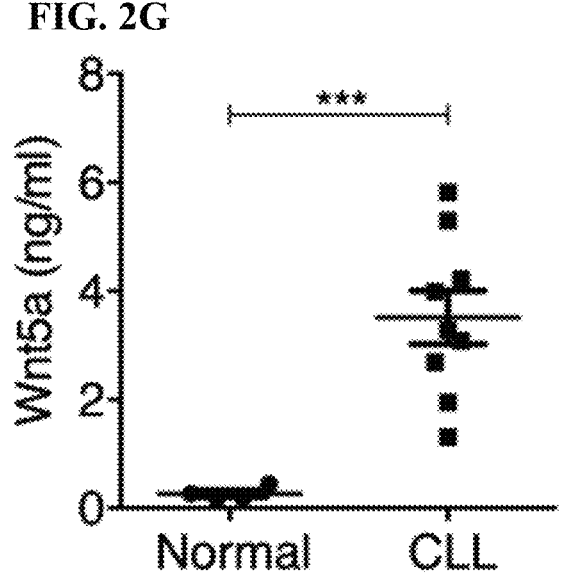

Immunoblot analysis of anti-ROR1 or anti-ROR2 ip confirmed that ROR1 was coupled with ROR2 in freshly-isolated CLL cells (FIG. 2e); however, the coupling of ROR1 with ROR2 was less apparent in CLL cells cultured in Wnt5a-deficient media, unless they were treated with exogenous Wnt5a (FIG. 2O. This indicates that ROR1 already was coupled with ROR2 on CLL cells in vivo, probably in response to endogenous Wnt5a. Consistent with this notion, we detected high-levels of Wnt5a in CLL-patient plasma relative to that of aged-matched controls (FIG. 2g).

Example 3—UC-961 Inhibits Coupling of ROR1 with ROR2

Figure 3A:
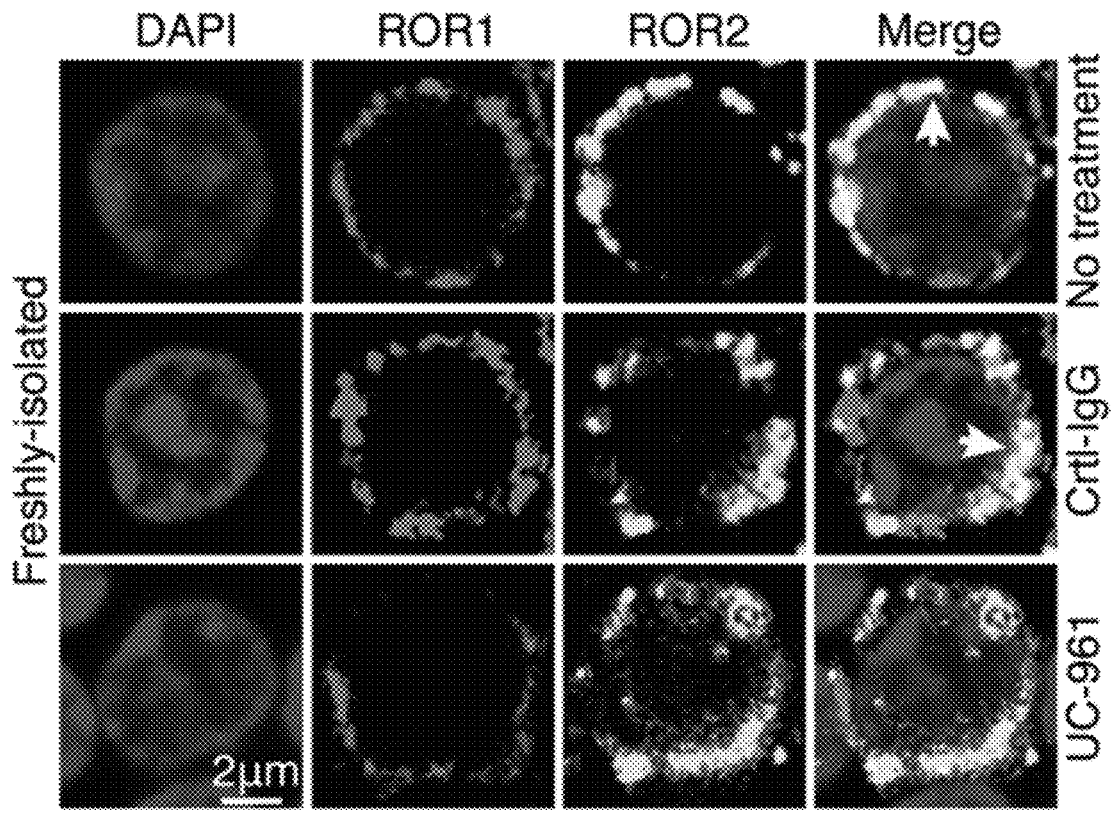
FIGS. 3A-3D. UC-961 inhibits ROR1 signaling.
Figure 3B:
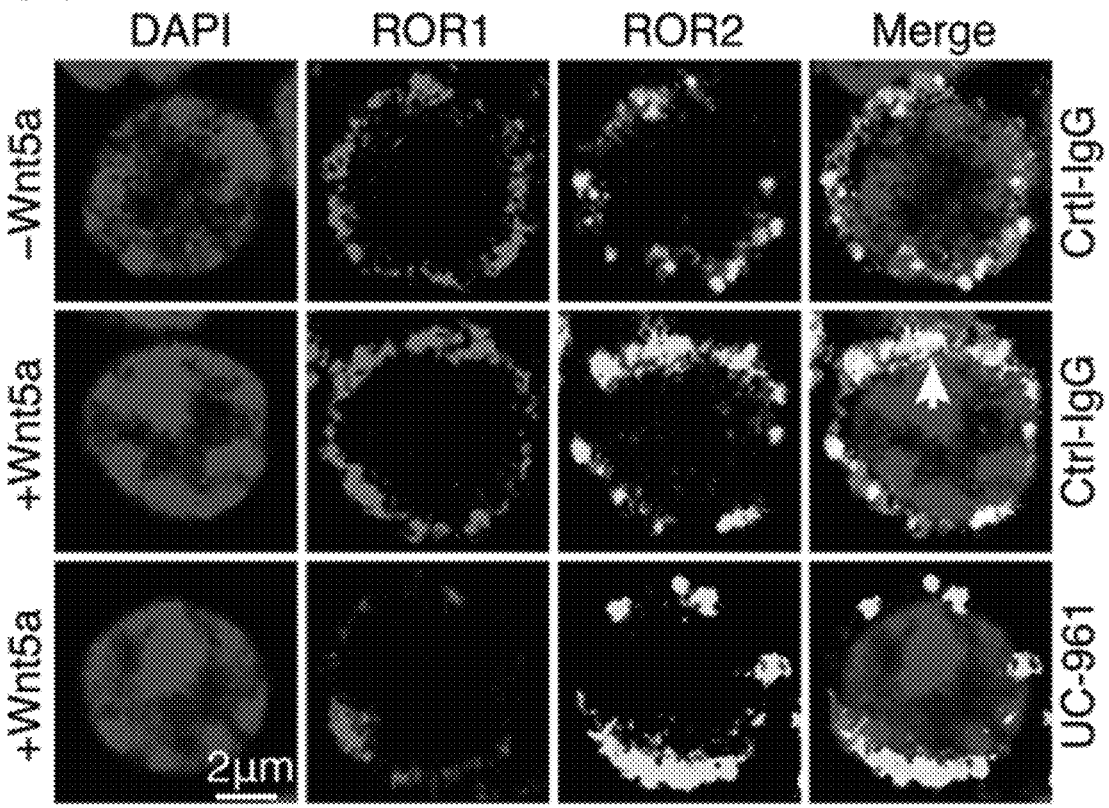
Figure 9:
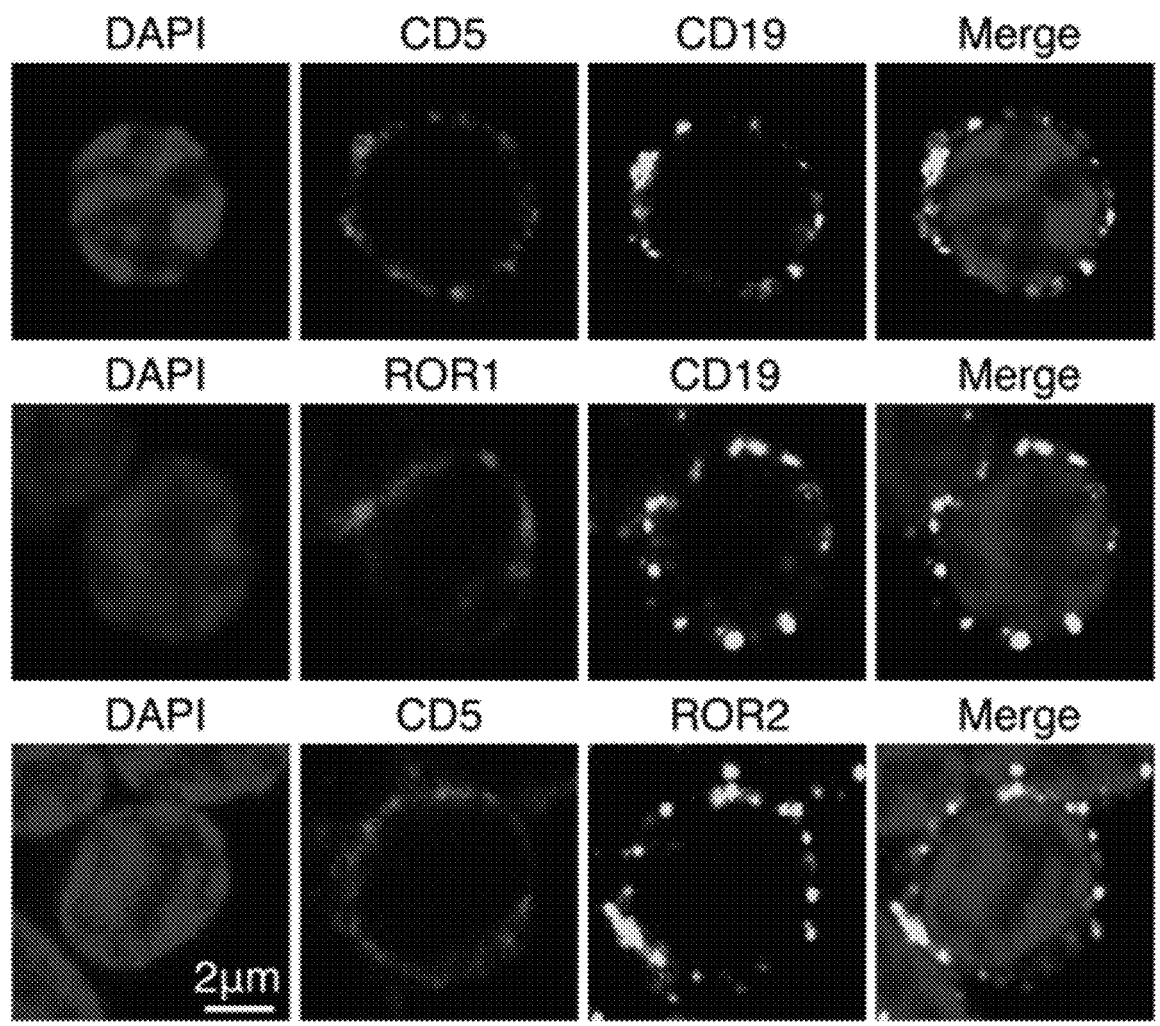
FIG. 9. Negative control for co-localization analysis by confocal microscopy. CLL cells were stained with anti-CD5-Alexa-647 and anti-CD19-Alexa-488; anti-ROR1-Alexa-647 and anti-CD19-Alexa-488; or anti-CD5-Alexa-647 and anti-ROR2-Alexa-488 for evaluation by confocal microscopy (Scale bar: 2 μm). There is no co-localization between CD5 and CD19, ROR1 and CD19, or CD5 and ROR2.

We performed fluorescence confocal microscopy, using a non-cross-blocking mAb (4A5) specific for a ROR1 epitope distinct from that recognized by UC-961. This demonstrated that ROR1 co-localized with ROR2 in freshly-isolated CLL cells (FIG. 3a), but not with CD5 or CD19 (FIG. 9). However, it was difficult to detect co-localization of ROR1 with ROR2 in cultured CLL cells unless they were treated with exogenous Wnt5a (FIG. 3b). Incubation of freshly-isolated or Wnt5a-treated CLL cells with UC-961 apparently disrupted ROR1-ROR2 coupling, which otherwise was readily observed in freshly-isolated or Wnt5a-treated CLL cells incubated with a non-specific IgG (Ctrl-IgG) (FIG. 3a, b).

Figure 3C:
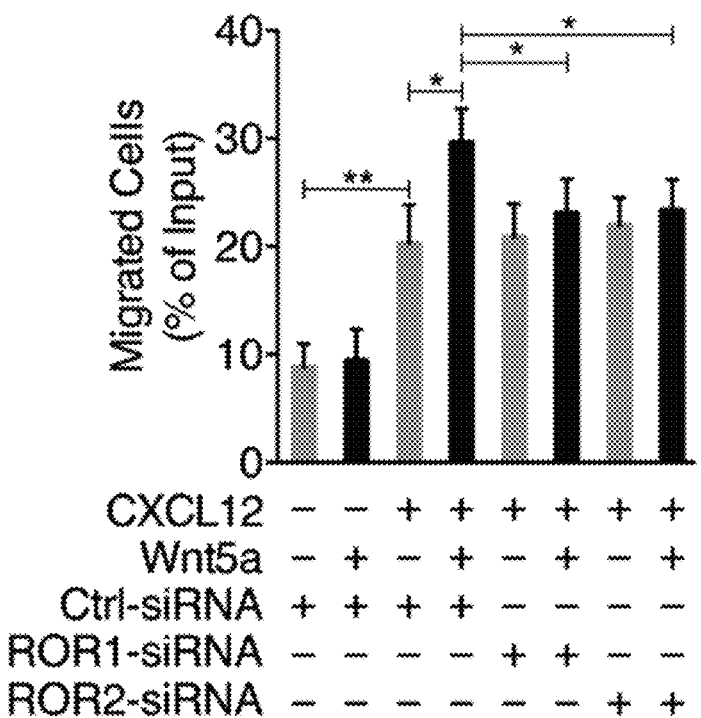
Figure 3D:
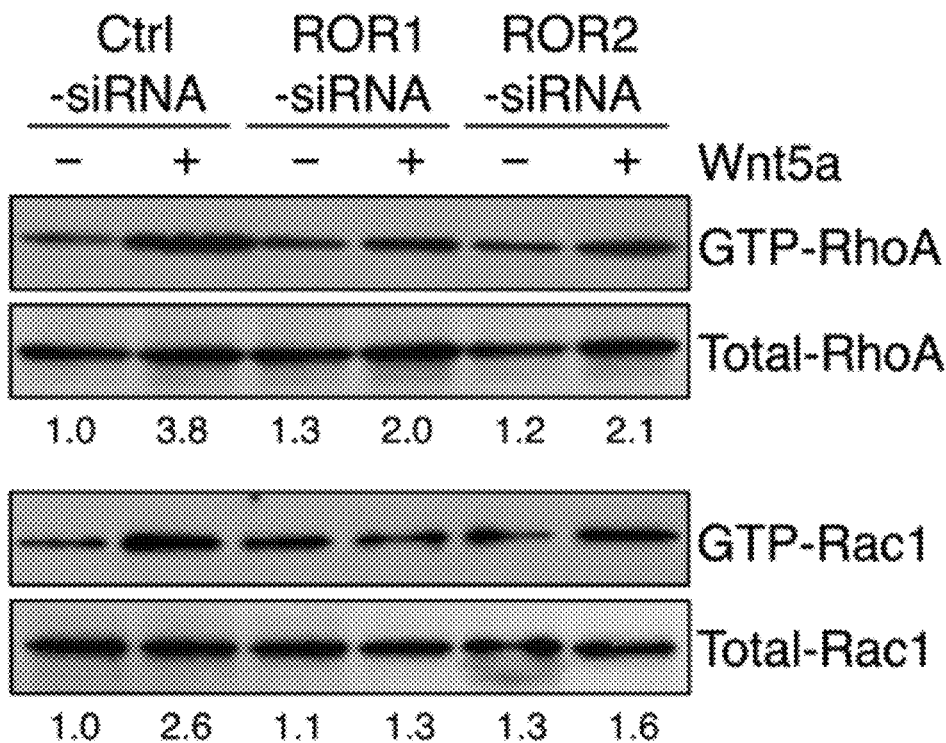
Figure 10A:
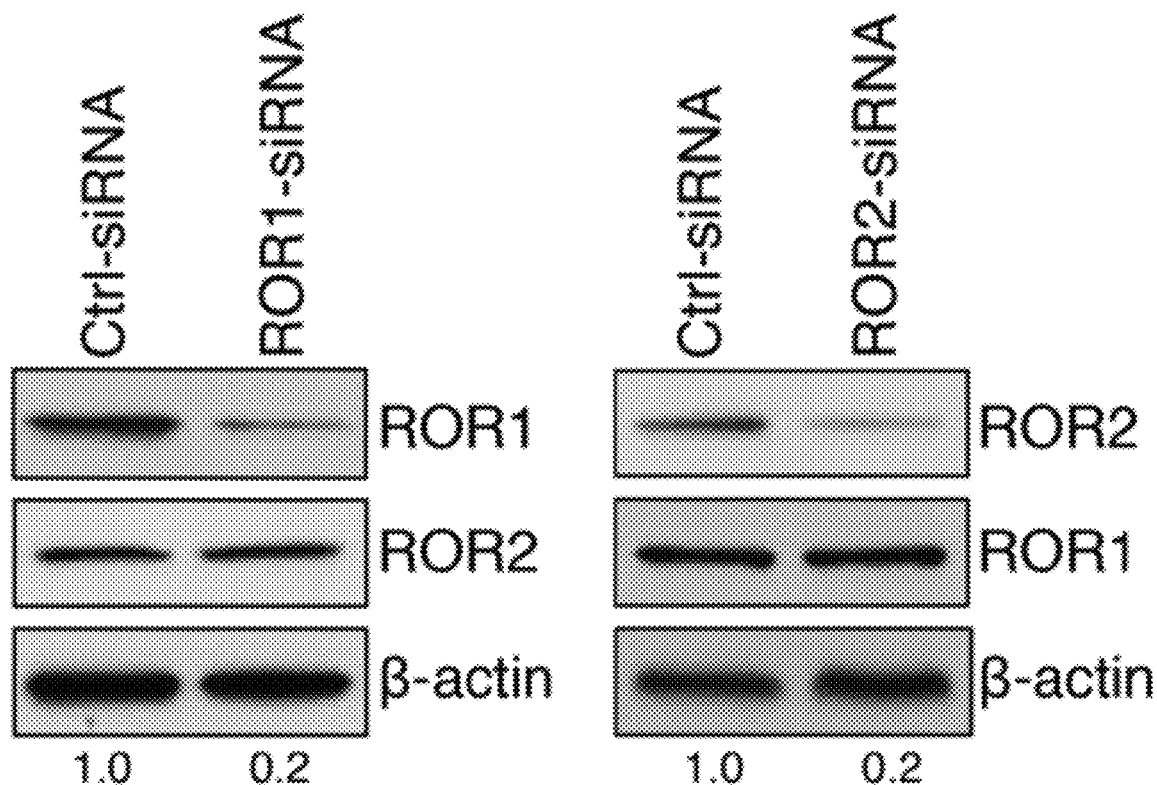
FIGS. 10A-10B. Silencing of ROR1 and ROR2 in CLL.
Figure 10B:
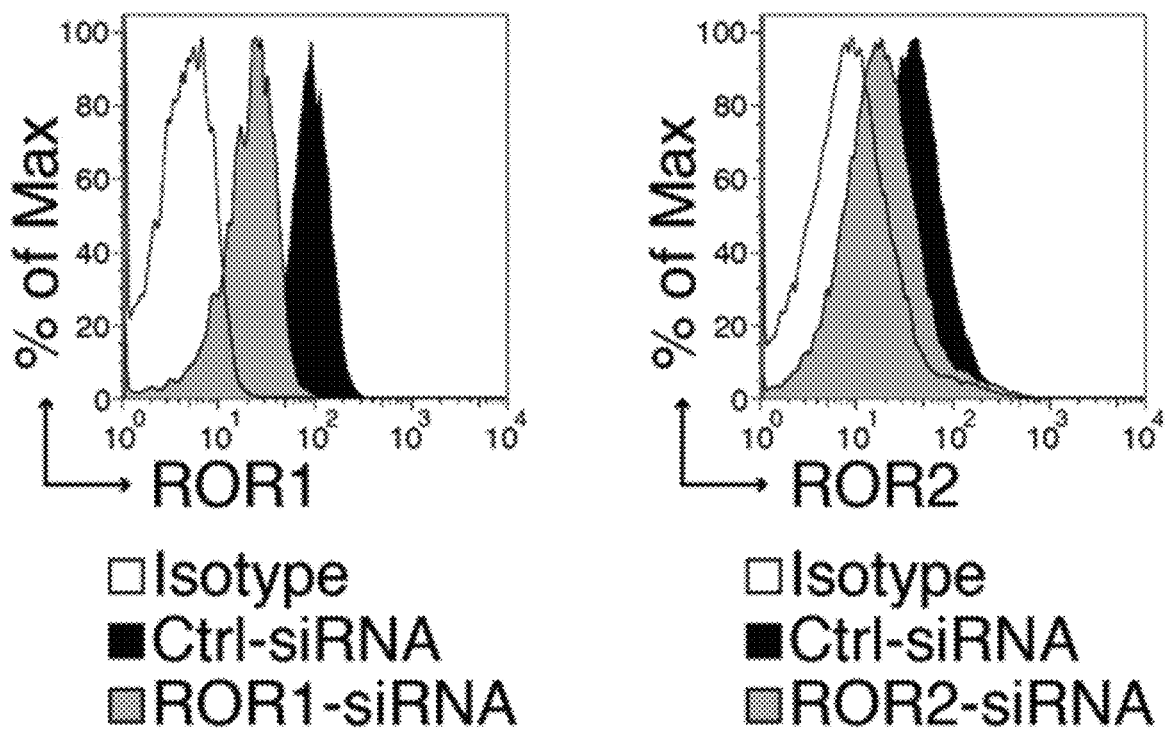

Transfecting CLL cells with siRNA specific for ROR1 or ROR2, but not control siRNA, respectively lowered expression of only ROR1 or ROR2 by immunoblot analysis or flow cytometry (FIGS. 10A-10B). Silencing either ROR1 or ROR2 inhibited the capacity of Wnt5a to enhance CLL-cell migration to CXCL12 (FIG. 3c) or to induce activation of RhoA or Rac1 (FIG. 3d), indicating that optimal Wnt5a-induced signaling was dependent on the co-expression of both ROR1 and ROR2.

Example 4—ROR1-ROR2 Complex Recruit GEFs

Figure 4A:
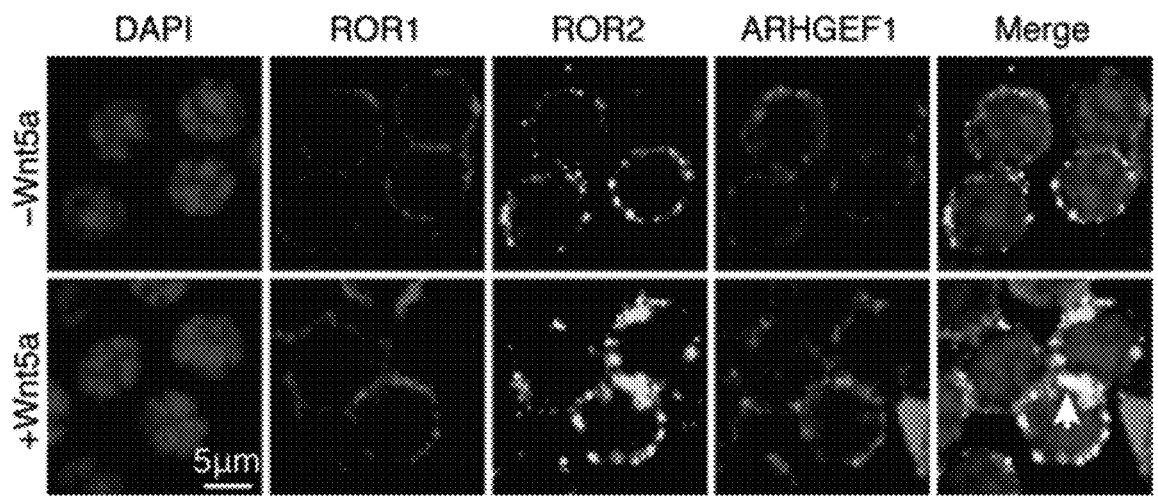
FIGS. 4A-4F. UC-961 inhibits Wnt5a-induced recruitment of GEFs and activation of RhoA and Rac1.
Figure 4B:
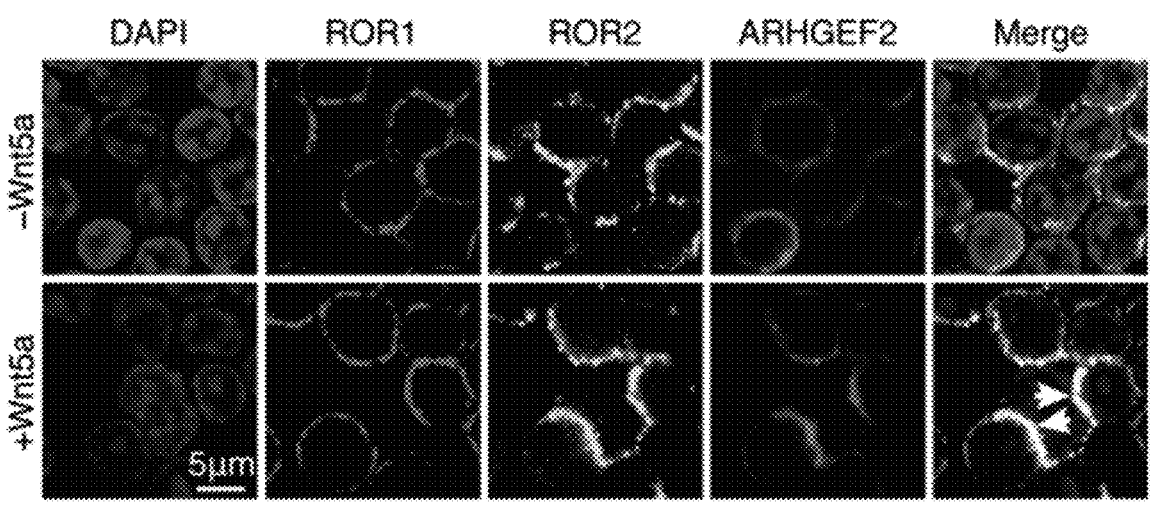
Figure 4C:
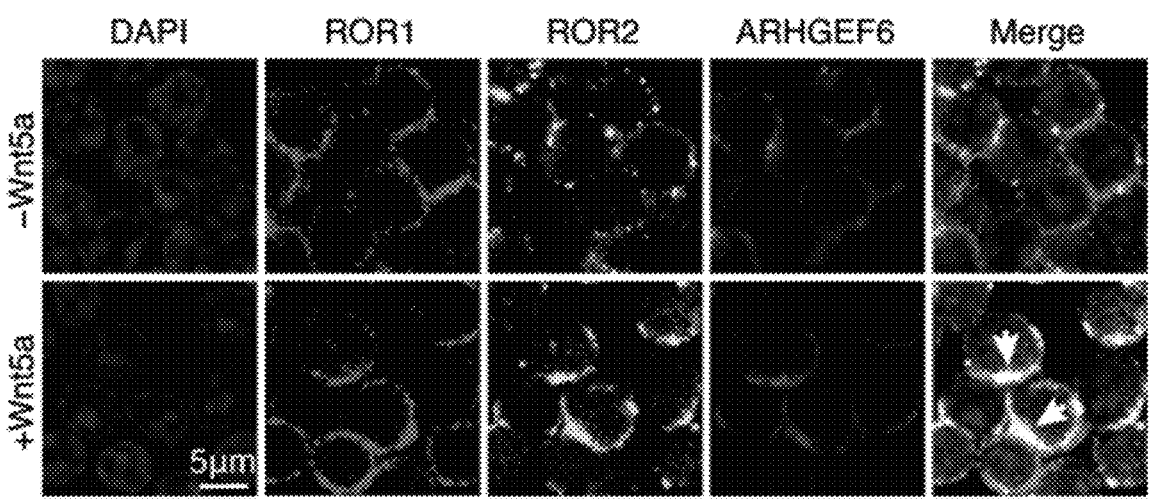
Figure 11A:
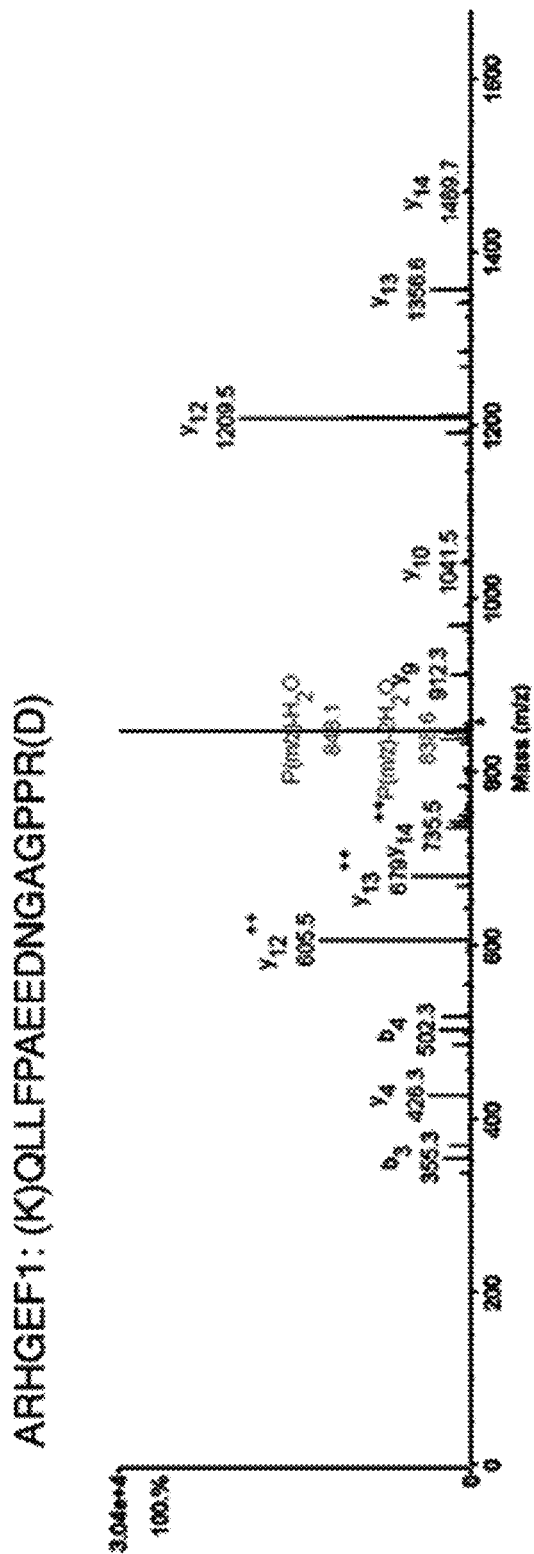
FIGS. 11A-11B. ROR1 interacts with ARHGEF1, ARHGEF2, and ARHGEF6.
Figure 11A:
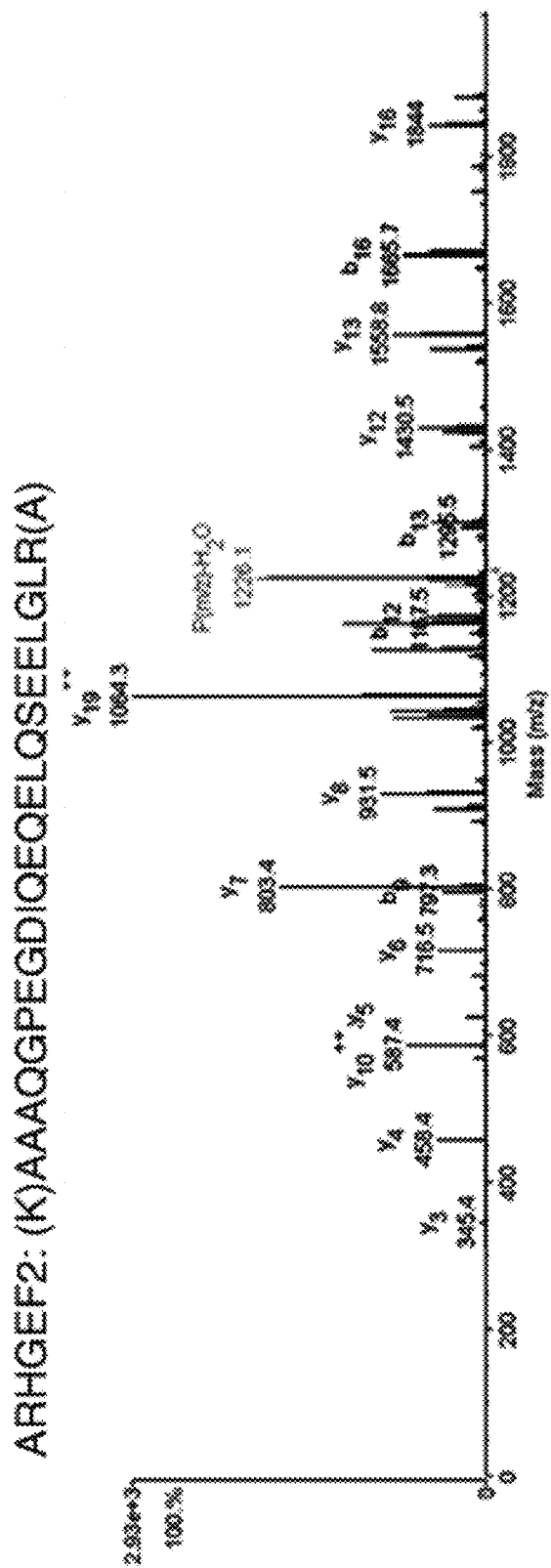
Figure 11A:
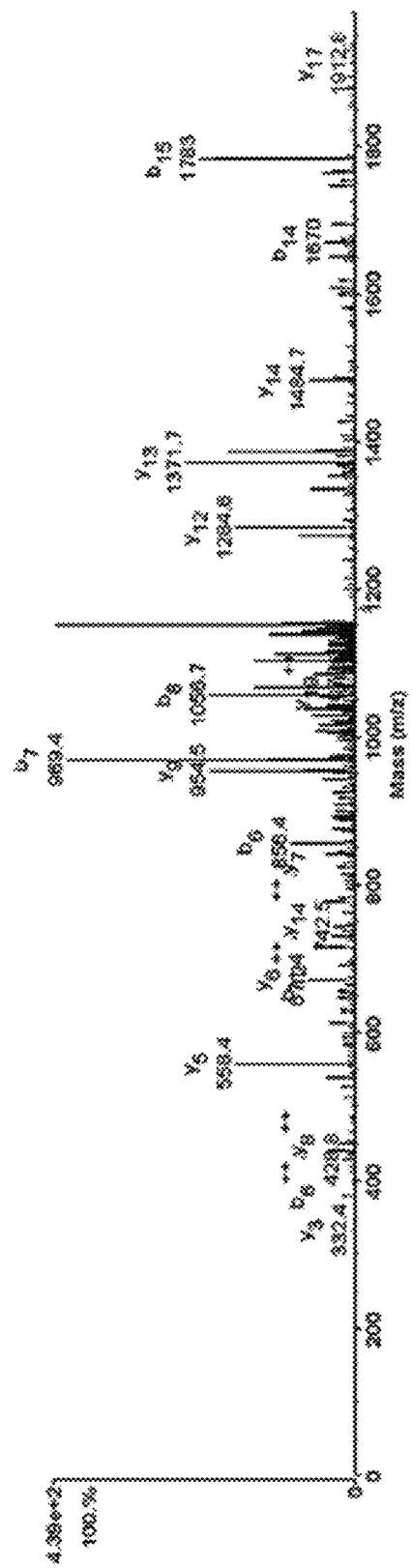
Figure 11B:
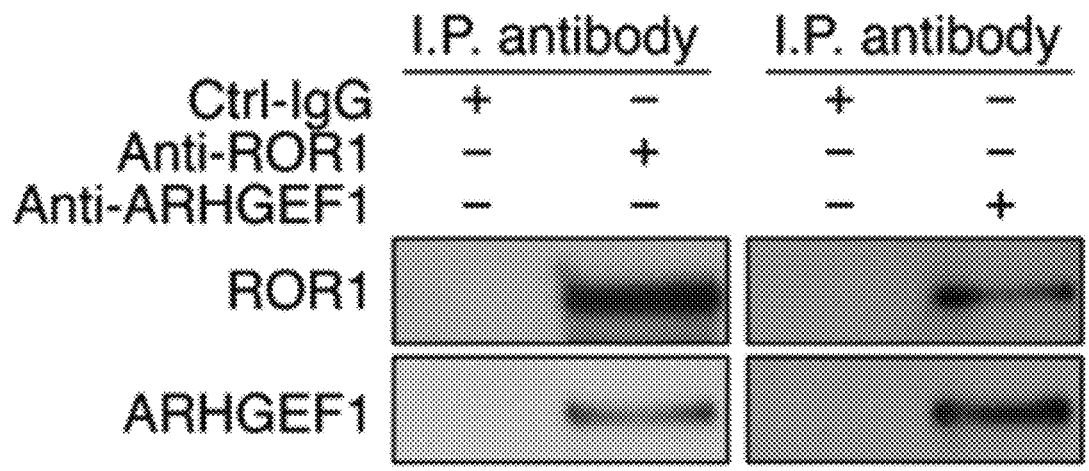
Figure 11B:
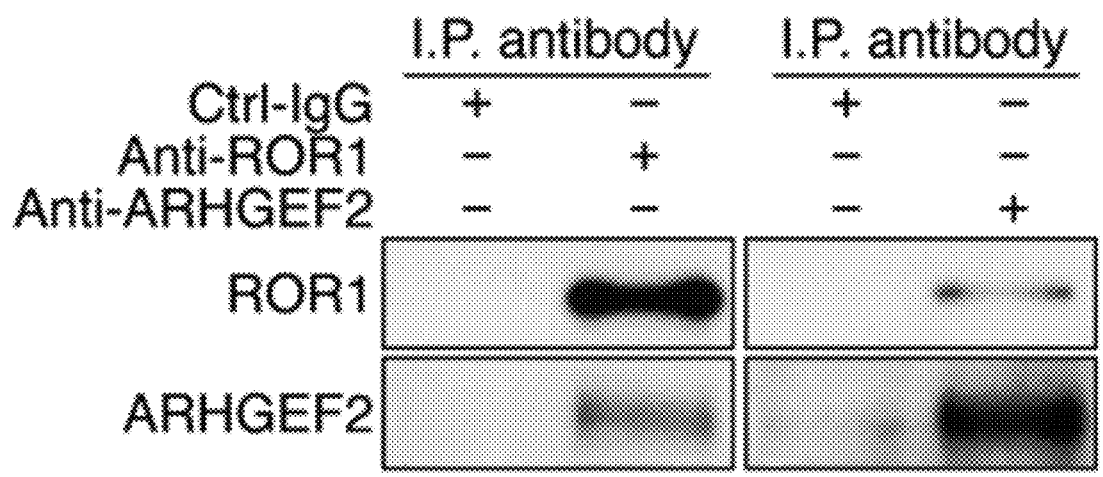
Figure 11B:
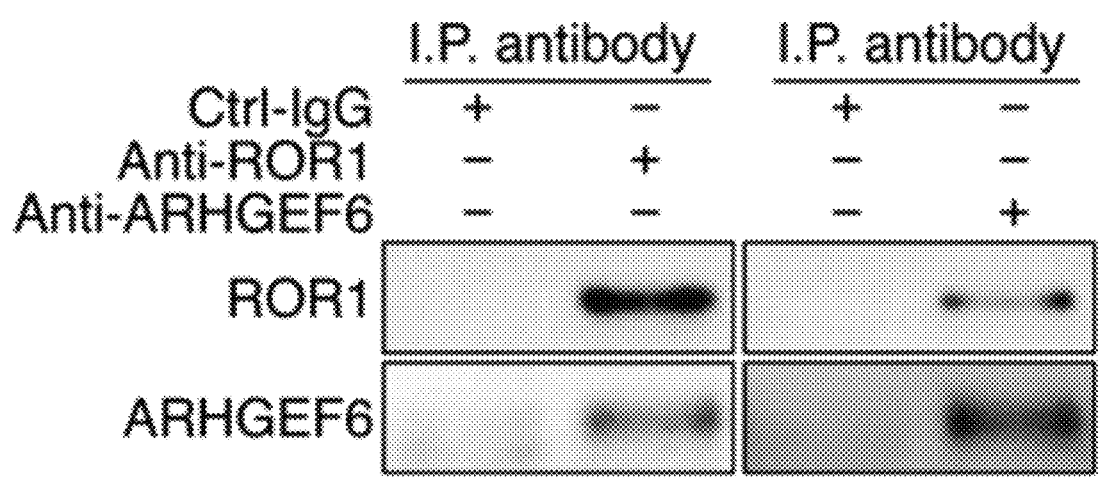
Figure 12A:
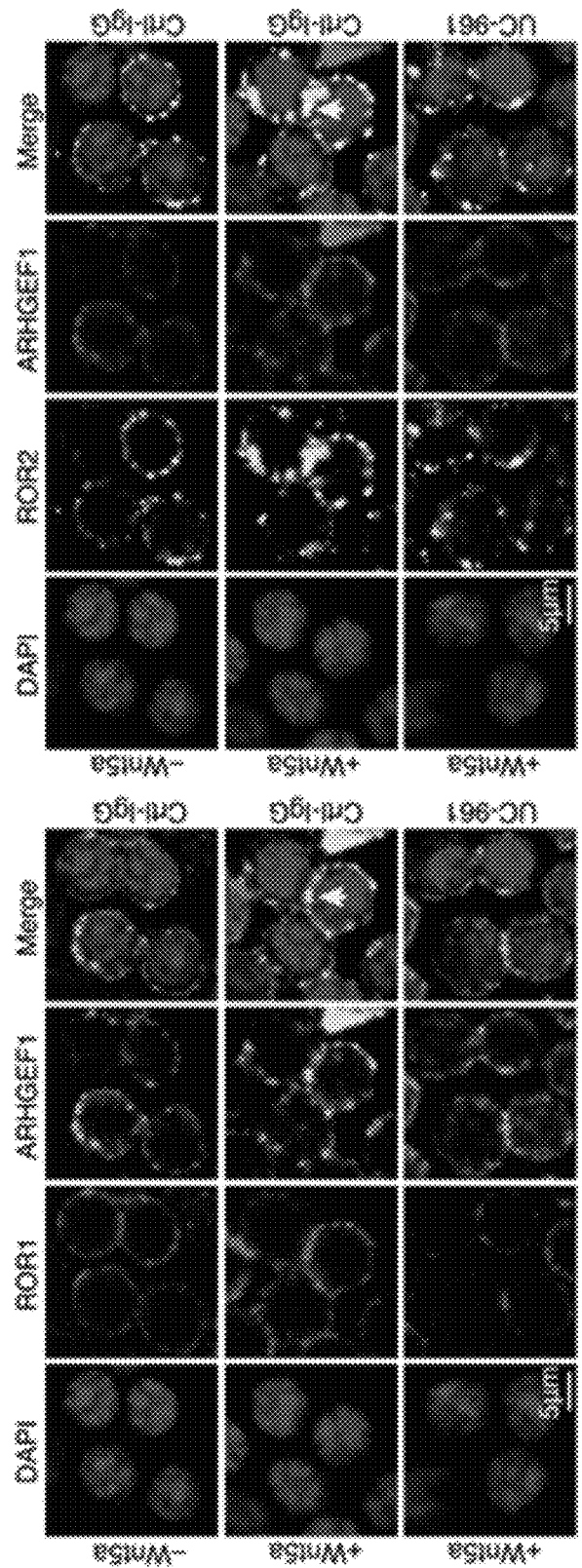
FIGS. 12A-12D. UC-961 inhibits co-localization of ARHGEF1, ARHGEF2, or ARHGEF6 with ROR1 or ROR2.

GEFs can activate RhoA and Rac1 [45]. Mass spectrometry analysis detected ARHGEF1, ARHGEF2, and ARHGEF6 in the anti-ROR1 ip (FIG. 11A). This association was confirmed by immunoblot analysis of the anti-ROR1 ip, which we found contained each of these GEFs (FIG. 11B). Moreover, the ip generated from lysates of freshly-isolated CLL cells using mAbs specific for either ARHGEF1, ARHGEF2, or ARHGEF6 each contained ROR1 detectable by immunoblot analysis (FIG. 11B). Fluorescence confocal microscopy showed that ROR1 and ROR2 co-localized with ARHGEF1, ARHGEF2, or ARHGEF6 in cultured CLL cells that were treated with exogenous Wnt5a (FIG. 4a-c). However, treatment with UC-961 inhibited the capacity of Wnt5a to induce recruitment of any one of these GEFs to either ROR1 or ROR2 (FIG. 12A).

Figure 4D:
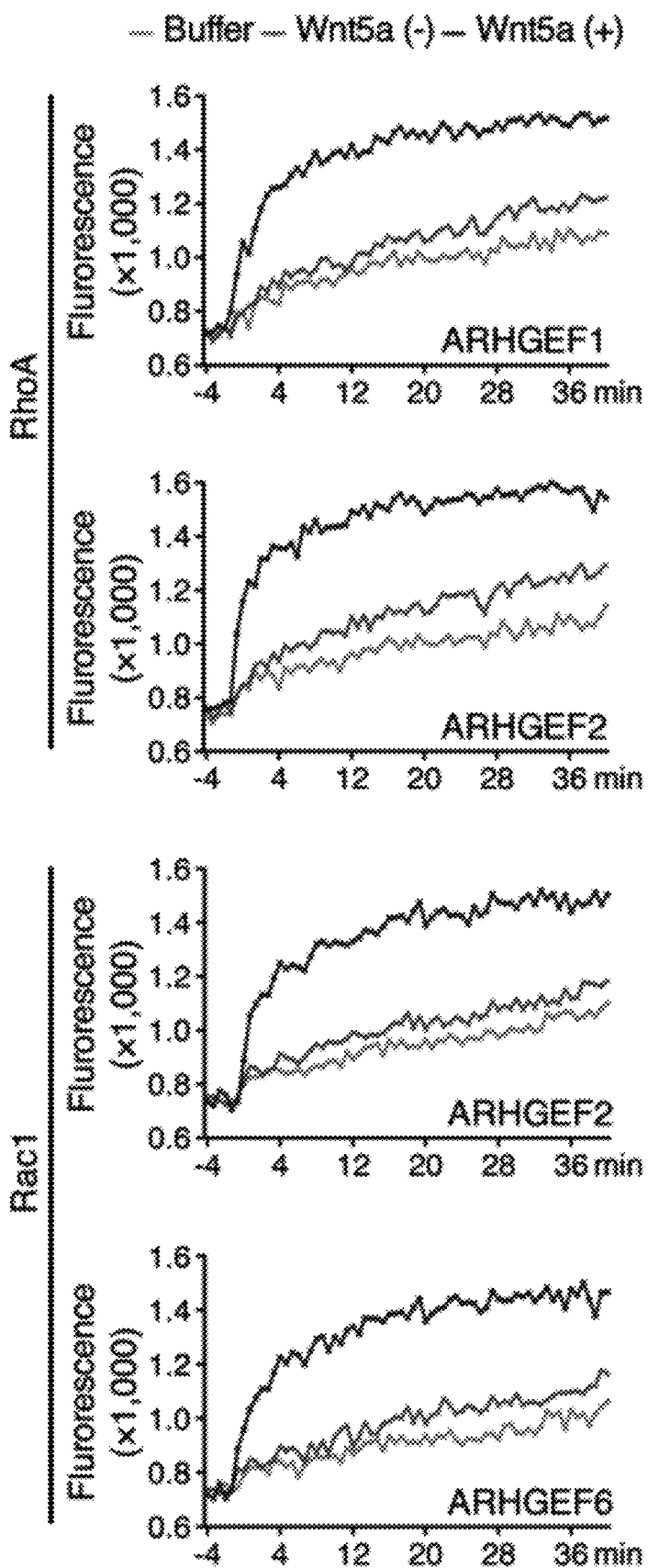
Figure 4E:
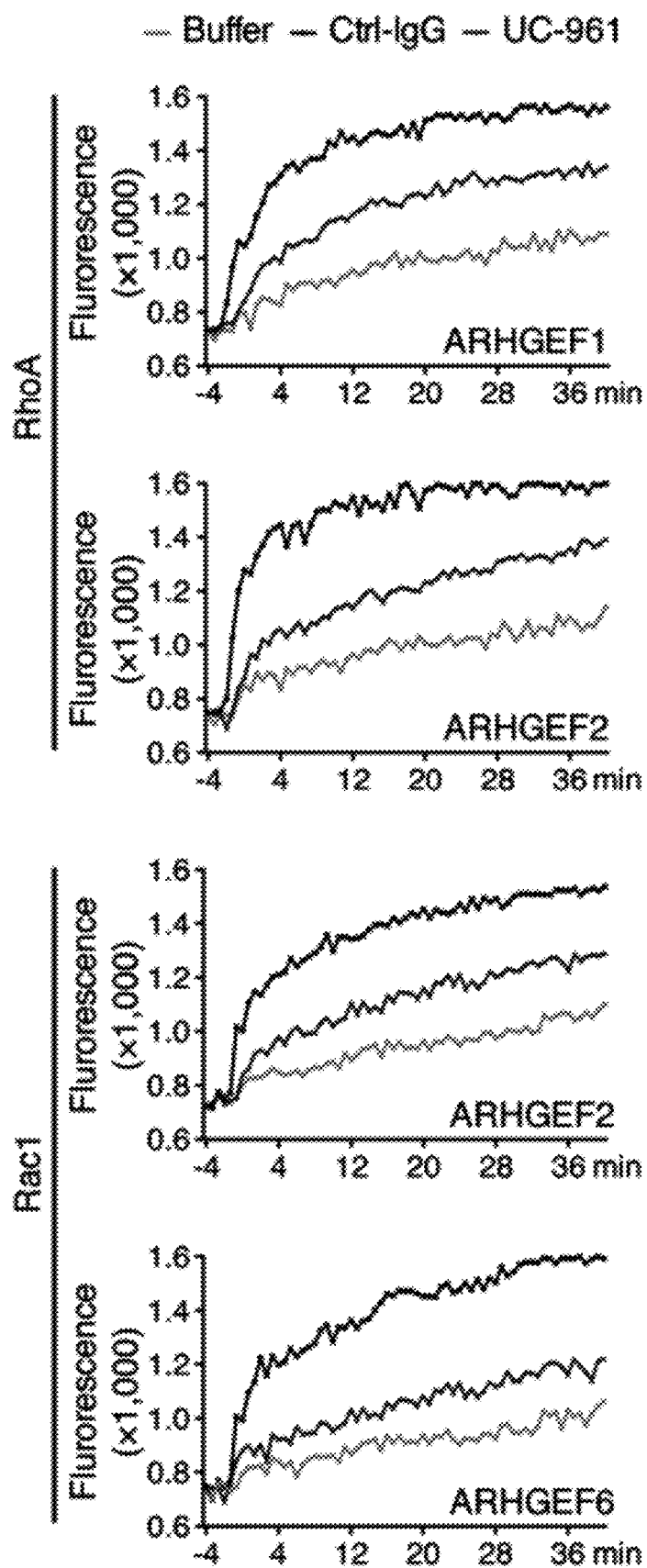
Figure 12B:
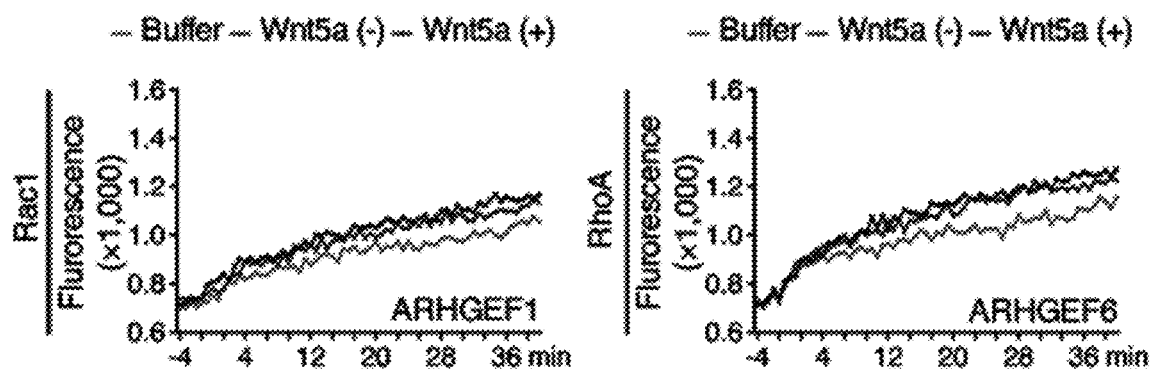

We found that treatment with Wnt5a increased the in vitro exchange activity for RhoA of ip generated with mAbs specific for either ARHGEF1 or ARHGEF2, but not ARHGEF6. Moreover, treatment with Wnt5a increased the in vitro exchange activity for Rac1 using ip generated with mAbs specific for either ARHGEF2 or ARHGEF6, but not ARHGEF1 (FIGS. 4D and 12B). Treatment with UC-961 inhibited the capacity of Wnt5a to induce activation of RhoA by ip generated from anti-ARHGEF1 or anti-ARHGEF2, or Rac1 by ip of anti-ARHGEF2 or anti-ARHGEF6, respectively (FIG. 4e).

Figure 4F:
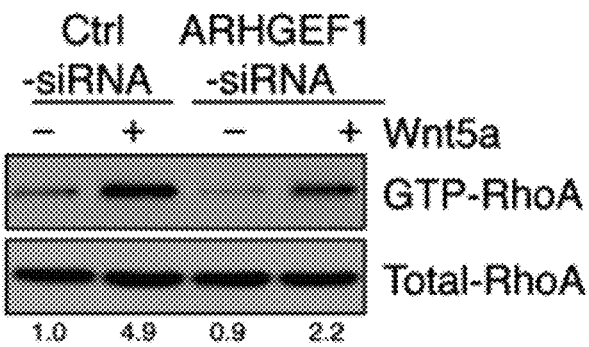
Figure 4F:
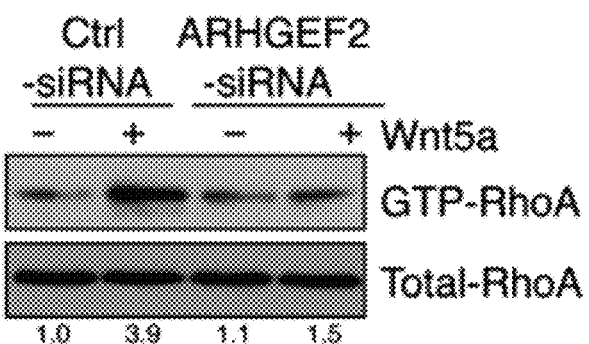
Figure 4F:
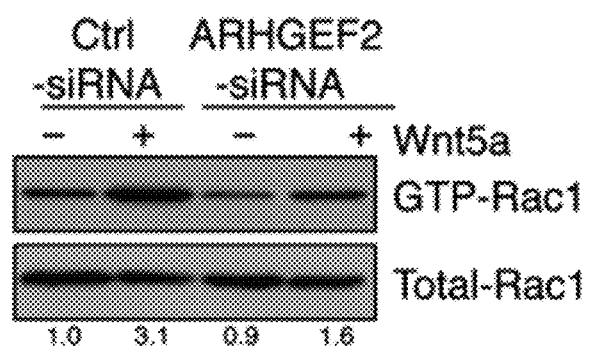
Figure 4F:
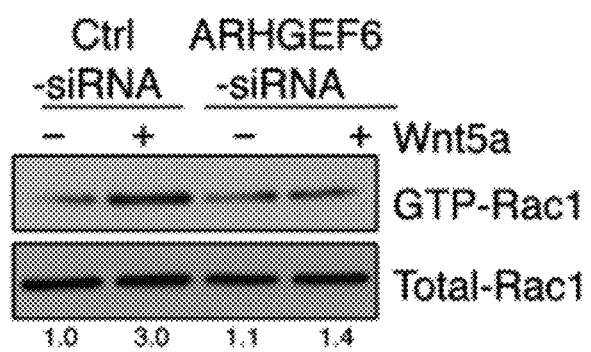
Figure 12C:
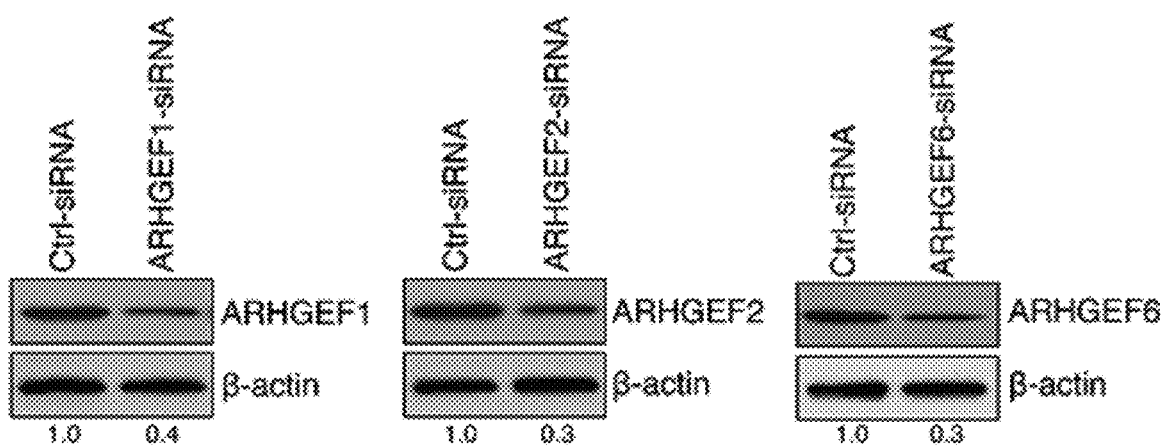
Figure 12D:
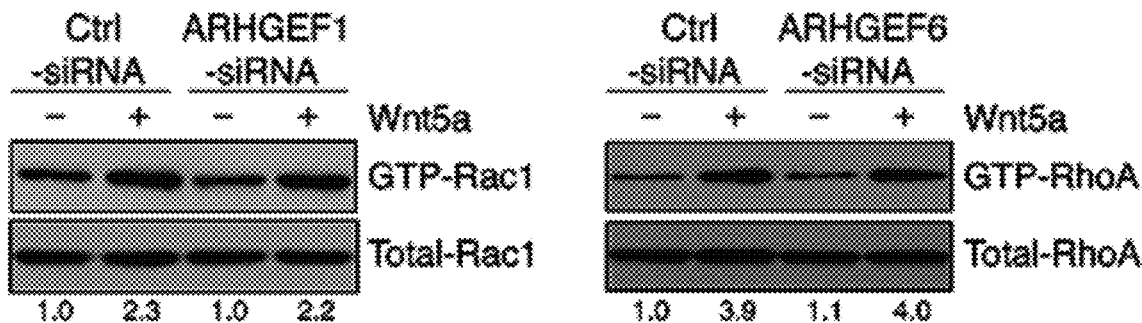

Wnt5a was less effective in activating RhoA in CLL cells transfected with siRNA specific for either ARHGEF1 or ARHGEF2 than in CLL cells transfected with control siRNA (FIGS. 4F and 12C). On the other hand, Wnt5a was less effective in activating Rac1 in CLL cells transfected with siRNA specific for either ARHGEF2 or ARHGEF6 (FIGS. 4F and 12C). However, CLL cells silenced for ARHGEF1 or ARHGEF6 respectively did not have impaired Wnt5a-induced activation of Rac1 or RhoA (FIG. 12D), indicating that ARHGEF1 and ARHGEF2, or ARHGEF2 and ARHGEF6, were required for optimal Wnt5a-induced activation of RhoA or Rac1, respectively.

Example 5—Mapping the Functional Domains of ROR1

Figure 13A:
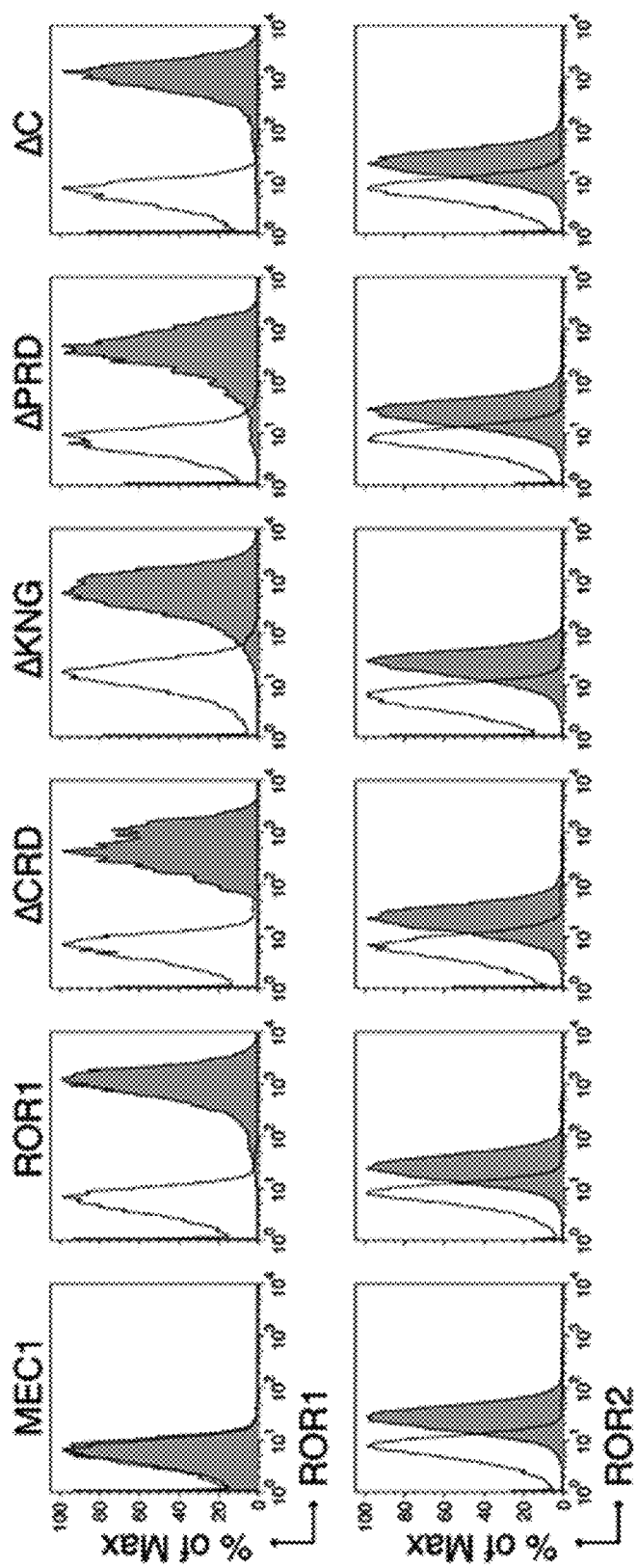
FIGS. 13A-13B. Expression of ROR1, ROR2, and Wnt5a in parental MEC1 cells and MEC1 cells transfected with each of the various ROR1 constructs.

MEC1 cells were derived from CLL and have been used as a cell-model for this leukaemia [30]. However, we found that MEC1 cells lacked ROR1, but did express ROR2 (FIG. 13A). Stable transfection of MEC1 with vectors encoding full-length ROR1, or each of various truncated-forms of ROR1 lacking distinct structural domains, allowed us to generate MEC1 that expressed high-levels of surface ROR1, which could be detected via flow cytometry using 4A5 mAb (FIG. 13A). Expression of ROR1, or any one of the various truncated forms of ROR1, did not alter the expression-level of surface ROR2 (FIG. 13A).

Figure 5A:
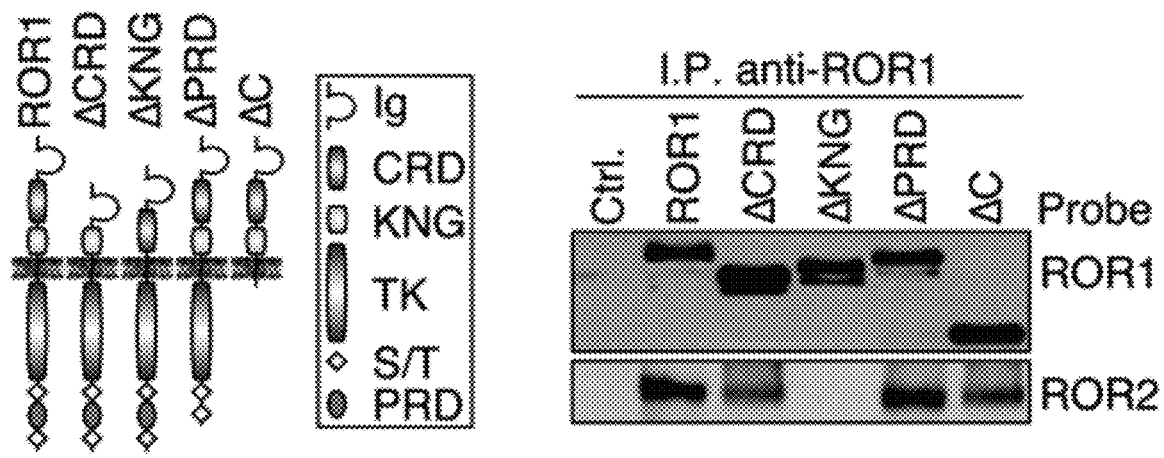
FIGS. 5A-5I. Mapping the functional domains of ROR1.
Figure 5B:
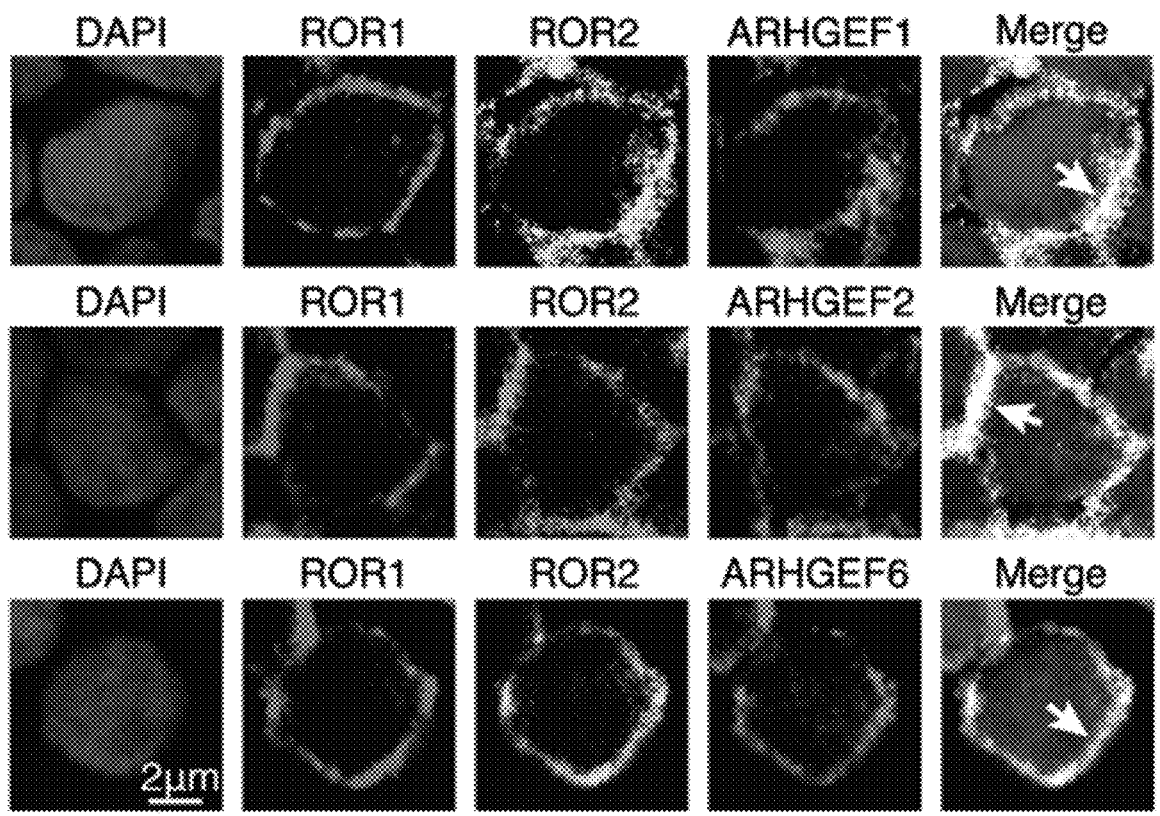
Figure 5C:
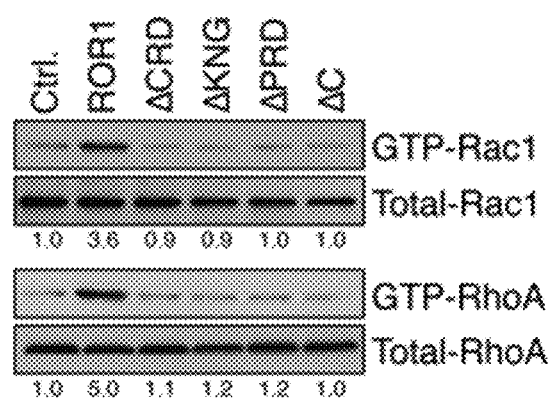
Figure 5D:
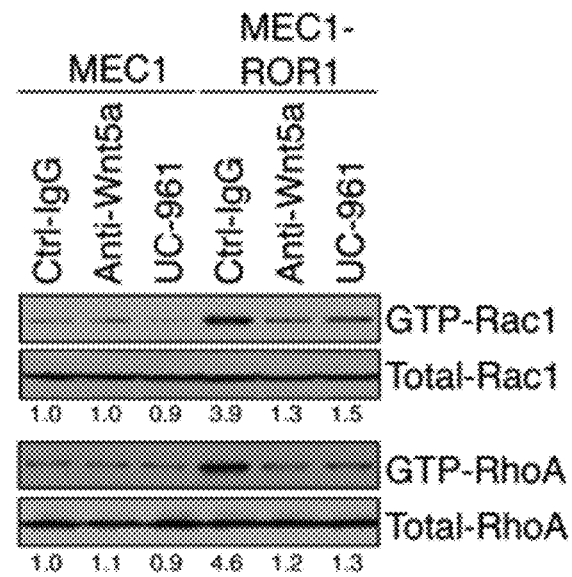
Figure 13B:
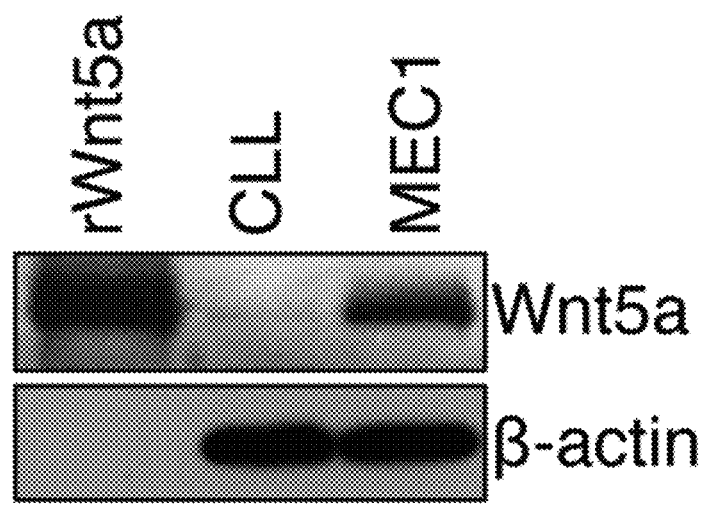
Figure 14A:
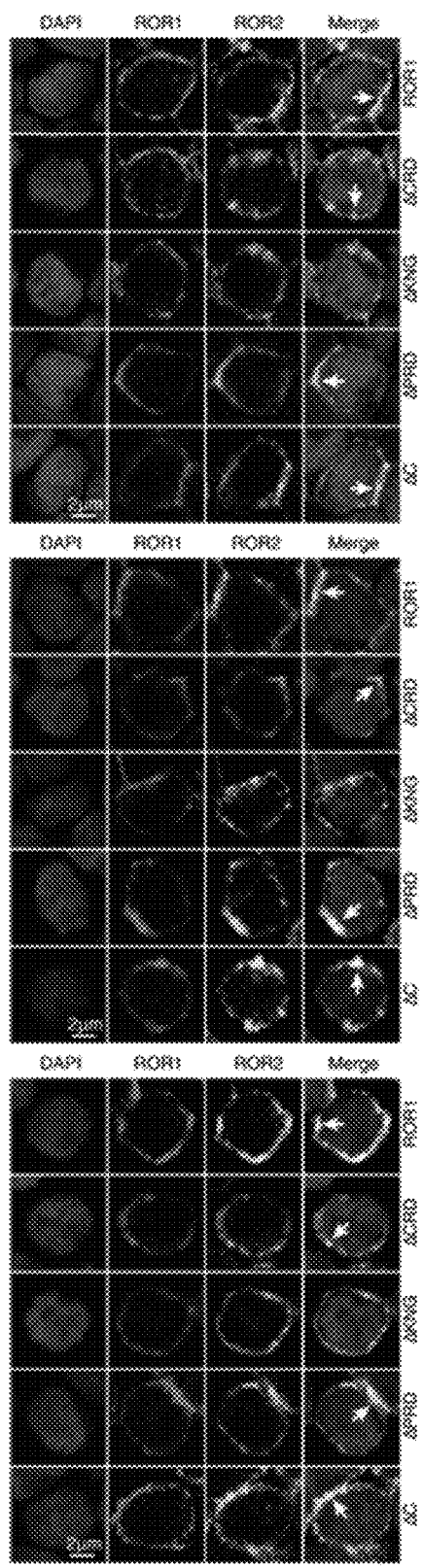
FIGS. 14A-14C. Confocal microscopy of MEC1 cells made to express ROR1 or various truncated forms of ROR1.
Figure 14B:
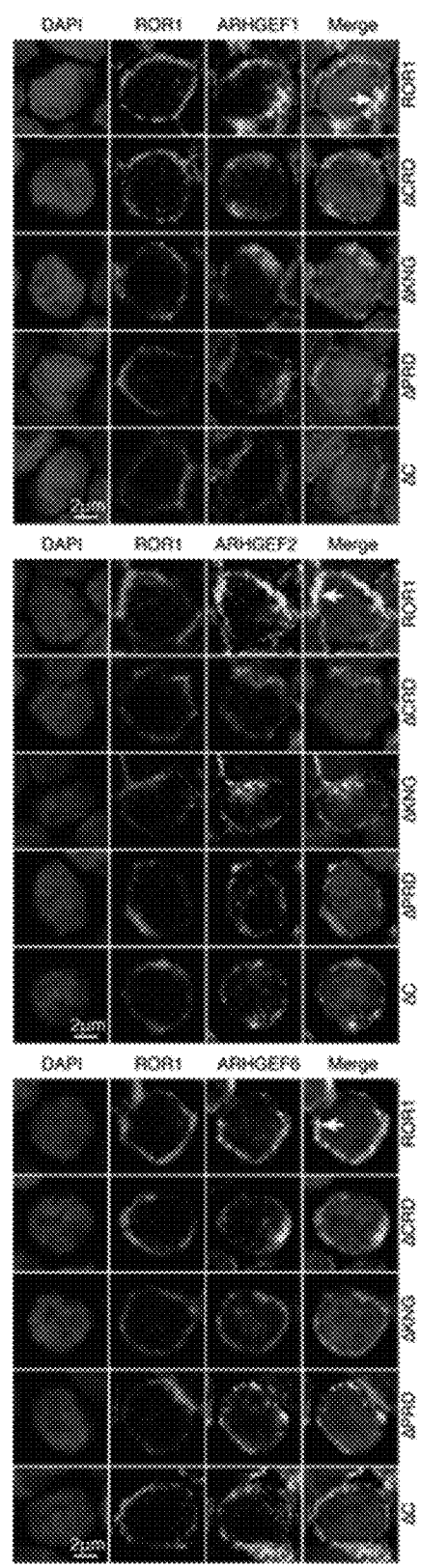
Figure 14C:
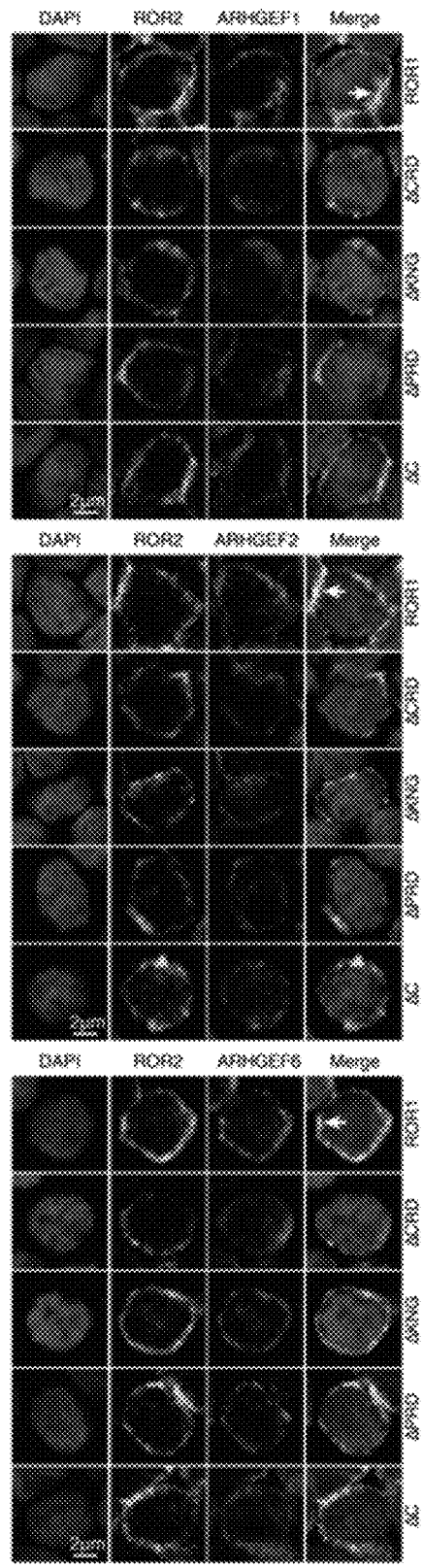

Because MEC1 cells express high levels of Wnt5a (FIG. 13B) [41], we assessed for constitutive ROR1-ROR2 coupling in MEC1 cells made to express ROR1. We detected ROR2 coupled with ROR1 in each of the transfectants except for MEC1 transfected with ROR1 lacking the extracellular KNG domain (MEC1-ΔKNG) (FIGS. 5A and 14A). Fluorescence confocal microscopy demonstrated that ROR1 and ROR2 co-localized with ARHGEF1, ARHGEF2, or ARHGEF6 in MEC1-ROR1 cells (FIG. 5b). However, we did not observe co-localization or ROR1-ROR2 with any one of these GEFs in MEC1 cells that expressed any of the truncated forms of ROR1 (FIGS. 14B-14C). MEC1-ROR1 cells also had higher levels of activated Rac1 and RhoA than MEC1 (FIG. 5c); such enhanced activation could be inhibited by treatment with either UC-961 or neutralizing antibodies to Wnt5a (FIG. 5d). However, the MEC1 cells transfected with any one of the various truncated forms of ROR1 did not have levels of activated Rac1 or RhoA that were greater than that of the parental MEC1 cells.

Figure 5E:
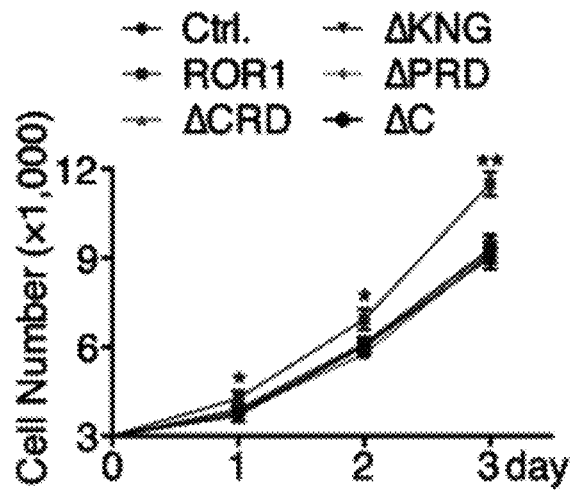
Figure 5F:
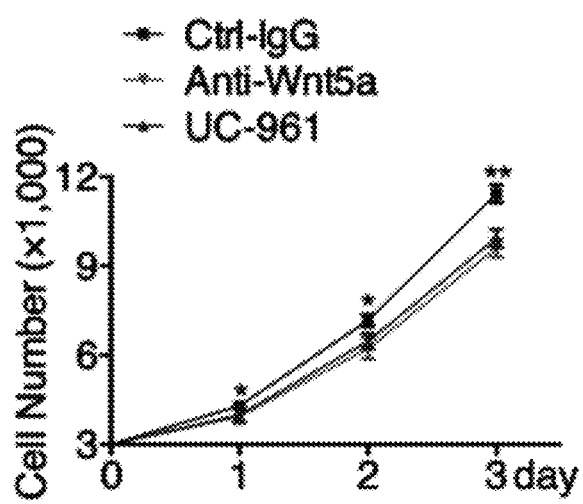
Figure 5G:
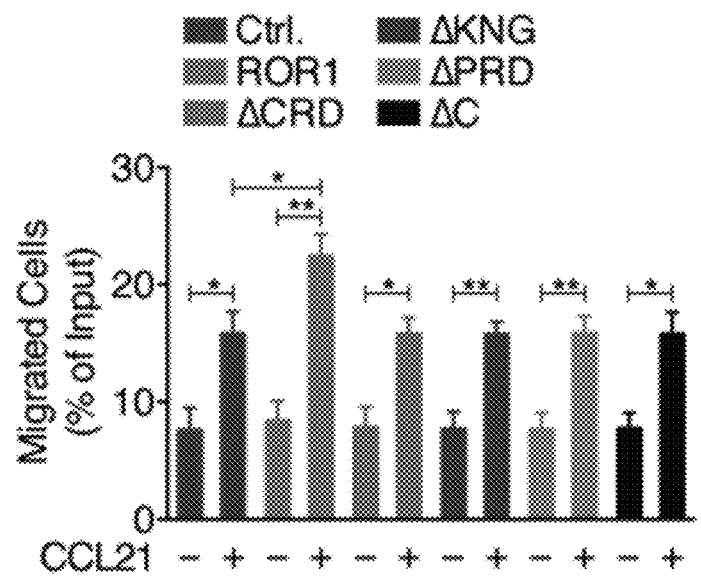
Figure 5H:
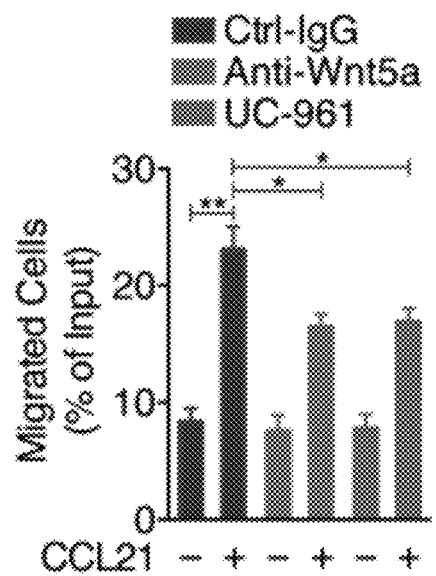
Figure 5I:
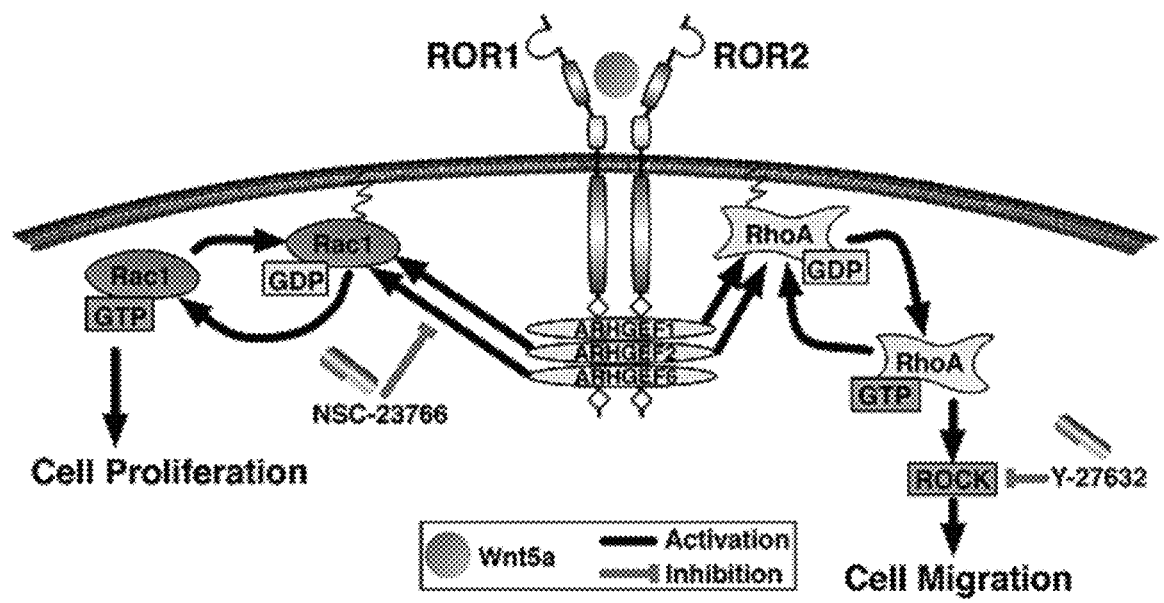

We compared the growth of MEC1 with MEC1 cells transfected with each of the various ROR1 constructs. MEC1-ROR1 cells grew faster than parental MEC1 cells or MEC1 cells transfected with any one of the truncated forms of ROR1 (FIG. 5e). Treatment with either neutralizing antibodies to Wnt5a or UC-961 could inhibit the growth of MEC1-ROR1 cells (FIG. 5f). Furthermore MEC1-ROR1 migrated significantly better in response to CCL21 than did MEC1 cells, or MEC1 expressing any of the truncated forms of ROR1 (FIG. 5g). Treatment with either neutralizing antibodies to Wnt5a or UC-961 could inhibit the migration of MEC1-ROR1 cells in response to CCL21 (FIG. 5h). Collectively, these data support a model that Wnt5a-induces co-localization of ROR1 with ROR2, which together recruit the GEFs responsible for Wnt5a-induced activation of RhoA and Rac1 (FIG. 5i).

Example 6—UC-961 mAb Inhibits the Progression of CLL In Vivo

Figure 6A:
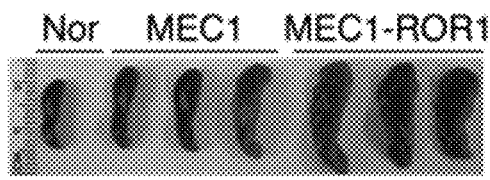
FIGS. 6A-6E. UC-961 inhibits engraftment of MEC1-ROR1.
Figure 6C:
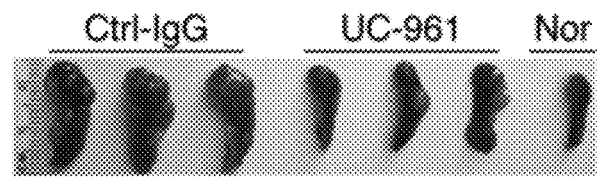
Figure 6B:
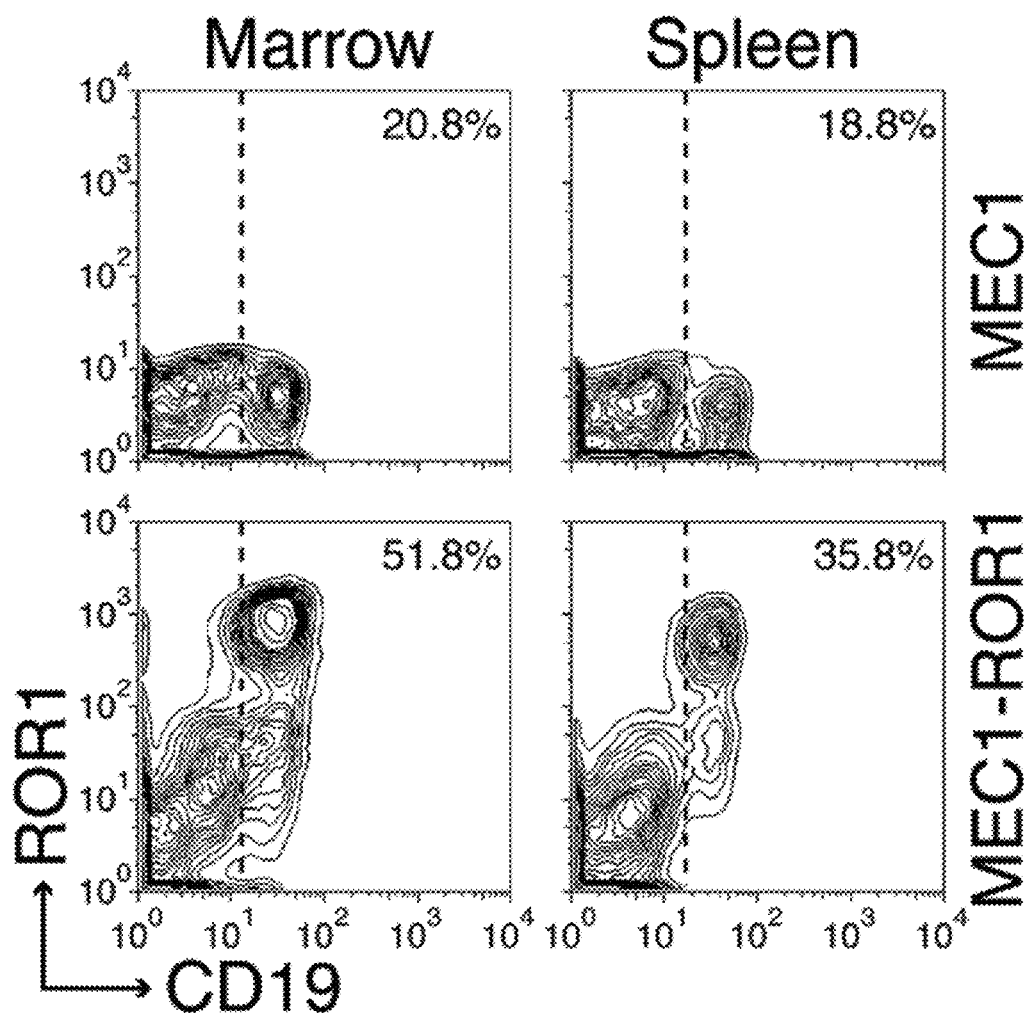
Figure 6D:
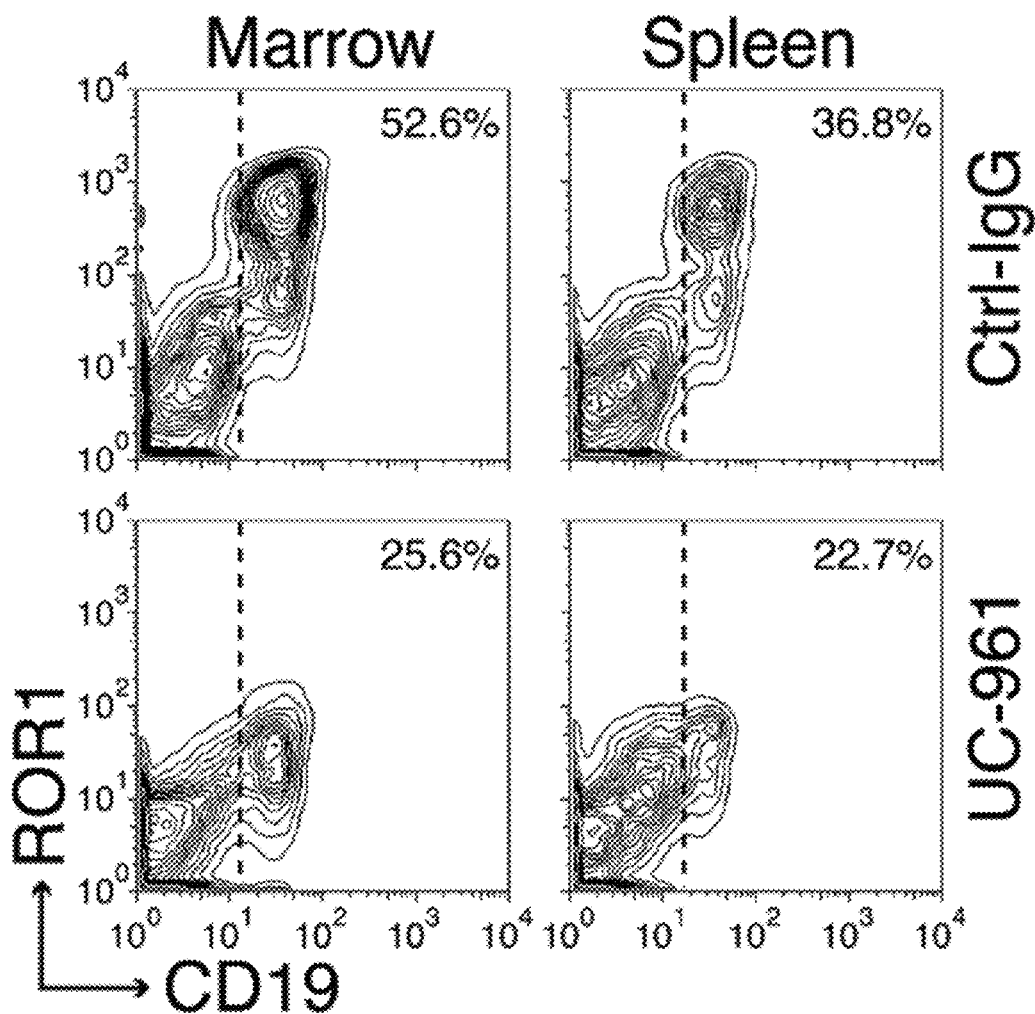
Figure 6E:
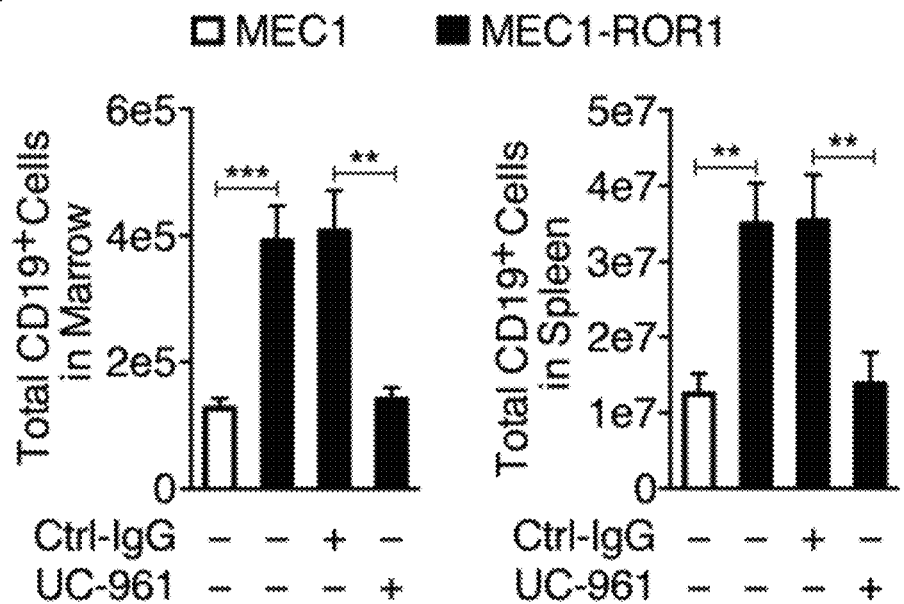

Prior studies indicated that MEC1 cells could engraft immune-deficient mice [46]. Three weeks after intravenous infusion of equal numbers of MEC1 or MEC1-ROR1 cells, $Rag2^{-/-}\gamma_c^{-/-}$ mice engrafted with MEC1-ROR1 cells had significantly greater splenic enlargement and marrow involvement with $CD19^+$ human leukaemia than did littermates infused with MEC1 (FIG. 6a, b). However, treatment with UC-961 significantly inhibited engraftment of MEC1-ROR1 (FIG. 6c-e). Moreover, the MEC1-ROR1 cells harvested from mice treated with UC-961 had lost or attenuated their expression of ROR1 (FIG. 6d).

REFERENCES

[1] Masiakowski, P. & Carroll, R. D. A novel family of cell surface receptors with tyrosine kinase-like domain. J. Biol. Chem. 267, 26181-26190 (1992); [2] Wilson, C., Goberdhan, D. C. & Steller, H. Dror, a potential neurotrophic receptor gene, encodes a *Drosophila* homolog of the vertebrate Ror family of Trk-related receptor tyrosine kinases. Proc. Natl. Acad. Sci. U.S.A 90, 7109-7113 (1993); [3] Forrester, W. C., Dell, M., Perens, E. & Garriga, G. A *C. elegans* Ror receptor tyrosine kinase regulates cell motility and asymmetric cell division. Nature 400, 881-885 (1999); [4] Koga, M., Take-uchi, M., Tameishi, T. & Ohshima, Y. Control of DAF-7 TGF-(alpha) expression and neuronal process development by a receptor tyrosine kinase KIN-8 in *Caenorhabditis elegans*. Development 126, 5387-5398 (1999); [5] McKay, S. E. et al. Aplysia ror forms clusters on the surface of identified neuroendocrine cells. Mol. Cell. Neurosci. 17, 821-841 (2001); [6] Hikasa, H., Shibata, M., Hiratani, I. & Taira, M. The *Xenopus* receptor tyrosine kinase Xror2 modulates morphogenetic movements of the axial mesoderm and neuroectoderm via Wnt signaling. Development 129, 5227-5239 (2002); [7] Rodriguez-Niedenfuhr, M., Prols, F. & Christ, B. Expression and regulation of ROR-1 during early avian limb development. Anat. Embryol. (Berl.) 207, 495-502 (2004); [8] Katoh, M. & Katoh, M. Comparative genomics on ROR1 and ROR2 orthologs. Oncol. Rep. 14, 1381-1384 (2005); [9] Minami, Y., Oishi, I., Endo, M. & Nishita, M. Ror-family receptor tyrosine kinases in noncanonical Wnt signaling: their implications in developmental morphogenesis and human diseases. Dev. Dyn. 239, 1-15 (2010); [10] Oishi, I. et al. Spatio-temporally regulated expression of receptor tyrosine kinases, mRor1, mRor2, during mouse development: implications in development and function of the nervous system. Genes Cells 4, 41-56 (1999); [11] Al-Shawi, R., Ashton, S. V., Underwood, C. & Simons, J. P. Expression of the Ror1 and Ror2 receptor tyrosine kinase genes during mouse development. Dev. Genes Evol. 211, 161-171 (2001); [12] Nomi, M. et al. Loss of mRor1 enhances the heart and skeletal abnormalities in mRor2-deficient mice: redundant and pleiotropic functions of mRor1 and mRor2 receptor tyrosine kinases. Mol. Cell. Biol. 21, 8329-8335 (2001); [13] Lyashenko, N. et al. Mice lacking the orphan receptor ror1 have distinct skeletal abnormalities and are growth retarded. Dev. Dyn. 239, 2266-2277 (2010); [14] Broome, H. E., Rassenti, L. Z., Wang, H. Y., Meyer, L. M. & Kipps, T. J. ROR1 is expressed on hematogones (non-neoplastic human B-lymphocyte precursors) and a minority of precursor-B acute lymphoblastic leukemia. Leuk. Res. 35, 1390-1394 (2011); [15] Fukuda, T. et al. Antisera induced by infusions of autologous Ad-CD154-leukemia B cells identify ROR1 as an oncofetal antigen and receptor for Wnt5a. Proc. Natl. Acad. Sci. U.S.A 105, 3047-3052 (2008); [16] Daneshmanesh, A. H. et al. Ror1, a cell surface receptor tyrosine kinase is expressed in chronic lymphocytic leukemia and may serve as a putative target for therapy. Int. J. Cancer 123, 1190-1195 (2008); [17] Baskar, S. et al. Unique cell surface expression of receptor tyrosine kinase ROR1 in human B-cell chronic lymphocytic leukemia. Clin. Cancer Res. 14, 396-404 (2008); [18] Zhang, S. et al. The onco-embryonic antigen ROR1 is expressed by a variety of human cancers. Am. J. Pathol. 181, 1903-1910 (2012); [19] Debebe, Z. & Rathmell, W. K. Ror2 as a Therapeutic Target in Cancer. Pharmacol. Ther. (2015); [20] Cui, B. et al. Targeting ROR1 inhibits epithelial-mesenchymal transition and metastasis. Cancer Res. 73, 3649-3660 (2013); [21] Li, X. et al. Activation of Wnt5a-Ror2 signaling associated with epithelial-to-mesenchymal transition of tubular epithelial cells during renal fibrosis. Genes Cells 18, 608-619 (2013); [22] Zhang, S. et al. Ovarian cancer stem cells express ROR1, which can be targeted for anti-cancer-stem-cell therapy. Proc. Natl. Acad. Sci. U.S.A 111, 17266-17271 (2014); [23] Oishi, I. et al. The receptor tyrosine kinase Ror2 is involved in non-canonical Wnt5a/JNK signalling pathway. Genes Cells 8, 645-654 (2003); [24] Green, J. L., Inoue, T. & Sternberg, P. W. Opposing Wnt pathways orient cell polarity during organogenesis. Cell 134, 646-656 (2008); [25] He, F. et al. Wnt5a regulates directional cell migration and cell proliferation via Ror2-mediated noncanonical pathway in mammalian palate development. Development 135, 3871-3879 (2008); [26] Ho, H. Y. et al. Wnt5a-Ror-Dishevelled signaling constitutes a core developmental pathway that controls tissue morphogenesis. Proc. Natl. Acad. Sci. U.S.A 109, 4044-4051 (2012); [27] Ford, C. E., Qian Ma, S. S., Quadir, A. & Ward, R. L. The dual role of the novel Wnt receptor tyrosine kinase, ROR2, in human carcinogenesis. Int. J. Cancer 133, 779-787 (2013); [28] Gentile, A., Lazzari, L., Benvenuti, S., Trusolino, L. & Comoglio, P. M. Ror1 is a pseudokinase that is crucial for Met-driven tumorigenesis. Cancer Res. 71, 3132-3141 (2011); [29] Yamaguchi, T. et al. NKX2-1/TITF1/TTF-1-Induced ROR1 is required to sustain EGFR survival signaling in lung adenocarcinoma. Cancer Cell 21, 348-361 (2012); [30] Stacchini, A. et al. MEC1 and MEC2: two new cell lines derived from B-chronic lymphocytic leukaemia in prolymphocytoid transformation. Leuk. Res. 23, 127-136 (1999); [31] Yamagata, K. et al. Dissection of Wnt5a-Ror2 signaling leading to matrix metalloproteinase (MMP-13) expression. J. Biol. Chem. 287, 1588-1599 (2012); [32] Petrova, I. M., Malessy, M. J., Verhaagen, J., Fradkin, L. G. & Noordermeer, J. N. Wnt signaling through the Ror receptor in the nervous system. Mol. Neurobiol. 49, 303-315 (2014); [33] Endo, M., Nishita, M., Fujii, M. & Minami, Y. Insight into the role of Wnt5a-induced signaling in normal and cancer cells. Int. Rev. Cell Mol. Biol. 314, 117-148 (2015); [34] Graversen, J. H., Sigurskjold, B. W., Thogersen, H. C. & Etzerodt, M. Tetranectin-binding site on plasminogen kringle 4 involves the lysine-binding pocket and at least one additional amino acid residue. Biochemistry 39, 7414-7419 (2000); [35] Roszmusz, E., Patthy, A., Trexler, M. & Patthy, L. Localization of disulfide bonds in the frizzled module of Ror1 receptor tyrosine kinase. J. Biol. Chem. 276, 18485-18490 (2001); [36] Green, J. L., Kuntz, S. G. & Sternberg, P. W. Ror receptor tyrosine kinases: orphans no more. Trends Cell Biol. 18, 536-544 (2008); [37] Yamamoto, S. et al. Cthrc1 selectively activates the planar cell polarity pathway of Wnt signaling by stabilizing the Wnt-receptor complex. Dev. Cell 15, 23-36 (2008); [38] Nishita, M. et al. Ror2/Frizzled complex mediates Wnt5a-induced AP-1 activation by regulating Dishevelled polymerization. Mol. Cell. Biol. 30, 3610-3619 (2010); [39] Grumolato, L. et al. Canonical and noncanonical Wnts use a common mechanism to activate completely unrelated coreceptors. Genes Dev. 24, 2517-2530 (2010); [40] Seifert, M. et al. Cellular origin and pathophysiology of chronic lymphocytic leukemia. J. Exp. Med. 209, 2183-2198 (2012); [41] Kaucka, M. et al. The planar cell polarity pathway drives pathogenesis of chronic lymphocytic leukemia by the regulation of B-lymphocyte migration. Cancer Res. 73, 1491-1501 (2013); [42] Etienne-Manneville, S. & Hall, A. Rho GTPases in cell biology. Nature 420, 629-635 (2002); [43] Lee, J. G. & Heur, M. Interleukin-1beta-induced Wnt5a enhances human corneal endothelial cell migration through regulation of Cdc42 and RhoA. Mol. Cell. Biol. 34, 3535-3545 (2014); [44] Hofbauer, S. W. et al. Tiam1/Rac1 signals contribute to the proliferation and chemoresistance, but not motility, of chronic lymphocytic leukemia cells. Blood 123, 2181-2188 (2014); [45] Bos, J. L., Rehmann, H. & Wittinghofer, A. GEFs and GAPs: critical elements in the control of small G proteins. Cell 129, 865-877 (2007); [46] Bertilaccio, M. T. et al. A novel Rag2−/−gammac−/−-xenograft model of human CLL. Blood 115, 1605-1609 (2010).

IV. Embodiments

Embodiments contemplated herein include the following.

Embodiment P1. A method for identifying an agent that disrupts ROR1 and ROR2 coupling comprising: a. Contacting CLL cells co-expressing ROR1 and ROR2 with Wnt5a; b. contacting said CLL cells with the agent or a control; and c. determining the presence or absence of ROR1 and ROR2 coupling, wherein the absence of ROR1 and ROR2 coupling in the agent contacted cells compared to the control cells is indicative of disruption of ROR1 and ROR2 coupling, by which an agent that disrupts ROR1 and ROR2 coupling is identified.

Embodiment P2. The method of embodiment P1, wherein the agent is an antibody, a peptide, a small molecule or siRNA.

Embodiment P3. The method of embodiment P1 or P2, wherein the agent is an antibody.

Embodiment P4. The method of one of embodiments P1-P3, wherein the antibody is UC-961.

Embodiment P5. The method of one of embodiments P1-P4, wherein the agent is a siRNA.

Embodiment P6. The method of embodiment P5, wherein the siRNA is specific for ROR1 or ROR2.

Embodiment P7. The method one of embodiments P1-P6, wherein the presence or absence of ROR1 and ROR2 coupling is determined by measuring co-localization of ROR1 and ROR2 or by inhibition of Wnt5a activity.

Embodiment P8. The method of embodiment P7, wherein the co-localization of ROR1 and ROR2 or by inhibition of Wnt5a activity is determined using a fluorescence assay.

Embodiment P9. The method of embodiment P8, wherein the fluorescence assay is selected from the group consisting of: fluorescence confocal microscopy, fluorescence resonance energy transfer (FRET), ELISA, FACS, mass spectroscopy, and cell based assay.

Embodiment P10. The method of embodiment P7, wherein inhibition of Wnt5a activity is indicated by decreased or lack of RhoA and RAC1 activity in the agent contacted cells compared with the control cells.

Embodiment P11. The method of embodiment P7, wherein inhibition of Wnt5a activity is indicated by decreased or lack of ARHGEF1, ARHGEF2 and/or ARHGEF6 expression in the agent contacted cells compared with the control cells.

Embodiment P12. The method of one of embodiments P1-P11, wherein the CLL cells are MEC1 cells.

Embodiment P13. An isolated antibody, which inhibits ROR1 and ROR2 coupling.

Embodiment P14. The antibody of embodiment P13, wherein the antibody is monoclonal, chimeric, human or humanized.

Embodiment P15. The antibody of embodiment P13, wherein the antibody inhibits Wnt5a activity.

Embodiment P16. The antibody of embodiment P15, wherein the inhibition of Wnt5a activity is indicated by the inhibition RhoA and/or Rac1 activity.

Embodiment P17. The antibody of embodiment P15, wherein inhibition of Wnt5a activity is indicated by decreased or lack of ARHGEF1, ARHGEF2 and/or ARHGEF6 recruitment.

Embodiment P18. The antibody of embodiment P13, wherein the antibody blocks the KNG domain of ROR1 from coupling with ROR2.

Embodiment P19. A method of treating CLL comprising administering an agent that disrupts ROR1 and ROR2 coupling to a subject in need thereof.

Further embodiments contemplated herein include the following.

Embodiment 1. A method of identifying an inhibitor of ROR1-ROR2 binding, said method comprising: (i) combining a test agent with a ROR1 protein and a ROR2 protein in a reaction vessel; and (ii) detecting a decrease in binding of said ROR1 protein to said ROR2 protein relative to a standard control, thereby identifying an inhibitor of ROR1-ROR2 binding.

Embodiment 2. The method of embodiment 1, wherein said detecting comprises detecting a level of said ROR1 protein bound to said ROR2 protein in the presence of said test agent, wherein a decreased level of said ROR1 protein bound to said ROR2 protein relative to a standard control indicates said test agent is an inhibitor of ROR1-ROR2 binding.

Embodiment 3. The method of embodiment 1, wherein said detecting comprises detecting a level of unbound ROR1 protein or unbound ROR2 protein in the presence of said test agent, wherein an increased level of unbound ROR1 protein or an increased level of unbound ROR2 protein relative to a standard control indicates said test agent is an inhibitor of ROR1-ROR2 binding.

Embodiment 4. The method of one of embodiments 1-3, wherein said ROR1 protein and said ROR2 protein comprise a detectable moiety.

Embodiment 5. The method of embodiment 1, wherein said detecting comprises detecting a level of a guanine exchange factor (GEF) or a guanosine triphosphatase (GTPase) in the presence of said test agent, wherein a decreased level of said GEF relative to a standard control indicates said test agent is an inhibitor of ROR1-ROR2 binding.

Embodiment 6. The method of embodiment 5, wherein said GEF is ARHGEF1, ARHGEF2 or ARHGEF6.

Embodiment 7. The method of embodiment 5, wherein said GTPase is RhoA or Rac1.

Embodiment 8. The method of one of embodiments 5-7, wherein said GEF or GTPase comprises a detectable moiety.

Embodiment 9. The method of one of embodiments 1-8, wherein said combining occurs in the presence of a Wnt5a protein.

Embodiment 10. The method of one of embodiments 1-9, wherein said reaction vessel is a column comprising a solid support.

Embodiment 11. The method of one of embodiments 1-9, wherein said reaction vessel comprises a cell.

Embodiment 12. The method of embodiment 11, wherein said ROR1 protein and said ROR2 protein are expressed on the surface of said cell.

Embodiment 13. The method of embodiment 11 or 12, wherein said cell is a cancer cell.

Embodiment 14. The method of embodiment 13, wherein said cancer cell is a chronic lymphocytic leukemia (CLL) cell.

Embodiment 15. The method of embodiment 14, wherein said CLL cell is a MEC1 cell.

Embodiment 16. The method of one of embodiments 11-14, wherein said cell forms part of an in vitro cell culture.

Embodiment 17. The method of one of embodiments 11-16, wherein said cell forms part of an organism.

Embodiment 18. The method of embodiment 17, wherein said organism is a mammal.

Embodiment 19. The method of embodiment 17, wherein said organism is a mouse.

Embodiment 20. The method of one of embodiments 1-19, wherein said test agent is an antibody, a small molecule, a peptide, a protein or a nucleic acid.

Embodiment 21. The method of one of embodiments 1-17, wherein said test agent is an antibody.

Embodiment 22. The method of embodiment 17 or 18, wherein said antibody is an anti-ROR1 antibody.

Embodiment 23. The method of embodiment 17 or 18, wherein said antibody is an anti-ROR2 antibody.

Embodiment 24. The method of one of embodiments 17-20, wherein said antibody binds to a ROR1 protein or a ROR2 protein.

Embodiment 25. The method of embodiment 21, wherein said antibody binds to a KNG domain.

Embodiment 26. The method of one of embodiments 17-22, wherein said antibody is a humanized antibody.

Embodiment 27. The method of one of embodiments 17-22, wherein said antibody is a chimeric antibody.

Embodiment 28. The method of one of embodiments 17-22, wherein said antibody is a scFv.

Embodiment 29. An antibody identified by the method of any one of embodiments 1-22.

Embodiment 30. A method of inhibiting a ROR1-ROR2 interaction, said method comprising: (i) contacting a compound identified by the method of any one of embodiments 1-22 with a ROR1-ROR2 complex, wherein said complex comprises a ROR1 protein and a ROR2 protein; and (ii) allowing said compound to inhibit the interaction between said ROR1 protein and said ROR2 protein, thereby inhibiting a ROR1-ROR2 interaction.

Embodiment 31. A method of treating cancer in a subject in need thereof, said method comprising administering to a subject a therapeutically effective amount of an antibody, small molecule, peptide or nucleic acid identified by a method of one of embodiments 1-22.

What is claimed is:

1. A method of identifying an inhibitor of ROR1-ROR2 binding, said method comprising:
   (i) combining a test agent with a ROR1 protein and a ROR2 protein in a reaction vessel;
   (ii) detecting a decrease in binding of said ROR1 protein to said ROR2 protein relative to a standard control; and
   (iii) detecting a level of a guanine exchange factor (GEF) protein binding activity to said ROR1 protein or said ROR2 protein in the presence of said test agent, wherein a decreased level of said GEF protein binding activity relative to a standard control indicates said test agent is an inhibitor of ROR1-ROR2 binding; and wherein said GEF protein is ARHGEF2 or ARHGEF6.

2. The method of claim 1, wherein said detecting in step (ii) comprises detecting a level of said ROR1 protein bound to said ROR2 protein in the presence of said test agent, wherein a decreased level of said ROR1 protein bound to said ROR2 protein relative to a standard control indicates said test agent is an inhibitor of ROR1-ROR2 binding.

3. The method of claim 1, wherein said ROR1 protein and said ROR2 protein comprise a detectable moiety.

4. The method of claim 1, wherein said GEF protein comprises a detectable moiety.

5. The method of claim 1, wherein said combining occurs in the presence of a Wnt5a protein.

6. The method of claim 1, wherein said reaction vessel is a column comprising a solid support.

7. The method of claim 1, wherein said reaction vessel comprises a cell.

8. The method of claim 7, wherein said cell is a cancer cell.

9. The method of claim 8, wherein said cancer cell is a chronic lymphocytic leukemia (CLL) cell.

10. The method of claim 9, wherein said CLL cell is a MEC1 cell.

11. The method of claim 1, wherein said test agent is an antibody, a small molecule, a peptide, a protein, or a nucleic acid.

12. The method of claim 11, wherein said antibody is an anti-ROR1 antibody.

13. The method of claim 11, wherein said antibody is a humanized or a chimeric antibody.

14. The method of claim 11, wherein said antibody is a scFv.

* * * * *

SEQUENCE LISTING

```
<160> NUMBER OF SEQ ID NOS: 24

<210> SEQ ID NO 1
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 1
acgtgcacat gaggtccatt                                                20

<210> SEQ ID NO 2
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 2
caccgggtgt gggatttaca                                                20

<210> SEQ ID NO 3
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 3
tgccccgcac acattgttgg tcctatttgt aaatccca                             38

<210> SEQ ID NO 4
<211> LENGTH: 13
<212> TYPE: PRT
<213> ORGANISM: Artificial Sequence
<220> FEATURE:
<223> OTHER INFORMATION: Synthetic polypeptide
```

```
<400> SEQUENCE: 4

Cys Pro Ala His Ile Val Gly Pro Ile Cys Lys Ser His
1               5                   10

<210> SEQ ID NO 5
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 5

Lys Gln Leu Leu Phe Pro Ala Glu Glu Asp Asn Gly Ala Gly Pro Pro
1               5                   10                  15

Arg Asp

<210> SEQ ID NO 6
<211> LENGTH: 25
<212> TYPE: PRT
<213> ORGANISM: Artificial Sequence
<220> FEATURE:
<223> OTHER INFORMATION: Synthetic polypeptide

<400> SEQUENCE: 6

Lys Ala Ala Ala Gln Gly Pro Glu Gly Asp Ile Gln Glu Gln Glu Leu
1               5                   10                  15

Gln Ser Glu Glu Leu Gly Leu Arg Ala
            20                  25

<210> SEQ ID NO 7
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 7

Trp Gln Ile Trp Glu Leu Leu Ser Thr Asp Asn Pro Asp Ala Leu Pro
1               5                   10                  15

Glu

<210> SEQ ID NO 8
<211> LENGTH: 937
<212> TYPE: PRT
<213> ORGANISM: Homo sapiens

<400> SEQUENCE: 8

Met His Arg Pro Arg Arg Arg Gly Thr Arg Pro Pro Leu Leu Ala Leu
1               5                   10                  15

Leu Ala Ala Leu Leu Ala Ala Arg Gly Ala Ala Ala Gln Glu Thr
            20                  25                  30

Glu Leu Ser Val Ser Ala Glu Leu Val Pro Thr Ser Ser Trp Asn Ile
        35                  40                  45

Ser Ser Glu Leu Asn Lys Asp Ser Tyr Leu Thr Leu Asp Glu Pro Met
    50                  55                  60

Asn Asn Ile Thr Thr Ser Leu Gly Gln Thr Ala Glu Leu His Cys Lys
65                  70                  75                  80

Val Ser Gly Asn Pro Pro Pro Thr Ile Arg Trp Phe Lys Asn Asp Ala
                85                  90                  95

Pro Val Val Gln Glu Pro Arg Arg Leu Ser Phe Arg Ser Thr Ile Tyr
            100                 105                 110
```

```
Gly Ser Arg Leu Arg Ile Arg Asn Leu Asp Thr Thr Asp Thr Gly Tyr
            115                 120                 125

Phe Gln Cys Val Ala Thr Asn Gly Lys Glu Val Val Ser Ser Thr Gly
    130                 135                 140

Val Leu Phe Val Lys Phe Gly Pro Pro Thr Ala Ser Pro Gly Tyr
145                 150                 155                 160

Ser Asp Glu Tyr Glu Glu Asp Gly Phe Cys Gln Pro Tyr Arg Gly Ile
                165                 170                 175

Ala Cys Ala Arg Phe Ile Gly Asn Arg Thr Val Tyr Met Glu Ser Leu
            180                 185                 190

His Met Gln Gly Glu Ile Glu Asn Gln Ile Thr Ala Ala Phe Thr Met
        195                 200                 205

Ile Gly Thr Ser Ser His Leu Ser Asp Lys Cys Ser Gln Phe Ala Ile
    210                 215                 220

Pro Ser Leu Cys His Tyr Ala Phe Pro Tyr Cys Asp Glu Thr Ser Ser
225                 230                 235                 240

Val Pro Lys Pro Arg Asp Leu Cys Arg Asp Glu Cys Glu Ile Leu Glu
                245                 250                 255

Asn Val Leu Cys Gln Thr Glu Tyr Ile Phe Ala Arg Ser Asn Pro Met
            260                 265                 270

Ile Leu Met Arg Leu Lys Leu Pro Asn Cys Glu Asp Leu Pro Gln Pro
        275                 280                 285

Glu Ser Pro Glu Ala Ala Asn Cys Ile Arg Ile Gly Ile Pro Met Ala
    290                 295                 300

Asp Pro Ile Asn Lys Asn His Lys Cys Tyr Asn Ser Thr Gly Val Asp
305                 310                 315                 320

Tyr Arg Gly Thr Val Ser Val Thr Lys Ser Gly Arg Gln Cys Gln Pro
                325                 330                 335

Trp Asn Ser Gln Tyr Pro His Thr His Thr Phe Thr Ala Leu Arg Phe
            340                 345                 350

Pro Glu Leu Asn Gly Gly His Ser Tyr Cys Arg Asn Pro Gly Asn Gln
        355                 360                 365

Lys Glu Ala Pro Trp Cys Phe Thr Leu Asp Glu Asn Phe Lys Ser Asp
    370                 375                 380

Leu Cys Asp Ile Pro Ala Cys Asp Ser Lys Asp Ser Lys Glu Lys Asn
385                 390                 395                 400

Lys Met Glu Ile Leu Tyr Ile Leu Val Pro Ser Val Ala Ile Pro Leu
                405                 410                 415

Ala Ile Ala Leu Leu Phe Phe Phe Ile Cys Val Cys Arg Asn Asn Gln
            420                 425                 430

Lys Ser Ser Ser Ala Pro Val Gln Arg Gln Pro Lys His Val Arg Gly
        435                 440                 445

Gln Asn Val Glu Met Ser Met Leu Asn Ala Tyr Lys Pro Lys Ser Lys
    450                 455                 460

Ala Lys Glu Leu Pro Leu Ser Ala Val Arg Phe Met Glu Glu Leu Gly
465                 470                 475                 480

Glu Cys Ala Phe Gly Lys Ile Tyr Lys Gly His Leu Tyr Leu Pro Gly
                485                 490                 495

Met Asp His Ala Gln Leu Val Ala Ile Lys Thr Leu Lys Asp Tyr Asn
            500                 505                 510

Asn Pro Gln Gln Trp Thr Glu Phe Gln Gln Glu Ala Ser Leu Met Ala
        515                 520                 525
```

```
Glu Leu His His Pro Asn Ile Val Cys Leu Leu Gly Ala Val Thr Gln
            530                 535                 540

Glu Gln Pro Val Cys Met Leu Phe Glu Tyr Ile Asn Gln Gly Asp Leu
545                 550                 555                 560

His Glu Phe Leu Ile Met Arg Ser Pro His Ser Asp Val Gly Cys Ser
                565                 570                 575

Ser Asp Glu Asp Gly Thr Val Lys Ser Ser Leu Asp His Gly Asp Phe
            580                 585                 590

Leu His Ile Ala Ile Gln Ile Ala Ala Gly Met Glu Tyr Leu Ser Ser
            595                 600                 605

His Phe Phe Val His Lys Asp Leu Ala Ala Arg Asn Ile Leu Ile Gly
            610                 615                 620

Glu Gln Leu His Val Lys Ile Ser Asp Leu Gly Leu Ser Arg Glu Ile
625                 630                 635                 640

Tyr Ser Ala Asp Tyr Tyr Arg Val Gln Ser Lys Ser Leu Leu Pro Ile
                645                 650                 655

Arg Trp Met Pro Pro Glu Ala Ile Met Tyr Gly Lys Phe Ser Ser Asp
                660                 665                 670

Ser Asp Ile Trp Ser Phe Gly Val Val Leu Trp Glu Ile Phe Ser Phe
            675                 680                 685

Gly Leu Gln Pro Tyr Tyr Gly Phe Ser Asn Gln Glu Val Ile Glu Met
            690                 695                 700

Val Arg Lys Arg Gln Leu Leu Pro Cys Ser Glu Asp Cys Pro Pro Arg
705                 710                 715                 720

Met Tyr Ser Leu Met Thr Glu Cys Trp Asn Glu Ile Pro Ser Arg Arg
                725                 730                 735

Pro Arg Phe Lys Asp Ile His Val Arg Leu Arg Ser Trp Glu Gly Leu
                740                 745                 750

Ser Ser His Thr Ser Ser Thr Thr Pro Ser Gly Gly Asn Ala Thr Thr
            755                 760                 765

Gln Thr Thr Ser Leu Ser Ala Ser Pro Val Ser Asn Leu Ser Asn Pro
            770                 775                 780

Arg Tyr Pro Asn Tyr Met Phe Pro Ser Gln Gly Ile Thr Pro Gln Gly
785                 790                 795                 800

Gln Ile Ala Gly Phe Ile Gly Pro Pro Ile Pro Gln Asn Gln Arg Phe
                805                 810                 815

Ile Pro Ile Asn Gly Tyr Pro Ile Pro Gly Tyr Ala Ala Phe Pro
                820                 825                 830

Ala Ala His Tyr Gln Pro Thr Gly Pro Pro Arg Val Ile Gln His Cys
            835                 840                 845

Pro Pro Pro Lys Ser Arg Ser Pro Ser Ser Ala Ser Gly Ser Thr Ser
850                 855                 860

Thr Gly His Val Thr Ser Leu Pro Ser Ser Gly Ser Asn Gln Glu Ala
865                 870                 875                 880

Asn Ile Pro Leu Leu Pro His Met Ser Ile Pro Asn His Pro Gly Gly
                885                 890                 895

Met Gly Ile Thr Val Phe Gly Asn Lys Ser Gln Lys Pro Tyr Lys Ile
                900                 905                 910

Asp Ser Lys Gln Ala Ser Leu Leu Gly Asp Ala Asn Ile His Gly His
            915                 920                 925

Thr Glu Ser Met Ile Ser Ala Glu Leu
            930                 935
```

```
<210> SEQ ID NO 9
<211> LENGTH: 937
<212> TYPE: PRT
<213> ORGANISM: Mus musculus

<400> SEQUENCE: 9

Met His Arg Pro Arg Arg Gly Thr Arg Pro Pro Leu Ala Leu
1               5                   10                  15

Leu Ala Ala Leu Leu Ala Ala Arg Gly Ala Asp Ala Gln Glu Thr
            20                  25                  30

Glu Leu Ser Val Ser Ala Glu Leu Val Pro Thr Ser Ser Trp Asn Thr
            35                  40                  45

Ser Ser Glu Ile Asp Lys Gly Ser Tyr Leu Thr Leu Asp Glu Pro Met
50                  55                  60

Asn Asn Ile Thr Thr Ser Leu Gly Gln Thr Ala Glu Leu His Cys Lys
65                  70                  75                  80

Val Ser Gly Asn Pro Pro Pro Ser Ile Arg Trp Phe Lys Asn Asp Ala
                85                  90                  95

Pro Val Val Gln Glu Pro Arg Arg Ile Ser Phe Arg Ala Thr Asn Tyr
            100                 105                 110

Gly Ser Arg Leu Arg Ile Arg Asn Leu Asp Thr Thr Asp Thr Gly Tyr
        115                 120                 125

Phe Gln Cys Val Ala Thr Asn Gly Lys Lys Val Val Ser Thr Thr Gly
130                 135                 140

Val Leu Phe Val Lys Phe Gly Pro Pro Thr Ala Ser Pro Gly Ser
145                 150                 155                 160

Ser Asp Glu Tyr Glu Glu Asp Gly Phe Cys Gln Pro Tyr Arg Gly Ile
                165                 170                 175

Ala Cys Ala Arg Phe Ile Gly Asn Arg Thr Val Tyr Met Glu Ser Leu
            180                 185                 190

His Met Gln Gly Glu Ile Glu Asn Gln Ile Thr Ala Ala Phe Thr Met
        195                 200                 205

Ile Gly Thr Ser Ser His Leu Ser Asp Lys Cys Ser Gln Phe Ala Ile
210                 215                 220

Pro Ser Leu Cys His Tyr Ala Phe Pro Tyr Cys Asp Glu Thr Ser Ser
225                 230                 235                 240

Val Pro Lys Pro Arg Asp Leu Cys Arg Asp Glu Cys Glu Val Leu Glu
                245                 250                 255

Asn Val Leu Cys Gln Thr Glu Tyr Ile Phe Ala Arg Ser Asn Pro Met
            260                 265                 270

Ile Leu Met Arg Leu Lys Leu Pro Asn Cys Glu Asp Leu Pro Gln Pro
        275                 280                 285

Glu Ser Pro Glu Ala Ala Asn Cys Ile Arg Ile Gly Ile Pro Met Ala
290                 295                 300

Asp Pro Ile Asn Lys Asn His Lys Cys Tyr Asn Ser Thr Gly Val Asp
305                 310                 315                 320

Tyr Arg Gly Thr Val Ser Val Thr Lys Ser Gly Arg Gln Cys Gln Pro
                325                 330                 335

Trp Asn Ser Gln Tyr Pro His Thr His Ser Phe Thr Ala Leu Arg Phe
            340                 345                 350

Pro Glu Leu Asn Gly Gly His Ser Tyr Cys Arg Asn Pro Gly Asn Gln
        355                 360                 365

Lys Glu Ala Pro Trp Cys Phe Thr Leu Asp Glu Asn Phe Lys Ser Asp
370                 375                 380
```

```
Leu Cys Asp Ile Pro Ala Cys Asp Ser Lys Asp Ser Lys Glu Lys Asn
385                 390                 395                 400

Lys Met Glu Ile Leu Tyr Ile Leu Val Pro Ser Val Ala Ile Pro Leu
            405                 410                 415

Ala Ile Ala Phe Leu Phe Phe Phe Ile Cys Val Cys Arg Asn Asn Gln
        420                 425                 430

Lys Ser Ser Ser Pro Pro Val Gln Arg Gln Pro Lys Pro Val Arg Gly
    435                 440                 445

Gln Asn Val Glu Met Ser Met Leu Asn Ala Tyr Lys Pro Lys Ser Lys
    450                 455                 460

Ala Lys Glu Leu Pro Leu Ser Ala Val Arg Phe Met Glu Glu Leu Gly
465                 470                 475                 480

Glu Cys Thr Phe Gly Lys Ile Tyr Lys Gly His Leu Tyr Leu Pro Gly
                485                 490                 495

Met Asp His Ala Gln Leu Val Ala Ile Lys Thr Leu Lys Asp Tyr Asn
            500                 505                 510

Asn Pro Gln Gln Trp Thr Glu Phe Gln Gln Glu Ala Ser Leu Met Ala
        515                 520                 525

Glu Leu His His Pro Asn Ile Val Cys Leu Leu Gly Ala Val Thr Gln
    530                 535                 540

Glu Gln Pro Val Cys Met Leu Phe Glu Tyr Met Asn Gln Gly Asp Leu
545                 550                 555                 560

His Glu Phe Leu Ile Met Arg Ser Pro His Ser Asp Val Gly Cys Ser
                565                 570                 575

Ser Asp Glu Asp Gly Thr Val Lys Ser Ser Leu Asp His Gly Asp Phe
            580                 585                 590

Leu His Ile Ala Ile Gln Ile Ala Ala Gly Met Glu Tyr Leu Ser Ser
        595                 600                 605

His Phe Phe Val His Lys Asp Leu Ala Ala Arg Asn Ile Leu Ile Gly
    610                 615                 620

Glu Gln Leu His Val Lys Ile Ser Asp Leu Gly Leu Ser Arg Glu Ile
625                 630                 635                 640

Tyr Ser Ala Asp Tyr Tyr Arg Val Gln Ser Lys Ser Ser Leu Pro Ile
                645                 650                 655

Arg Trp Met Pro Pro Glu Ala Ile Met Tyr Gly Lys Phe Ser Ser Asp
            660                 665                 670

Ser Asp Ile Trp Ser Phe Gly Val Val Leu Trp Glu Ile Phe Ser Phe
        675                 680                 685

Gly Leu Gln Pro Tyr Tyr Gly Phe Ser Asn Gln Glu Val Ile Glu Met
    690                 695                 700

Val Arg Lys Arg Gln Leu Leu Pro Cys Ser Glu Asp Cys Pro Pro Arg
705                 710                 715                 720

Met Tyr Ser Leu Met Thr Glu Cys Trp Asn Glu Ile Pro Ser Arg Arg
                725                 730                 735

Pro Arg Phe Lys Asp Ile His Val Arg Leu Arg Ser Trp Glu Gly Leu
            740                 745                 750

Ser Ser His Thr Ser Ser Thr Thr Pro Ser Gly Gly Asn Ala Thr Thr
        755                 760                 765

Gln Thr Thr Ser Leu Ser Ala Ser Pro Val Ser Asn Leu Ser Asn Pro
    770                 775                 780

Arg Phe Pro Asn Tyr Met Phe Pro Ser Gln Gly Ile Thr Pro Gln Gly
785                 790                 795                 800
```

```
Gln Ile Ala Gly Phe Ile Gly Pro Ala Ile Pro Gln Asn Gln Arg Phe
            805                 810                 815

Ile Pro Ile Asn Gly Tyr Pro Ile Pro Pro Gly Tyr Ala Ala Phe Pro
            820                 825                 830

Ala Ala His Tyr Gln Pro Ala Gly Pro Pro Arg Val Ile Gln His Cys
            835                 840                 845

Pro Pro Pro Lys Ser Arg Ser Pro Ser Ser Ala Ser Gly Ser Thr Ser
850                 855                 860

Thr Gly His Val Ala Ser Leu Pro Ser Ser Gly Ser Asn Gln Glu Ala
865                 870                 875                 880

Asn Val Pro Leu Leu Pro His Met Ser Ile Pro Asn His Pro Gly Gly
                885                 890                 895

Met Gly Ile Thr Val Phe Gly Asn Lys Ser Gln Lys Pro Tyr Lys Ile
            900                 905                 910

Asp Ser Lys Gln Ser Ser Leu Leu Gly Asp Ser His Ile His Gly His
            915                 920                 925

Thr Glu Ser Met Ile Ser Ala Glu Val
            930                 935

<210> SEQ ID NO 10
<211> LENGTH: 943
<212> TYPE: PRT
<213> ORGANISM: Homo sapiens

<400> SEQUENCE: 10

Met Ala Arg Gly Ser Ala Leu Pro Arg Arg Pro Leu Leu Cys Ile Pro
1               5                   10                  15

Ala Val Trp Ala Ala Ala Leu Leu Leu Ser Val Ser Arg Thr Ser
            20                  25                  30

Gly Glu Val Glu Val Leu Asp Pro Asn Asp Pro Leu Gly Pro Leu Asp
            35                  40                  45

Gly Gln Asp Gly Pro Ile Pro Thr Leu Lys Gly Tyr Phe Leu Asn Phe
        50                  55                  60

Leu Glu Pro Val Asn Asn Ile Thr Ile Val Gln Gly Gln Thr Ala Ile
65              70                  75                  80

Leu His Cys Lys Val Ala Gly Asn Pro Pro Pro Asn Val Arg Trp Leu
                85                  90                  95

Lys Asn Asp Ala Pro Val Val Gln Glu Pro Arg Arg Ile Ile Ile Arg
            100                 105                 110

Lys Thr Glu Tyr Gly Ser Arg Leu Arg Ile Gln Asp Leu Asp Thr Thr
            115                 120                 125

Asp Thr Gly Tyr Tyr Gln Cys Val Ala Thr Asn Gly Met Lys Thr Ile
        130                 135                 140

Thr Ala Thr Gly Val Leu Phe Val Arg Leu Gly Pro Thr His Ser Pro
145                 150                 155                 160

Asn His Asn Phe Gln Asp Asp Tyr His Glu Asp Gly Phe Cys Gln Pro
                165                 170                 175

Tyr Arg Gly Ile Ala Cys Ala Arg Phe Ile Gly Asn Arg Thr Ile Tyr
            180                 185                 190

Val Asp Ser Leu Gln Met Gln Gly Glu Ile Glu Asn Arg Ile Thr Ala
            195                 200                 205

Ala Phe Thr Met Ile Gly Thr Ser Thr His Leu Ser Asp Gln Cys Ser
        210                 215                 220

Gln Phe Ala Ile Pro Ser Phe Cys His Phe Val Phe Pro Leu Cys Asp
225                 230                 235                 240
```

```
Ala Arg Ser Arg Thr Pro Lys Pro Arg Glu Leu Cys Arg Asp Glu Cys
                245                 250                 255

Glu Val Leu Glu Ser Asp Leu Cys Arg Gln Glu Tyr Thr Ile Ala Arg
            260                 265                 270

Ser Asn Pro Leu Ile Leu Met Arg Leu Gln Leu Pro Lys Cys Glu Ala
        275                 280                 285

Leu Pro Met Pro Glu Ser Pro Asp Ala Ala Asn Cys Met Arg Ile Gly
    290                 295                 300

Ile Pro Ala Glu Arg Leu Gly Arg Tyr His Gln Cys Tyr Asn Gly Ser
305                 310                 315                 320

Gly Met Asp Tyr Arg Gly Thr Ala Ser Thr Thr Lys Ser Gly His Gln
                325                 330                 335

Cys Gln Pro Trp Ala Leu Gln His Pro His Ser His His Leu Ser Ser
            340                 345                 350

Thr Asp Phe Pro Glu Leu Gly Gly Gly His Ala Tyr Cys Arg Asn Pro
        355                 360                 365

Gly Gly Gln Met Glu Gly Pro Trp Cys Phe Thr Gln Asn Lys Asn Val
    370                 375                 380

Arg Met Glu Leu Cys Asp Val Pro Ser Cys Ser Pro Arg Asp Ser Ser
385                 390                 395                 400

Lys Met Gly Ile Leu Tyr Ile Leu Val Pro Ser Ile Ala Ile Pro Leu
                405                 410                 415

Val Ile Ala Cys Leu Phe Phe Leu Val Cys Met Cys Arg Asn Lys Gln
            420                 425                 430

Lys Ala Ser Ala Ser Thr Pro Gln Arg Arg Gln Leu Met Ala Ser Pro
        435                 440                 445

Ser Gln Asp Met Glu Met Pro Leu Ile Asn Gln His Lys Gln Ala Lys
    450                 455                 460

Leu Lys Glu Ile Ser Leu Ser Ala Val Arg Phe Met Glu Glu Leu Gly
465                 470                 475                 480

Glu Asp Arg Phe Gly Lys Val Tyr Lys Gly His Leu Phe Gly Pro Ala
                485                 490                 495

Pro Gly Glu Gln Thr Gln Ala Val Ala Ile Lys Thr Leu Lys Asp Lys
            500                 505                 510

Ala Glu Gly Pro Leu Arg Glu Glu Phe Arg His Glu Ala Met Leu Arg
        515                 520                 525

Ala Arg Leu Gln His Pro Asn Val Val Cys Leu Leu Gly Val Val Thr
    530                 535                 540

Lys Asp Gln Pro Leu Ser Met Ile Phe Ser Tyr Cys Ser His Gly Asp
545                 550                 555                 560

Leu His Glu Phe Leu Val Met Arg Ser Pro His Ser Asp Val Gly Ser
                565                 570                 575

Thr Asp Asp Asp Arg Thr Val Lys Ser Ala Leu Glu Pro Pro Asp Phe
            580                 585                 590

Val His Leu Val Ala Gln Ile Ala Ala Gly Met Glu Tyr Leu Ser Ser
        595                 600                 605

His His Val Val His Lys Asp Leu Ala Thr Arg Asn Val Leu Val Tyr
    610                 615                 620

Asp Lys Leu Asn Val Lys Ile Ser Asp Leu Gly Leu Phe Arg Glu Val
625                 630                 635                 640

Tyr Ala Ala Asp Tyr Tyr Lys Leu Leu Gly Asn Ser Leu Leu Pro Ile
                645                 650                 655
```

-continued

```
Arg Trp Met Ala Pro Glu Ala Ile Met Tyr Gly Lys Phe Ser Ile Asp
            660                 665                 670

Ser Asp Ile Trp Ser Tyr Gly Val Val Leu Trp Glu Val Phe Ser Tyr
        675                 680                 685

Gly Leu Gln Pro Tyr Cys Gly Tyr Ser Asn Gln Asp Val Val Glu Met
        690                 695                 700

Ile Arg Asn Arg Gln Val Leu Pro Cys Pro Asp Asp Cys Pro Ala Trp
705                 710                 715                 720

Val Tyr Ala Leu Met Ile Glu Cys Trp Asn Glu Phe Pro Ser Arg Arg
                725                 730                 735

Pro Arg Phe Lys Asp Ile His Ser Arg Leu Arg Ala Trp Gly Asn Leu
            740                 745                 750

Ser Asn Tyr Asn Ser Ser Ala Gln Thr Ser Gly Ala Ser Asn Thr Thr
        755                 760                 765

Gln Thr Ser Ser Leu Ser Thr Ser Pro Val Ser Asn Val Ser Asn Ala
        770                 775                 780

Arg Tyr Val Gly Pro Lys Gln Lys Ala Pro Pro Phe Pro Gln Pro Gln
785                 790                 795                 800

Phe Ile Pro Met Lys Gly Gln Ile Arg Pro Met Val Pro Pro Gln
                805                 810                 815

Leu Tyr Val Pro Val Asn Gly Tyr Gln Pro Val Pro Ala Tyr Gly Ala
            820                 825                 830

Tyr Leu Pro Asn Phe Tyr Pro Val Gln Ile Pro Met Gln Met Ala Pro
        835                 840                 845

Gln Gln Val Pro Pro Gln Met Val Pro Lys Pro Ser Ser His His Ser
        850                 855                 860

Gly Ser Gly Ser Thr Ser Thr Gly Tyr Val Thr Thr Ala Pro Ser Asn
865                 870                 875                 880

Thr Ser Met Ala Asp Arg Ala Ala Leu Leu Ser Glu Gly Ala Asp Asp
                885                 890                 895

Thr Gln Asn Ala Pro Glu Asp Gly Ala Gln Ser Thr Val Gln Glu Ala
            900                 905                 910

Glu Glu Glu Glu Glu Gly Ser Val Pro Glu Thr Glu Leu Leu Gly Asp
        915                 920                 925

Cys Asp Thr Leu Gln Val Asp Glu Ala Gln Val Gln Leu Glu Ala
        930                 935                 940

<210> SEQ ID NO 11
<211> LENGTH: 944
<212> TYPE: PRT
<213> ORGANISM: Mus musculus

<400> SEQUENCE: 11

Met Ala Arg Gly Trp Val Arg Pro Ser Arg Val Pro Leu Cys Ala Arg
1               5                   10                  15

Ala Val Trp Thr Ala Ala Ala Leu Leu Leu Trp Thr Pro Trp Thr Ala
            20                  25                  30

Gly Glu Val Glu Asp Ser Glu Ala Ile Asp Thr Leu Gly Gln Pro Asp
        35                  40                  45

Gly Pro Asp Ser Pro Leu Pro Thr Leu Lys Gly Tyr Phe Leu Asn Phe
    50                  55                  60

Leu Glu Pro Val Asn Asn Ile Thr Ile Val Gln Gly Gln Thr Ala Ile
65                  70                  75                  80

Leu His Cys Lys Val Ala Gly Asn Pro Pro Pro Asn Val Arg Trp Leu
                85                  90                  95
```

-continued

```
Lys Asn Asp Ala Pro Val Val Gln Glu Pro Arg Arg Val Ile Ile Arg
                100                 105                 110

Lys Thr Glu Tyr Gly Ser Arg Leu Arg Ile Gln Asp Leu Asp Thr Thr
            115                 120                 125

Asp Thr Gly Tyr Tyr Gln Cys Val Ala Thr Asn Gly Leu Lys Thr Ile
        130                 135                 140

Thr Ala Thr Gly Val Leu Tyr Val Arg Leu Gly Pro Thr His Ser Pro
145                 150                 155                 160

Asn His Asn Phe Gln Asp Asp Gln Glu Asp Gly Phe Cys Gln Pro
                165                 170                 175

Tyr Arg Gly Ile Ala Cys Ala Arg Phe Ile Gly Asn Arg Thr Ile Tyr
            180                 185                 190

Val Asp Ser Leu Gln Met Gln Gly Glu Ile Glu Asn Arg Ile Thr Ala
        195                 200                 205

Ala Phe Thr Met Ile Gly Thr Ser Thr Gln Leu Ser Asp Gln Cys Ser
210                 215                 220

Gln Phe Ala Ile Pro Ser Phe Cys His Phe Val Phe Pro Leu Cys Asp
225                 230                 235                 240

Ala Arg Ser Arg Ala Pro Lys Pro Arg Glu Leu Cys Arg Asp Glu Cys
            245                 250                 255

Glu Val Leu Glu Asn Asp Leu Cys Arg Gln Glu Tyr Thr Ile Ala Arg
        260                 265                 270

Ser Asn Pro Leu Ile Leu Met Arg Leu Gln Leu Pro Lys Cys Glu Ala
            275                 280                 285

Leu Pro Met Pro Glu Ser Pro Asp Ala Ala Asn Cys Met Arg Ile Gly
290                 295                 300

Ile Pro Ala Glu Arg Leu Gly Arg Tyr His Gln Cys Tyr Asn Gly Ser
305                 310                 315                 320

Gly Ala Asp Tyr Arg Gly Met Ala Ser Thr Thr Lys Ser Gly His Gln
            325                 330                 335

Cys Gln Pro Trp Ala Leu Gln His Pro His Ser His Arg Leu Ser Ser
        340                 345                 350

Thr Glu Phe Pro Glu Leu Gly Gly Gly His Ala Tyr Cys Arg Asn Pro
            355                 360                 365

Gly Gly Gln Val Glu Gly Pro Trp Cys Phe Thr Gln Asn Lys Asn Val
        370                 375                 380

Arg Val Glu Leu Cys Asp Val Pro Pro Cys Ser Pro Arg Asp Gly Ser
385                 390                 395                 400

Lys Met Gly Ile Leu Tyr Ile Leu Val Pro Ser Ile Ala Ile Pro Leu
            405                 410                 415

Val Ile Ala Cys Leu Phe Phe Leu Val Cys Met Cys Arg Asn Lys Gln
        420                 425                 430

Lys Ala Ser Ala Ser Thr Pro Gln Arg Arg Gln Leu Met Ala Ser Pro
            435                 440                 445

Ser Gln Asp Met Glu Met Pro Leu Ile Ser Gln His Lys Gln Ala Lys
        450                 455                 460

Leu Lys Glu Ile Ser Leu Ser Thr Val Arg Phe Met Glu Glu Leu Gly
465                 470                 475                 480

Glu Asp Arg Phe Gly Lys Val Tyr Lys Gly His Leu Phe Gly Pro Ala
            485                 490                 495

Pro Gly Glu Pro Thr Gln Ala Val Ala Ile Lys Thr Leu Lys Asp Lys
        500                 505                 510
```

```
Ala Glu Gly Pro Leu Arg Glu Glu Phe Arg Gln Glu Ala Met Leu Arg
            515                 520                 525

Ala Arg Leu Gln His Pro Asn Ile Val Cys Leu Leu Gly Val Val Thr
        530                 535                 540

Lys Asp Gln Pro Leu Ser Met Ile Phe Ser Tyr Cys Ser His Gly Asp
545                 550                 555                 560

Leu His Glu Phe Leu Val Met Arg Ser Pro His Ser Asp Val Gly Ser
                565                 570                 575

Thr Asp Asp Asp Arg Thr Val Lys Ser Ala Leu Glu Pro Pro Asp Phe
            580                 585                 590

Val His Val Val Ala Gln Ile Ala Ala Gly Met Glu Phe Leu Ser Ser
        595                 600                 605

His His Val Val His Lys Asp Leu Ala Thr Arg Asn Val Leu Val Tyr
    610                 615                 620

Asp Lys Leu Asn Val Arg Ile Ser Asp Leu Gly Leu Phe Arg Glu Val
625                 630                 635                 640

Tyr Ser Ala Asp Tyr Tyr Lys Leu Met Gly Asn Ser Leu Leu Pro Ile
                645                 650                 655

Arg Trp Met Ser Pro Glu Ala Val Met Tyr Gly Lys Phe Ser Ile Asp
            660                 665                 670

Ser Asp Ile Trp Ser Tyr Gly Val Val Leu Trp Glu Val Phe Ser Tyr
        675                 680                 685

Gly Leu Gln Pro Tyr Cys Gly Tyr Ser Asn Gln Asp Val Val Glu Met
    690                 695                 700

Ile Arg Ser Arg Gln Val Leu Pro Cys Pro Asp Asp Cys Pro Ala Trp
705                 710                 715                 720

Val Tyr Ala Leu Met Ile Glu Cys Trp Asn Glu Phe Pro Ser Arg Arg
                725                 730                 735

Pro Arg Phe Lys Asp Ile His Ser Arg Leu Arg Ser Trp Gly Asn Leu
            740                 745                 750

Ser Asn Tyr Asn Ser Ser Ala Gln Thr Ser Gly Ala Ser Asn Thr Thr
        755                 760                 765

Gln Thr Ser Ser Leu Ser Thr Ser Pro Val Ser Asn Val Ser Asn Ala
    770                 775                 780

Arg Tyr Met Ala Pro Lys Gln Lys Ala Gln Pro Phe Pro Gln Pro Gln
785                 790                 795                 800

Phe Ile Pro Met Lys Gly Gln Ile Arg Pro Leu Val Pro Pro Ala Gln
                805                 810                 815

Leu Tyr Ile Pro Val Asn Gly Tyr Gln Pro Val Pro Ala Tyr Gly Ala
            820                 825                 830

Tyr Leu Pro Asn Phe Tyr Pro Val Gln Ile Pro Met Gln Met Ala Pro
        835                 840                 845

Gln Gln Val Pro Pro Gln Met Val Pro Lys Pro Ser Ser His His Ser
    850                 855                 860

Gly Ser Gly Ser Thr Ser Thr Gly Tyr Val Thr Thr Ala Pro Ser Asn
865                 870                 875                 880

Thr Ser Val Ala Asp Arg Ala Ala Leu Leu Ser Glu Gly Thr Glu Asp
                885                 890                 895

Ala Gln Asn Ile Ala Glu Asp Val Ala Gln Ser Pro Val Gln Glu Ala
            900                 905                 910
```

Glu Glu Glu Glu Gly Ser Val Pro Glu Thr Glu Leu Leu Gly Asp
            915                 920                 925

Asn Asp Thr Leu Gln Val Thr Glu Ala Ala His Val Gln Leu Glu Ala
    930                 935                 940

<210> SEQ ID NO 12
<211> LENGTH: 380
<212> TYPE: PRT
<213> ORGANISM: Homo sapiens

<400> SEQUENCE: 12

Met Lys Lys Ser Ile Gly Ile Leu Ser Pro Gly Val Ala Leu Gly Met
1               5                   10                  15

Ala Gly Ser Ala Met Ser Ser Lys Phe Phe Leu Val Ala Leu Ala Ile
            20                  25                  30

Phe Phe Ser Phe Ala Gln Val Val Ile Glu Ala Asn Ser Trp Trp Ser
        35                  40                  45

Leu Gly Met Asn Asn Pro Val Gln Met Ser Glu Val Tyr Ile Ile Gly
    50                  55                  60

Ala Gln Pro Leu Cys Ser Gln Leu Ala Gly Leu Ser Gln Gly Gln Lys
65                  70                  75                  80

Lys Leu Cys His Leu Tyr Gln Asp His Met Gln Tyr Ile Gly Glu Gly
                85                  90                  95

Ala Lys Thr Gly Ile Lys Glu Cys Gln Tyr Gln Phe Arg His Arg Arg
            100                 105                 110

Trp Asn Cys Ser Thr Val Asp Asn Thr Ser Val Phe Gly Arg Val Met
        115                 120                 125

Gln Ile Gly Ser Arg Glu Thr Ala Phe Thr Tyr Ala Val Ser Ala Ala
    130                 135                 140

Gly Val Val Asn Ala Met Ser Arg Ala Cys Arg Glu Gly Glu Leu Ser
145                 150                 155                 160

Thr Cys Gly Cys Ser Arg Ala Ala Arg Pro Lys Asp Leu Pro Arg Asp
                165                 170                 175

Trp Leu Trp Gly Gly Cys Gly Asp Asn Ile Asp Tyr Gly Tyr Arg Phe
            180                 185                 190

Ala Lys Glu Phe Val Asp Ala Arg Glu Arg Glu Arg Ile His Ala Lys
        195                 200                 205

Gly Ser Tyr Glu Ser Ala Arg Ile Leu Met Asn Leu His Asn Asn Glu
    210                 215                 220

Ala Gly Arg Arg Thr Val Tyr Asn Leu Ala Asp Val Ala Cys Lys Cys
225                 230                 235                 240

His Gly Val Ser Gly Ser Cys Ser Leu Lys Thr Cys Trp Leu Gln Leu
                245                 250                 255

Ala Asp Phe Arg Lys Val Gly Asp Ala Leu Lys Glu Lys Tyr Asp Ser
            260                 265                 270

Ala Ala Ala Met Arg Leu Asn Ser Arg Gly Lys Leu Val Gln Val Asn
        275                 280                 285

Ser Arg Phe Asn Ser Pro Thr Thr Gln Asp Leu Val Tyr Ile Asp Pro
    290                 295                 300

Ser Pro Asp Tyr Cys Val Arg Asn Glu Ser Thr Gly Ser Leu Gly Thr
305                 310                 315                 320

Gln Gly Arg Leu Cys Asn Lys Thr Ser Glu Gly Met Asp Gly Cys Glu
                325                 330                 335

Leu Met Cys Cys Gly Arg Gly Tyr Asp Gln Phe Lys Thr Val Gln Thr
            340                 345                 350

Glu Arg Cys His Cys Lys Phe His Trp Cys Cys Tyr Val Lys Cys Lys
            355                 360                 365

Lys Cys Thr Glu Ile Val Asp Gln Phe Val Cys Lys
370                 375                 380

<210> SEQ ID NO 13
<211> LENGTH: 380
<212> TYPE: PRT
<213> ORGANISM: Mus musculus

<400> SEQUENCE: 13

Met Lys Lys Pro Ile Gly Ile Leu Ser Pro Gly Val Ala Leu Gly Thr
1               5                   10                  15

Ala Gly Gly Ala Met Ser Ser Lys Phe Phe Leu Met Ala Leu Ala Thr
            20                  25                  30

Phe Phe Ser Phe Ala Gln Val Val Ile Glu Ala Asn Ser Trp Trp Ser
        35                  40                  45

Leu Gly Met Asn Asn Pro Val Gln Met Ser Glu Val Tyr Ile Ile Gly
50                  55                  60

Ala Gln Pro Leu Cys Ser Gln Leu Ala Gly Leu Ser Gln Gly Gln Lys
65                  70                  75                  80

Lys Leu Cys His Leu Tyr Gln Asp His Met Gln Tyr Ile Gly Glu Gly
                85                  90                  95

Ala Lys Thr Gly Ile Lys Glu Cys Gln Tyr Gln Phe Arg His Arg Arg
            100                 105                 110

Trp Asn Cys Ser Thr Val Asp Asn Thr Ser Val Phe Gly Arg Val Met
        115                 120                 125

Gln Ile Gly Ser Arg Glu Thr Ala Phe Thr Tyr Ala Val Ser Ala Ala
130                 135                 140

Gly Val Val Asn Ala Met Ser Arg Ala Cys Arg Glu Gly Glu Leu Ser
145                 150                 155                 160

Thr Cys Gly Cys Ser Arg Ala Ala Arg Pro Lys Asp Leu Pro Arg Asp
                165                 170                 175

Trp Leu Trp Gly Gly Cys Gly Asp Asn Ile Asp Tyr Gly Tyr Arg Phe
            180                 185                 190

Ala Lys Glu Phe Val Asp Ala Arg Glu Arg Glu Arg Ile His Ala Lys
        195                 200                 205

Gly Ser Tyr Glu Ser Ala Arg Ile Leu Met Asn Leu His Asn Asn Glu
210                 215                 220

Ala Gly Arg Arg Thr Val Tyr Asn Leu Ala Asp Val Ala Cys Lys Cys
225                 230                 235                 240

His Gly Val Ser Gly Ser Cys Ser Leu Lys Thr Cys Trp Leu Gln Leu
                245                 250                 255

Ala Asp Phe Arg Lys Val Gly Asp Ala Leu Lys Glu Lys Tyr Asp Ser
            260                 265                 270

Ala Ala Ala Met Arg Leu Asn Ser Arg Gly Lys Leu Val Gln Val Asn
        275                 280                 285

Ser Arg Phe Asn Ser Pro Thr Thr Gln Asp Leu Val Tyr Ile Asp Pro
290                 295                 300

Ser Pro Asp Tyr Cys Val Arg Asn Glu Ser Thr Gly Ser Leu Gly Thr
305                 310                 315                 320

Gln Gly Arg Leu Cys Asn Lys Thr Ser Glu Gly Met Asp Gly Cys Glu
                325                 330                 335

Leu Met Cys Cys Gly Arg Gly Tyr Asp Gln Phe Lys Thr Val Gln Thr
            340                 345                 350

```
Glu Arg Cys His Cys Lys Phe His Trp Cys Cys Tyr Val Lys Cys Lys
        355                 360                 365

Lys Cys Thr Glu Ile Val Asp Gln Phe Val Cys Lys
    370                 375                 380

<210> SEQ ID NO 14
<211> LENGTH: 193
<212> TYPE: PRT
<213> ORGANISM: Homo sapiens

<400> SEQUENCE: 14

Met Ala Ala Ile Arg Lys Lys Leu Val Ile Val Gly Asp Gly Ala Cys
1               5                   10                  15

Gly Lys Thr Cys Leu Leu Ile Val Phe Ser Lys Asp Gln Phe Pro Glu
            20                  25                  30

Val Tyr Val Pro Thr Val Phe Glu Asn Tyr Val Ala Asp Ile Glu Val
        35                  40                  45

Asp Gly Lys Gln Val Glu Leu Ala Leu Trp Asp Thr Ala Gly Gln Glu
65                  55                  60

Asp Tyr Asp Arg Leu Arg Pro Leu Ser Tyr Pro Asp Thr Asp Val Ile
65                  70                  75                  80

Leu Met Cys Phe Ser Ile Asp Ser Pro Asp Ser Leu Glu Asn Ile Pro
                85                  90                  95

Glu Lys Trp Thr Pro Glu Val Lys His Phe Cys Pro Asn Val Pro Ile
            100                 105                 110

Ile Leu Val Gly Asn Lys Lys Asp Leu Arg Asn Asp Glu His Thr Arg
        115                 120                 125

Arg Glu Leu Ala Lys Met Lys Gln Glu Pro Val Lys Pro Glu Glu Gly
    130                 135                 140

Arg Asp Met Ala Asn Arg Ile Gly Ala Phe Gly Tyr Met Glu Cys Ser
145                 150                 155                 160

Ala Lys Thr Lys Asp Gly Val Arg Glu Val Phe Glu Met Ala Thr Arg
                165                 170                 175

Ala Ala Leu Gln Ala Arg Arg Gly Lys Lys Lys Ser Gly Cys Leu Val
            180                 185                 190

Leu

<210> SEQ ID NO 15
<211> LENGTH: 193
<212> TYPE: PRT
<213> ORGANISM: Mus musculus

<400> SEQUENCE: 15

Met Ala Ala Ile Arg Lys Lys Leu Val Ile Val Gly Asp Gly Ala Cys
1               5                   10                  15

Gly Lys Thr Cys Leu Leu Ile Val Phe Ser Lys Asp Gln Phe Pro Glu
            20                  25                  30

Val Tyr Val Pro Thr Val Phe Glu Asn Tyr Val Ala Asp Ile Glu Val
        35                  40                  45

Asp Gly Lys Gln Val Glu Leu Ala Leu Trp Asp Thr Ala Gly Gln Glu
    50                  55                  60

Asp Tyr Asp Arg Leu Arg Pro Leu Ser Tyr Pro Asp Thr Asp Val Ile
65                  70                  75                  80

Leu Met Cys Phe Ser Ile Asp Ser Pro Asp Ser Leu Glu Asn Ile Pro
                85                  90                  95
```

```
Glu Lys Trp Thr Pro Glu Val Lys His Phe Cys Pro Asn Val Pro Ile
                100                 105                 110

Ile Leu Val Gly Asn Lys Asp Leu Arg Asn Asp Glu His Thr Arg
            115                 120                 125

Arg Glu Leu Ala Lys Met Lys Gln Glu Pro Val Lys Pro Glu Glu Gly
        130                 135                 140

Arg Asp Met Ala Asn Arg Ile Gly Ala Phe Gly Tyr Met Glu Cys Ser
145                 150                 155                 160

Ala Lys Thr Lys Asp Gly Val Arg Glu Val Phe Glu Met Ala Thr Arg
                165                 170                 175

Ala Ala Leu Gln Ala Arg Arg Gly Lys Lys Lys Ser Gly Cys Leu Ile
            180                 185                 190

Leu

<210> SEQ ID NO 16
<211> LENGTH: 192
<212> TYPE: PRT
<213> ORGANISM: Homo sapiens

<400> SEQUENCE: 16

Met Gln Ala Ile Lys Cys Val Val Gly Asp Gly Ala Val Gly Lys
1               5                   10                  15

Thr Cys Leu Leu Ile Ser Tyr Thr Thr Asn Ala Phe Pro Gly Glu Tyr
            20                  25                  30

Ile Pro Thr Val Phe Asp Asn Tyr Ser Ala Asn Val Met Val Asp Gly
        35                  40                  45

Lys Pro Val Asn Leu Gly Leu Trp Asp Thr Ala Gly Gln Glu Asp Tyr
50                  55                  60

Asp Arg Leu Arg Pro Leu Ser Tyr Pro Gln Thr Asp Val Phe Leu Ile
65                  70                  75                  80

Cys Phe Ser Leu Val Ser Pro Ala Ser Phe Glu Asn Val Arg Ala Lys
                85                  90                  95

Trp Tyr Pro Glu Val Arg His His Cys Pro Asn Thr Pro Ile Ile Leu
                100                 105                 110

Val Gly Thr Lys Leu Asp Leu Arg Asp Asp Lys Asp Thr Ile Glu Lys
            115                 120                 125

Leu Lys Glu Lys Lys Leu Thr Pro Ile Thr Tyr Pro Gln Gly Leu Ala
        130                 135                 140

Met Ala Lys Glu Ile Gly Ala Val Lys Tyr Leu Glu Cys Ser Ala Leu
145                 150                 155                 160

Thr Gln Arg Gly Leu Lys Thr Val Phe Asp Glu Ala Ile Arg Ala Val
                165                 170                 175

Leu Cys Pro Pro Pro Val Lys Lys Arg Lys Arg Lys Cys Leu Leu Leu
            180                 185                 190

<210> SEQ ID NO 17
<211> LENGTH: 192
<212> TYPE: PRT
<213> ORGANISM: Mus musculus

<400> SEQUENCE: 17

Met Gln Ala Ile Lys Cys Val Val Gly Asp Gly Ala Val Gly Lys
1               5                   10                  15

Thr Cys Leu Leu Ile Ser Tyr Thr Thr Asn Ala Phe Pro Gly Glu Tyr
            20                  25                  30
```

-continued

```
Ile Pro Thr Val Phe Asp Asn Tyr Ser Ala Asn Val Met Val Asp Gly
            35                  40                  45

Lys Pro Val Asn Leu Gly Leu Trp Asp Thr Ala Gly Gln Glu Asp Tyr
 50                  55                  60

Asp Arg Leu Arg Pro Leu Ser Tyr Pro Gln Thr Asp Val Phe Leu Ile
 65                  70                  75                  80

Cys Phe Ser Leu Val Ser Pro Ala Ser Phe Glu Asn Val Arg Ala Lys
                 85                  90                  95

Trp Tyr Pro Glu Val Arg His His Cys Pro Asn Thr Pro Ile Ile Leu
                100                 105                 110

Val Gly Thr Lys Leu Asp Leu Arg Asp Asp Lys Asp Thr Ile Glu Lys
            115                 120                 125

Leu Lys Glu Lys Lys Leu Thr Pro Ile Thr Tyr Pro Gln Gly Leu Ala
130                 135                 140

Met Ala Lys Glu Ile Gly Ala Val Lys Tyr Leu Glu Cys Ser Ala Leu
145                 150                 155                 160

Thr Gln Arg Gly Leu Lys Thr Val Phe Asp Glu Ala Ile Arg Ala Val
                165                 170                 175

Leu Cys Pro Pro Pro Val Lys Lys Arg Lys Arg Lys Cys Leu Leu Leu
                180                 185                 190
```

<210> SEQ ID NO 18
<211> LENGTH: 912
<212> TYPE: PRT
<213> ORGANISM: Homo sapiens

<400> SEQUENCE: 18

```
Met Glu Asp Phe Ala Arg Gly Ala Ala Ser Pro Gly Pro Ser Arg Pro
  1               5                  10                  15

Gly Leu Val Pro Val Ser Ile Ile Gly Ala Glu Asp Glu Asp Phe Glu
                 20                  25                  30

Asn Glu Leu Glu Thr Asn Ser Glu Gln Asn Ser Gln Phe Gln Ser
             35                  40                  45

Leu Glu Gln Val Lys Arg Arg Pro Ala His Leu Met Ala Leu Leu Gln
 50                  55                  60

His Val Ala Leu Gln Phe Glu Pro Gly Pro Leu Leu Cys Cys Leu His
 65                  70                  75                  80

Ala Asp Met Leu Gly Ser Leu Gly Pro Lys Glu Ala Lys Lys Ala Phe
                 85                  90                  95

Leu Asp Phe Tyr His Ser Phe Leu Glu Lys Thr Ala Val Leu Arg Val
                100                 105                 110

Pro Val Pro Pro Asn Val Ala Phe Glu Leu Asp Arg Thr Arg Ala Asp
            115                 120                 125

Leu Ile Ser Glu Asp Val Gln Arg Arg Phe Val Gln Glu Val Val Gln
130                 135                 140

Ser Gln Gln Val Ala Val Gly Arg Gln Leu Glu Asp Phe Arg Ser Lys
145                 150                 155                 160

Arg Leu Met Gly Met Thr Pro Trp Glu Gln Glu Leu Ala Gln Leu Glu
                165                 170                 175

Ala Trp Val Gly Arg Asp Arg Ala Ser Tyr Glu Ala Arg Glu Arg His
                180                 185                 190

Val Ala Glu Arg Leu Leu Met His Leu Glu Glu Met Gln His Thr Ile
            195                 200                 205

Ser Thr Asp Glu Glu Lys Ser Ala Ala Val Val Asn Ala Ile Gly Leu
210                 215                 220
```

-continued

```
Tyr Met Arg His Leu Gly Val Arg Thr Lys Ser Gly Asp Lys Lys Ser
225                 230                 235                 240

Gly Arg Asn Phe Phe Arg Lys Lys Val Met Gly Asn Arg Arg Ser Asp
            245                 250                 255

Glu Pro Ala Lys Thr Lys Lys Gly Leu Ser Ser Ile Leu Asp Ala Ala
            260                 265                 270

Arg Trp Asn Arg Gly Glu Pro Gln Val Pro Asp Phe Arg His Leu Lys
        275                 280                 285

Ala Glu Val Asp Ala Glu Lys Pro Gly Ala Thr Asp Arg Lys Gly Gly
    290                 295                 300

Val Gly Met Pro Ser Arg Asp Arg Asn Ile Gly Ala Pro Gly Gln Asp
305                 310                 315                 320

Thr Pro Gly Val Ser Leu His Pro Leu Ser Leu Asp Ser Pro Asp Arg
                325                 330                 335

Glu Pro Gly Ala Asp Ala Pro Leu Glu Leu Gly Asp Ser Ser Pro Gln
            340                 345                 350

Gly Pro Met Ser Leu Glu Ser Leu Ala Pro Pro Glu Ser Thr Asp Glu
        355                 360                 365

Gly Ala Glu Thr Glu Ser Pro Glu Pro Gly Asp Glu Gly Glu Pro Gly
    370                 375                 380

Arg Ser Gly Leu Glu Leu Glu Pro Glu Glu Pro Pro Gly Trp Arg Glu
385                 390                 395                 400

Leu Val Pro Pro Asp Thr Leu His Ser Leu Pro Lys Ser Gln Val Lys
                405                 410                 415

Arg Gln Glu Val Ile Ser Glu Leu Leu Val Thr Glu Ala Ala His Val
            420                 425                 430

Arg Met Leu Arg Val Leu His Asp Leu Phe Phe Gln Pro Met Ala Glu
        435                 440                 445

Cys Leu Phe Phe Pro Leu Glu Glu Leu Gln Asn Ile Phe Pro Ser Leu
    450                 455                 460

Asp Glu Leu Ile Glu Val His Ser Leu Phe Leu Asp Arg Leu Met Lys
465                 470                 475                 480

Arg Arg Gln Glu Ser Gly Tyr Leu Ile Glu Glu Ile Gly Asp Val Leu
                485                 490                 495

Leu Ala Arg Phe Asp Gly Ala Glu Gly Ser Trp Phe Gln Lys Ile Ser
            500                 505                 510

Ser Arg Phe Cys Ser Arg Gln Ser Phe Ala Leu Glu Gln Leu Lys Ala
        515                 520                 525

Lys Gln Arg Lys Asp Pro Arg Phe Cys Ala Phe Val Gln Glu Ala Glu
    530                 535                 540

Ser Arg Pro Arg Cys Arg Arg Leu Gln Leu Lys Asp Met Ile Pro Thr
545                 550                 555                 560

Glu Met Gln Arg Leu Thr Lys Tyr Pro Leu Leu Leu Gln Ser Ile Gly
                565                 570                 575

Gln Asn Thr Glu Glu Pro Thr Glu Arg Glu Lys Val Glu Leu Ala Ala
            580                 585                 590

Glu Cys Cys Arg Glu Ile Leu His His Val Asn Gln Ala Val Arg Asp
        595                 600                 605

Met Glu Asp Leu Leu Arg Leu Lys Asp Tyr Gln Arg Arg Leu Asp Leu
    610                 615                 620

Ser His Leu Arg Gln Ser Ser Asp Pro Met Leu Ser Glu Phe Lys Asn
625                 630                 635                 640
```

Leu Asp Ile Thr Lys Lys Leu Val His Glu Gly Pro Leu Thr Trp
                645                 650                 655

Arg Val Thr Lys Asp Lys Ala Val Glu Val His Val Leu Leu Asp
            660                 665                 670

Asp Leu Leu Leu Leu Gln Arg Gln Asp Glu Arg Leu Leu Leu Lys
        675                 680                 685

Ser His Ser Arg Thr Leu Thr Pro Thr Pro Asp Gly Lys Thr Met Leu
690                 695                 700

Arg Pro Val Leu Arg Leu Thr Ser Ala Met Thr Arg Glu Val Ala Thr
705                 710                 715                 720

Asp His Lys Ala Phe Tyr Val Leu Phe Thr Trp Asp Gln Glu Ala Gln
                725                 730                 735

Ile Tyr Glu Leu Val Ala Gln Thr Val Ser Glu Arg Lys Asn Trp Cys
            740                 745                 750

Ala Leu Ile Thr Glu Thr Ala Gly Ser Leu Lys Val Pro Ala Pro Ala
        755                 760                 765

Ser Arg Pro Lys Pro Arg Pro Ser Pro Ser Ser Thr Arg Glu Pro Leu
770                 775                 780

Leu Ser Ser Ser Glu Asn Gly Asn Gly Gly Arg Glu Thr Ser Pro Ala
785                 790                 795                 800

Asp Ala Arg Thr Glu Arg Ile Leu Ser Asp Leu Leu Pro Phe Cys Arg
                805                 810                 815

Pro Gly Pro Glu Gly Gln Leu Ala Ala Thr Ala Leu Arg Lys Val Leu
            820                 825                 830

Ser Leu Lys Gln Leu Leu Phe Pro Ala Glu Glu Asp Asn Gly Ala Gly
        835                 840                 845

Pro Pro Arg Asp Gly Asp Gly Val Pro Gly Gly Pro Leu Ser Pro
850                 855                 860

Ala Arg Thr Gln Glu Ile Gln Glu Asn Leu Leu Ser Leu Glu Glu Thr
865                 870                 875                 880

Met Lys Gln Leu Glu Glu Leu Glu Glu Phe Cys Arg Leu Arg Pro
                885                 890                 895

Leu Leu Ser Gln Leu Gly Gly Asn Ser Val Pro Gln Pro Gly Cys Thr
            900                 905                 910

<210> SEQ ID NO 19
<211> LENGTH: 920
<212> TYPE: PRT
<213> ORGANISM: Mus musculus

<400> SEQUENCE: 19

Met Gly Glu Val Ala Gly Gly Ala Ala Pro Gly Pro Arg Ser Gly
1               5                   10                  15

Leu Val Ser Ile Ile Gly Ala Glu Asp Glu Phe Glu Asn Glu
            20                  25                  30

Leu Glu Ala Asn Ser Glu Asp Gln Asn Ser Gln Phe Gln Ser Leu Glu
        35                  40                  45

Gln Val Lys Arg Arg Pro Ala His Leu Met Ala Leu Leu Gln His Val
    50                  55                  60

Ala Leu Gln Phe Glu Pro Gly Pro Leu Leu Cys Cys Leu His Ala Asp
65                  70                  75                  80

Met Leu Ser Ser Leu Gly Pro Lys Glu Ala Lys Lys Ala Phe Leu Asp
                85                  90                  95

Phe Tyr His Ser Phe Leu Glu Lys Thr Ala Val Leu Arg Val Pro Val
            100                 105                 110

-continued

```
Pro Pro Ser Val Ala Phe Glu Leu Asp Arg Thr Arg Pro Asp Leu Ile
        115                 120                 125

Ser Glu Asp Val Gln Arg Arg Phe Ile Gln Glu Val Val Gln Ser Gln
    130                 135                 140

Gln Ala Ala Val Ser Arg Gln Leu Glu Asp Phe Arg Ser Lys Arg Leu
145                 150                 155                 160

Met Gly Met Thr Pro Trp Glu Gln Glu Leu Ser Leu Leu Glu Pro Trp
                165                 170                 175

Ile Gly Lys Asp Arg Gly Asn Tyr Glu Ala Arg Glu Arg His Val Ala
                180                 185                 190

Glu Arg Leu Leu Ser His Leu Glu Glu Thr Gln His Thr Ile Ser Thr
            195                 200                 205

Asp Glu Glu Lys Ser Ala Ala Val Val Thr Ala Ile Ser Leu Tyr Met
    210                 215                 220

Arg His Leu Gly Val Arg Thr Lys Ser Gly Asp Lys Lys Ser Gly Arg
225                 230                 235                 240

Asn Phe Phe Arg Lys Lys Val Met Gly Asn Arg Arg Ser Asp Glu Pro
                245                 250                 255

Pro Lys Thr Lys Lys Gly Leu Ser Ser Ile Leu Asp Pro Ala Arg Trp
                260                 265                 270

Asn Arg Gly Glu Pro Ser Ala Pro Asp Cys Arg His Leu Lys Val Glu
            275                 280                 285

Ala Asp Ala Glu Lys Pro Gly Pro Ala Asp Arg Lys Gly Gly Leu Gly
    290                 295                 300

Met Ser Ser Arg Asp Arg Thr Val Gly Thr Pro Gly Gln Asp Asn Pro
305                 310                 315                 320

Gly Val Ser Leu His Pro Leu Ser Thr Asp Ser Val Asp Ser Arg Glu
                325                 330                 335

Pro Gly Val Asp Thr Pro Gln Glu Pro Gly Asp Thr Pro Pro Gln Gly
            340                 345                 350

Pro Thr Ser Leu Glu Pro Leu Ala Pro Pro Glu Ser Thr Glu Asp Asn
    355                 360                 365

Gly Glu Thr Glu Ser Pro Glu Pro Gly Asp Asp Gly Glu Pro Gly Arg
    370                 375                 380

Ser Gly Leu Glu Leu Glu Pro Glu Pro Pro Gly Trp Arg Glu Leu
385                 390                 395                 400

Val Pro Pro Asp Thr Leu Leu Ser Leu Pro Lys Ser Gln Val Lys Arg
                405                 410                 415

Gln Glu Val Ile Ser Glu Leu Leu Val Thr Glu Ala Ala His Val Arg
                420                 425                 430

Met Leu Arg Val Leu His Asp Leu Phe Tyr Gln Pro Met Ala Asp Gly
            435                 440                 445

Gly Phe Phe Pro Leu Asp Glu Leu Gln Asn Ile Phe Pro Ser Leu Asp
    450                 455                 460

Glu Leu Ile Glu Val His Ser Leu Phe Leu Asp Arg Leu Met Lys Arg
465                 470                 475                 480

Arg Gln Glu Ser Gly Tyr Leu Ile Glu Ile Gly Asp Val Leu Leu
                485                 490                 495

Ala Arg Phe Asp Gly Ala Glu Gly Ser Trp Phe Gln Lys Ile Ser Ser
            500                 505                 510
```

-continued

```
Arg Phe Cys Ser Arg Gln Ser Phe Ala Leu Glu Gln Leu Lys Ala Lys
            515                 520                 525
Gln Arg Lys Glu Pro Arg Phe Cys Ala Phe Val Gln Glu Ala Glu Ser
530                 535                 540
Arg Pro Arg Cys Arg Arg Leu Gln Leu Lys Asp Met Ile Pro Thr Glu
545                 550                 555                 560
Met Gln Arg Leu Thr Lys Tyr Pro Leu Leu Leu Gln Ser Ile Gly Gln
                565                 570                 575
Asn Thr Glu Glu Ser Thr Glu Arg Gly Lys Val Glu Leu Ala Ala Glu
            580                 585                 590
Cys Cys Arg Glu Ile Leu His His Val Asn Gln Ala Val Arg Asp Met
        595                 600                 605
Glu Asp Leu Leu Arg Leu Lys Asp Tyr Gln Arg Arg Leu Asp Leu Thr
610                 615                 620
His Leu Arg Gln Ser Ser Asp Pro Met Leu Ser Glu Phe Lys Asn Leu
625                 630                 635                 640
Asp Ile Thr Lys Lys Lys Leu Val His Glu Gly Pro Leu Thr Trp Arg
                645                 650                 655
Val Thr Lys Asp Lys Ala Ile Glu Val His Val Leu Leu Leu Asp Asp
            660                 665                 670
Leu Leu Leu Leu Leu Gln Arg Gln Asp Glu Arg Leu Leu Leu Lys Ser
        675                 680                 685
His Ser Arg Thr Leu Thr Pro Thr Pro Asp Gly Lys Thr Met Leu Arg
690                 695                 700
Pro Val Leu Arg Leu Thr Ser Ala Met Thr Arg Glu Val Ala Thr Asp
705                 710                 715                 720
His Lys Ala Phe Tyr Val Ile Phe Thr Trp Asp Gln Glu Ala Gln Ile
                725                 730                 735
Tyr Glu Leu Val Ala Gln Thr Ser Ser Glu Arg Lys Asn Trp Cys Asn
            740                 745                 750
Leu Ile Thr Glu Thr Ala Gly Ser Leu Lys Val Pro Ala Pro Ala Ser
        755                 760                 765
Arg Leu Lys Pro Arg Pro Ser Pro Ser Ser Ile Arg Glu Pro Leu Leu
770                 775                 780
Ser Ser Ser Glu Asn Gly Thr Gly Gly Ala Glu Met Ala Pro Ala Asp
785                 790                 795                 800
Ala Arg Thr Glu Arg Leu Leu Asn Asp Leu Leu Pro Phe Cys Arg Pro
                805                 810                 815
Gly Pro Glu Gly Gln Leu Ala Ala Thr Ala Leu Gln Lys Val Leu Ser
            820                 825                 830
Leu Lys Gln Ile Leu Leu Ser Thr Glu Glu Asp Ser Gly Ala Gly Pro
        835                 840                 845
Pro Arg Asp Gly Asp Gly Val Pro Gly Gly Arg Ala Pro Gly Pro Val
850                 855                 860
His Thr Gln Glu Ile Glu Glu Asn Leu Leu Ser Leu Glu Val Ala Ile
865                 870                 875                 880
Arg Gln Leu Glu Glu Leu Glu Glu Phe Cys Arg Leu Arg Pro Leu
                885                 890                 895
Leu Ser Gln Leu Gly Gly Thr Leu Ser Pro Asn Leu Ala Ala Pro Glu
            900                 905                 910
Arg Ser Ala Gln Thr Gly Leu Ser
        915                 920
```

<210> SEQ ID NO 20
<211> LENGTH: 986
<212> TYPE: PRT
<213> ORGANISM: Homo sapiens

<400> SEQUENCE: 20

```
Met Ser Arg Ile Glu Ser Leu Thr Arg Ala Arg Ile Asp Arg Ser Arg
1               5                   10                  15

Glu Leu Ala Ser Lys Thr Arg Glu Lys Glu Lys Met Lys Glu Ala Lys
            20                  25                  30

Asp Ala Arg Tyr Thr Asn Gly His Leu Phe Thr Thr Ile Ser Val Ser
        35                  40                  45

Gly Met Thr Met Cys Tyr Ala Cys Asn Lys Ser Ile Thr Ala Lys Glu
    50                  55                  60

Ala Leu Ile Cys Pro Thr Cys Asn Val Thr Ile His Asn Arg Cys Lys
65                  70                  75                  80

Asp Thr Leu Ala Asn Cys Thr Lys Val Lys Gln Lys Gln Gln Lys Ala
            85                  90                  95

Ala Leu Leu Lys Asn Asn Thr Ala Leu Gln Ser Val Ser Leu Arg Ser
            100                 105                 110

Lys Thr Thr Ile Arg Glu Arg Pro Ser Ser Ala Ile Tyr Pro Ser Asp
        115                 120                 125

Ser Phe Arg Gln Ser Leu Leu Gly Ser Arg Gly Arg Ser Ser Leu
    130                 135                 140

Ser Leu Ala Lys Ser Val Ser Thr Thr Asn Ile Ala Gly His Phe Asn
145                 150                 155                 160

Asp Glu Ser Pro Leu Gly Leu Arg Arg Ile Leu Ser Gln Ser Thr Asp
            165                 170                 175

Ser Leu Asn Met Arg Asn Arg Thr Leu Ser Val Glu Ser Leu Ile Asp
            180                 185                 190

Glu Ala Glu Val Ile Tyr Ser Glu Leu Met Ser Asp Phe Glu Met Asp
        195                 200                 205

Glu Lys Asp Phe Ala Ala Asp Ser Trp Ser Leu Ala Val Asp Ser Ser
    210                 215                 220

Phe Leu Gln Gln His Lys Lys Glu Val Met Lys Gln Gln Asp Val Ile
225                 230                 235                 240

Tyr Glu Leu Ile Gln Thr Glu Leu His His Val Arg Thr Leu Lys Ile
            245                 250                 255

Met Thr Arg Leu Phe Arg Thr Gly Met Leu Glu Glu Leu His Leu Glu
            260                 265                 270

Pro Gly Val Val Gln Gly Leu Phe Pro Cys Val Asp Glu Leu Ser Asp
        275                 280                 285

Ile His Thr Arg Phe Leu Ser Gln Leu Leu Glu Arg Arg Gln Ala
    290                 295                 300

Leu Cys Pro Gly Ser Thr Arg Asn Phe Val Ile His Arg Leu Gly Asp
305                 310                 315                 320

Leu Leu Ile Ser Gln Phe Ser Gly Pro Ser Ala Glu Gln Met Cys Lys
            325                 330                 335

Thr Tyr Ser Glu Phe Cys Ser Arg His Ser Lys Ala Leu Lys Leu Tyr
            340                 345                 350

Lys Glu Leu Tyr Ala Arg Asp Lys Arg Phe Gln Gln Phe Ile Arg Lys
        355                 360                 365

Val Thr Arg Pro Ala Val Leu Lys Arg His Gly Val Gln Glu Cys Ile
    370                 375                 380
```

```
Leu Leu Val Thr Gln Arg Ile Thr Lys Tyr Pro Leu Leu Ile Ser Arg
385                 390                 395                 400

Ile Leu Gln His Ser His Gly Ile Glu Glu Arg Gln Asp Leu Thr
            405                 410                 415

Thr Ala Leu Gly Leu Val Lys Glu Leu Leu Ser Asn Val Asp Glu Gly
            420                 425                 430

Ile Tyr Gln Leu Glu Lys Gly Ala Arg Leu Gln Glu Ile Tyr Asn Arg
            435                 440                 445

Met Asp Pro Arg Ala Gln Thr Pro Val Pro Gly Lys Gly Pro Phe Gly
            450                 455                 460

Arg Glu Glu Leu Arg Arg Lys Leu Ile His Asp Gly Cys Leu Leu
465                 470                 475                 480

Trp Lys Thr Ala Thr Gly Arg Phe Lys Asp Val Leu Val Leu Leu Met
            485                 490                 495

Thr Asp Val Leu Val Phe Leu Gln Glu Lys Asp Gln Lys Tyr Ile Phe
            500                 505                 510

Pro Thr Leu Asp Lys Pro Ser Val Val Ser Leu Gln Asn Leu Ile Val
            515                 520                 525

Arg Asp Ile Ala Asn Gln Glu Lys Gly Met Phe Leu Ile Ser Ala Ala
            530                 535                 540

Pro Pro Glu Met Tyr Glu Val His Thr Ala Ser Arg Asp Asp Arg Ser
545                 550                 555                 560

Thr Trp Ile Arg Val Ile Gln Gln Ser Val Arg Thr Cys Pro Ser Arg
            565                 570                 575

Glu Asp Phe Pro Leu Ile Glu Thr Glu Asp Glu Ala Tyr Leu Arg Arg
            580                 585                 590

Ile Lys Met Glu Leu Gln Gln Lys Asp Arg Ala Leu Val Glu Leu Leu
            595                 600                 605

Arg Glu Lys Val Gly Leu Phe Ala Glu Met Thr His Phe Gln Ala Glu
610                 615                 620

Glu Asp Gly Gly Ser Gly Met Ala Leu Pro Thr Leu Pro Arg Gly Leu
625                 630                 635                 640

Phe Arg Ser Glu Ser Leu Glu Ser Pro Arg Gly Glu Arg Leu Leu Gln
            645                 650                 655

Asp Ala Ile Arg Glu Val Glu Gly Leu Lys Asp Leu Leu Val Gly Pro
            660                 665                 670

Gly Val Glu Leu Leu Leu Thr Pro Arg Glu Pro Ala Leu Pro Leu Glu
            675                 680                 685

Pro Asp Ser Gly Gly Asn Thr Ser Pro Gly Val Thr Ala Asn Gly Glu
690                 695                 700

Ala Arg Thr Phe Asn Gly Ser Ile Glu Leu Cys Arg Ala Asp Ser Asp
705                 710                 715                 720

Ser Ser Gln Arg Asp Arg Asn Gly Asn Gln Leu Arg Ser Pro Gln Glu
            725                 730                 735

Glu Ala Leu Gln Arg Leu Val Asn Leu Tyr Gly Leu Leu His Gly Leu
            740                 745                 750

Gln Ala Ala Val Ala Gln Asp Thr Leu Met Glu Ala Arg Phe Pro
            755                 760                 765

Glu Gly Pro Glu Arg Arg Glu Lys Leu Cys Arg Ala Asn Ser Arg Asp
            770                 775                 780

Gly Glu Ala Gly Arg Ala Gly Ala Ala Pro Val Ala Pro Glu Lys Gln
785                 790                 795                 800
```

```
Ala Thr Glu Leu Ala Leu Leu Gln Arg Gln His Ala Leu Leu Gln Glu
                805                 810                 815

Glu Leu Arg Arg Cys Arg Arg Leu Gly Glu Glu Arg Ala Thr Glu Ala
            820                 825                 830

Gly Ser Leu Glu Ala Arg Leu Arg Glu Ser Glu Gln Ala Arg Ala Leu
        835                 840                 845

Leu Glu Arg Glu Ala Glu Ala Arg Arg Gln Leu Ala Ala Leu Gly
    850                 855                 860

Gln Thr Glu Pro Leu Pro Ala Glu Ala Pro Trp Ala Arg Arg Pro Val
865                 870                 875                 880

Asp Pro Arg Arg Ser Leu Pro Ala Gly Asp Ala Leu Tyr Leu Ser
                885                 890                 895

Phe Asn Pro Pro Gln Pro Ser Arg Gly Thr Asp Arg Leu Asp Leu Pro
                900                 905                 910

Val Thr Thr Arg Ser Val His Arg Asn Phe Glu Asp Arg Glu Arg Gln
            915                 920                 925

Glu Leu Gly Ser Pro Glu Arg Leu Gln Asp Ser Ser Asp Pro Asp
        930                 935                 940

Thr Gly Ser Glu Glu Glu Gly Ser Ser Arg Leu Ser Pro Pro His Ser
945                 950                 955                 960

Pro Arg Asp Phe Thr Arg Met Gln Asp Ile Pro Glu Thr Glu Ser
                965                 970                 975

Arg Asp Gly Glu Ala Val Ala Ser Glu Ser
            980                 985

<210> SEQ ID NO 21
<211> LENGTH: 985
<212> TYPE: PRT
<213> ORGANISM: Mus musculus

<400> SEQUENCE: 21

Met Ser Arg Ile Glu Ser Leu Thr Arg Ala Arg Ile Asp Arg Ser Lys
1               5                   10                  15

Glu Gln Ala Thr Lys Thr Arg Glu Lys Glu Met Lys Glu Ala Lys
            20                  25                  30

Asp Ala Arg Tyr Thr Asn Gly His Leu Phe Thr Thr Ile Ser Val Ser
        35                  40                  45

Gly Met Thr Met Cys Tyr Ala Cys Asn Lys Ser Ile Thr Ala Lys Glu
    50                  55                  60

Ala Leu Ile Cys Pro Thr Cys Asn Val Thr Ile His Asn Arg Cys Lys
65                  70                  75                  80

Asp Thr Leu Ala Asn Cys Thr Lys Val Lys Gln Lys Gln Lys Ala
                85                  90                  95

Ala Leu Leu Arg Asn Asn Thr Ala Leu Gln Ser Val Ser Leu Arg Ser
            100                 105                 110

Lys Thr Thr Thr Arg Glu Arg Pro Thr Ser Ala Ile Tyr Pro Ser Asp
        115                 120                 125

Ser Phe Arg Gln Ser Leu Leu Gly Ser Arg Arg Gly Leu Ser Ser Leu
130                 135                 140

Ser Leu Ala Lys Ser Val Ser Thr Thr Asn Ile Ala Gly His Phe Asn
145                 150                 155                 160

Asp Glu Ser Pro Leu Gly Leu Arg Gln Ile Leu Ser Gln Ser Thr Asp
                165                 170                 175

Ser Leu Asn Met Arg Asn Arg Thr Leu Ser Val Glu Ser Leu Ile Asp
            180                 185                 190
```

```
Glu Gly Val Glu Val Phe Tyr Asn Glu Leu Met Ser Asp Phe Glu Met
            195                 200                 205
Asp Glu Lys Asp Phe Glu Ala Asp Ser Trp Ser Leu Ala Val Asp Ser
210                 215                 220
Ser Phe Leu Gln Gln His Lys Lys Glu Val Met Lys Lys Gln Asp Val
225                 230                 235                 240
Ile Tyr Glu Leu Ile Gln Thr Glu Leu His His Val Arg Thr Leu Lys
                245                 250                 255
Ile Met Thr Arg Leu Phe Arg Thr Gly Met Leu Glu Glu Leu Gln Met
            260                 265                 270
Glu Pro Glu Val Val Gln Gly Leu Phe Pro Cys Val Asp Glu Leu Ser
            275                 280                 285
Asp Ile His Thr Arg Phe Leu Asn Gln Leu Leu Glu Arg Arg Arg Gln
290                 295                 300
Ala Leu Cys Pro Gly Ser Thr Arg Asn Phe Val Ile His Arg Leu Gly
305                 310                 315                 320
Asp Leu Leu Ile Ser Gln Phe Ser Gly Ser Asn Ala Glu Gln Met Arg
                325                 330                 335
Lys Thr Tyr Ser Glu Phe Cys Ser Arg His Thr Lys Ala Leu Lys Leu
            340                 345                 350
Tyr Lys Glu Leu Tyr Ala Arg Asp Lys Arg Phe Gln Gln Phe Ile Arg
            355                 360                 365
Lys Met Thr Arg Ser Ala Val Leu Lys Arg His Gly Val Gln Glu Cys
            370                 375                 380
Ile Leu Leu Val Thr Gln Arg Ile Thr Lys Tyr Pro Val Leu Ile Asn
385                 390                 395                 400
Arg Ile Leu Gln Asn Ser His Gly Val Glu Glu Tyr Gln Asp Leu
                405                 410                 415
Ala Ser Ala Leu Gly Leu Val Lys Glu Leu Leu Ser Asn Val Asp Gln
                420                 425                 430
Asp Val His Glu Leu Glu Lys Glu Ala Arg Leu Gln Glu Ile Tyr Asn
            435                 440                 445
Arg Met Asp Pro Arg Ala Gln Thr Pro Val Pro Gly Lys Gly Pro Phe
            450                 455                 460
Gly Arg Asp Glu Leu Leu Arg Arg Lys Leu Ile His Glu Gly Cys Leu
465                 470                 475                 480
Leu Trp Lys Thr Ala Thr Gly Arg Phe Lys Asp Val Leu Leu Leu Leu
                485                 490                 495
Met Thr Asp Val Leu Val Phe Leu Gln Glu Lys Asp Gln Lys Tyr Ile
            500                 505                 510
Phe Thr Ser Leu Asp Lys Pro Ser Val Val Ser Leu Gln Asn Leu Ile
            515                 520                 525
Val Arg Asp Ile Ala Asn Gln Ala Lys Gly Met Phe Leu Ile Ser Ser
530                 535                 540
Gly Pro Pro Glu Met Tyr Glu Val His Ala Ala Ser Arg Asp Asp Arg
545                 550                 555                 560
Thr Thr Trp Ile Arg Val Ile Gln Gln Ser Val Arg Leu Cys Pro Ser
                565                 570                 575
Arg Glu Asp Phe Pro Leu Ile Glu Thr Asp Lys Ala Tyr Leu Arg
            580                 585                 590
Arg Ile Lys Thr Lys Leu Gln Gln Lys Asn Gln Ala Leu Val Glu Leu
            595                 600                 605
```

```
Leu Gln Lys Asn Val Glu Leu Phe Ala Glu Met Val His Phe Gln Ala
610                 615                 620
Leu Lys Ala Gly Phe Val Gly Met Pro Pro Ala Leu Pro Arg Gly
625                 630                 635                 640
Leu Phe Arg Leu Glu Ser Phe Glu Ser Leu Arg Gly Glu Arg Leu Leu
            645                 650                 655
Lys Asp Ala Leu Arg Glu Val Glu Gly Leu Lys Asp Leu Leu Leu Gly
                660                 665                 670
Pro Cys Val Asp Leu Pro Met Thr Ser Arg Glu Pro Ala Leu Pro Leu
            675                 680                 685
Asp Ser Asp Ser Gly Ser Cys Pro Gly Val Thr Ala Asn Gly Glu Ala
690                 695                 700
Arg Thr Phe Asn Gly Ser Ile Glu Leu Cys Arg Ala Asp Ser Asp Ser
705                 710                 715                 720
Ser Gln Lys Asp Arg Asn Gly Asn Gln Leu Arg Ser Pro Gln Glu Glu
                725                 730                 735
Val Leu Gln Pro Leu Ile Asn Leu Tyr Gly Leu Leu His Gly Leu Gln
                740                 745                 750
Ala Val Val Val Gln Gln Glu Arg Leu Met Glu Ala Leu Phe Pro Glu
            755                 760                 765
Gly Pro Glu Arg Trp Glu Lys Leu Ser Arg Ala Asn Ser Arg Asp Gly
770                 775                 780
Glu Ala Gly Arg Ala Ala Val Ala Ser Val Thr Pro Glu Lys Gln Ala
785                 790                 795                 800
Thr Glu Leu Ala Leu Leu Gln Arg Gln His Thr Leu Leu Gln Glu Glu
                805                 810                 815
Leu Arg Arg Cys Gln Arg Leu Gly Glu Arg Ala Thr Glu Ala Gly
            820                 825                 830
Ser Leu Glu Ala Arg Leu Arg Glu Ser Glu Gln Ala Arg Ala Leu Leu
                835                 840                 845
Glu Arg Glu Ala Glu Glu Ile Arg Arg Gln Leu Ala Ala Leu Gly Gln
850                 855                 860
Asn Glu Pro Leu Pro Ala Glu Ala Pro Trp Ala Arg Arg Pro Leu Asp
865                 870                 875                 880
Pro Arg Arg Arg Ser Leu Pro Ala Gly Asp Ala Leu Tyr Leu Ser Phe
                885                 890                 895
Asn Pro Pro Gln Pro Ser Arg Gly His Asp Arg Leu Asp Leu Pro Val
                900                 905                 910
Thr Val Arg Ser Leu His Arg Pro Phe Asp Asp Arg Glu Ala Gln Glu
                915                 920                 925
Leu Gly Ser Pro Glu Asp Arg Leu Gln Asp Ser Ser Asp Pro Asp Thr
930                 935                 940
Gly Ser Glu Glu Glu Val Ser Ser Arg Leu Ser Pro Pro His Ser Pro
945                 950                 955                 960
Arg Asp Phe Thr Arg Met Gln Asp Ile Pro Glu Glu Thr Glu Ser Arg
                965                 970                 975
Asp Gly Glu Pro Thr Ala Ser Glu Ser
                980                 985

<210> SEQ ID NO 22
<211> LENGTH: 776
<212> TYPE: PRT
<213> ORGANISM: Homo sapiens
```

<400> SEQUENCE: 22

```
Met Asn Pro Glu Glu Gln Ile Val Thr Trp Leu Ile Ser Leu Gly Val
1               5                  10                  15

Leu Glu Ser Pro Lys Lys Thr Ile Cys Asp Pro Glu Glu Phe Leu Lys
            20                  25                  30

Ser Ser Leu Lys Asn Gly Val Val Leu Cys Lys Leu Ile Asn Arg Leu
        35                  40                  45

Met Pro Gly Ser Val Glu Lys Phe Cys Leu Asp Pro Gln Thr Glu Ala
    50                  55                  60

Asp Cys Ile Asn Asn Ile Asn Asp Phe Leu Lys Gly Cys Ala Thr Leu
65                  70                  75                  80

Gln Val Glu Ile Phe Asp Pro Asp Asp Leu Tyr Ser Gly Val Asn Phe
                85                  90                  95

Ser Lys Val Leu Ser Thr Leu Leu Ala Val Asn Lys Ala Thr Glu Asp
            100                 105                 110

Gln Leu Ser Glu Arg Pro Cys Gly Arg Ser Ser Ser Leu Ser Ala Ala
        115                 120                 125

Asn Thr Ser Gln Thr Asn Pro Gln Gly Ala Val Ser Ser Thr Val Ser
130                 135                 140

Gly Leu Gln Arg Gln Ser Lys Thr Val Glu Met Thr Glu Asn Gly Ser
145                 150                 155                 160

His Gln Leu Ile Val Lys Ala Arg Phe Asn Phe Lys Gln Thr Asn Glu
                165                 170                 175

Asp Glu Leu Ser Val Cys Lys Gly Asp Ile Ile Tyr Val Thr Arg Val
            180                 185                 190

Glu Glu Gly Gly Trp Trp Glu Gly Thr Leu Asn Gly Arg Thr Gly Trp
        195                 200                 205

Phe Pro Ser Asn Tyr Val Arg Glu Ile Lys Ser Ser Glu Arg Pro Leu
210                 215                 220

Ser Pro Lys Ala Val Lys Gly Phe Glu Thr Ala Pro Leu Thr Lys Asn
225                 230                 235                 240

Tyr Tyr Thr Val Val Leu Gln Asn Ile Leu Asp Thr Glu Lys Glu Tyr
                245                 250                 255

Ala Lys Glu Leu Gln Ser Leu Leu Val Thr Tyr Leu Arg Pro Leu Gln
            260                 265                 270

Ser Asn Asn Asn Leu Ser Thr Val Glu Val Thr Ser Leu Leu Gly Asn
        275                 280                 285

Phe Glu Glu Val Cys Thr Phe Gln Gln Thr Leu Cys Gln Ala Leu Glu
290                 295                 300

Glu Cys Ser Lys Phe Pro Glu Asn Gln His Lys Val Gly Gly Cys Leu
305                 310                 315                 320

Leu Ser Leu Met Pro His Phe Lys Ser Met Tyr Leu Ala Tyr Cys Ala
                325                 330                 335

Asn His Pro Ser Ala Val Asn Val Leu Thr Gln His Ser Asp Glu Leu
            340                 345                 350

Glu Gln Phe Met Glu Asn Gln Gly Ala Ser Ser Pro Gly Ile Leu Ile
        355                 360                 365

Leu Thr Thr Asn Leu Ser Lys Pro Phe Met Arg Leu Glu Lys Tyr Val
370                 375                 380

Thr Leu Leu Gln Glu Leu Glu Arg His Met Glu Asp Thr His Pro Asp
385                 390                 395                 400
```

```
His Gln Asp Ile Leu Lys Ala Ile Val Ala Phe Lys Thr Leu Met Gly
                405                 410                 415

Gln Cys Gln Asp Leu Arg Lys Arg Lys Gln Leu Glu Leu Gln Ile Leu
            420                 425                 430

Ser Glu Pro Ile Gln Ala Trp Glu Gly Glu Asp Ile Lys Asn Leu Gly
        435                 440                 445

Asn Val Ile Phe Met Ser Gln Val Met Val Gln Tyr Gly Ala Cys Glu
    450                 455                 460

Glu Lys Glu Glu Arg Tyr Leu Met Leu Phe Ser Asn Val Leu Ile Met
465                 470                 475                 480

Leu Ser Ala Ser Pro Arg Met Ser Gly Phe Ile Tyr Gln Gly Lys Ile
                485                 490                 495

Pro Ile Ala Gly Thr Val Val Thr Arg Leu Asp Glu Ile Glu Gly Asn
            500                 505                 510

Asp Cys Thr Phe Glu Ile Thr Gly Asn Thr Val Glu Arg Ile Val Val
        515                 520                 525

His Cys Asn Asn Asn Gln Asp Phe Gln Glu Trp Leu Glu Gln Leu Asn
    530                 535                 540

Arg Leu Ile Arg Gly Pro Ala Ser Cys Ser Ser Leu Ser Lys Thr Ser
545                 550                 555                 560

Ser Ser Ser Cys Ser Ala His Ser Ser Phe Ser Ser Thr Gly Gln Pro
                565                 570                 575

Arg Gly Pro Leu Glu Pro Pro Gln Ile Ile Lys Pro Trp Ser Leu Ser
            580                 585                 590

Cys Leu Arg Pro Ala Pro Pro Leu Arg Pro Ser Ala Ala Leu Gly Tyr
        595                 600                 605

Lys Glu Arg Met Ser Tyr Ile Leu Lys Glu Ser Ser Lys Ser Pro Lys
    610                 615                 620

Thr Met Lys Lys Phe Leu His Lys Arg Lys Thr Glu Arg Lys Pro Ser
625                 630                 635                 640

Glu Glu Glu Tyr Val Ile Arg Lys Ser Thr Ala Ala Leu Glu Glu Asp
                645                 650                 655

Ala Gln Ile Leu Lys Val Ile Glu Ala Tyr Cys Thr Ser Ala Asn Phe
            660                 665                 670

Gln Gln Gly His Gly Ser Ser Thr Arg Lys Asp Ser Ile Pro Gln Val
        675                 680                 685

Leu Leu Pro Glu Glu Glu Lys Leu Ile Ile Glu Glu Thr Arg Ser Asn
    690                 695                 700

Gly Gln Thr Ile Met Glu Glu Lys Ser Leu Val Asp Thr Val Tyr Ala
705                 710                 715                 720

Leu Lys Asp Glu Val Arg Glu Leu Lys Gln Glu Asn Lys Arg Met Lys
                725                 730                 735

Gln Cys Leu Glu Glu Glu Leu Lys Ser Arg Arg Asp Leu Glu Lys Leu
            740                 745                 750

Val Arg Arg Leu Leu Lys Gln Thr Asp Glu Cys Ile Arg Gly Glu Ser
        755                 760                 765

Ser Ser Lys Thr Ser Ile Leu Pro
    770                 775

<210> SEQ ID NO 23
<211> LENGTH: 771
<212> TYPE: PRT
<213> ORGANISM: Mus musculus
```

```
<400> SEQUENCE: 23

Met Asn Pro Glu Glu Arg Leu Val Thr Trp Leu Ile Ser Leu Gly Val
1               5                   10                  15

Leu Glu Ser Pro Lys Lys Thr Val Cys Asp Pro Glu Glu Phe Leu Lys
            20                  25                  30

Ser Ser Leu Lys Asn Gly Val Val Leu Cys Lys Leu Ile Asn Arg Leu
        35                  40                  45

Leu Pro Gly Ser Val Glu Lys Tyr Cys Leu Glu Pro Gln Thr Glu Ala
    50                  55                  60

Asp Cys Ile Asp Asn Ile Asn Asp Phe Leu Lys Gly Cys Ala Thr Leu
65                  70                  75                  80

Gln Val Glu Val Phe Glu Pro Asp Asp Leu Tyr Ser Gly Ala Asn Phe
                85                  90                  95

Ser Lys Val Leu Asn Thr Leu Leu Ala Val Asn Lys Ala Thr Glu Asp
            100                 105                 110

Gln Leu Ser Glu Arg Pro Cys Gly Arg Ser Ser Ser Leu Ser Ala Ala
        115                 120                 125

Thr Ser Ser Gln Thr Asn Pro Gln Val Ala Val Pro Ser Thr Ala Pro
130                 135                 140

Glu Gln His Ser Glu Glu Lys Ala Glu Met Thr Glu Asn Gly Ser His
145                 150                 155                 160

Gln Leu Ile Val Lys Ala Arg Phe Asn Phe Lys Gln Thr Asn Glu Asp
                165                 170                 175

Glu Leu Ser Val Cys Lys Gly Asp Ile Ile Tyr Val Thr Arg Val Glu
            180                 185                 190

Glu Gly Gly Trp Trp Glu Gly Thr Leu Asn Gly Arg Thr Gly Trp Phe
        195                 200                 205

Pro Ser Asn Tyr Val Arg Glu Ile Lys Pro Ser Glu Arg Pro Leu Ser
    210                 215                 220

Pro Lys Ala Ile Lys Gly Phe Asp Thr Ala Pro Leu Thr Lys Asn Tyr
225                 230                 235                 240

Tyr Thr Val Val Leu Gln Asn Ile Leu Asp Thr Glu Lys Glu Tyr Ala
                245                 250                 255

Lys Glu Leu Gln Ser Leu Leu Val Thr Tyr Leu Arg Pro Leu Gln Ser
            260                 265                 270

Asn Asn Asn Leu Ser Thr Val Glu Phe Thr Cys Leu Leu Gly Asn Phe
        275                 280                 285

Glu Glu Val Cys Thr Phe Gln Gln Thr Leu Cys Gln Ala Leu Glu Glu
    290                 295                 300

Cys Ser Lys Phe Pro Glu Asn Gln His Lys Val Gly Gly Cys Leu Leu
305                 310                 315                 320

Asn Leu Met Pro His Phe Lys Ser Met Tyr Leu Ala Tyr Cys Ala Asn
                325                 330                 335

His Pro Ser Ala Val Asn Val Leu Thr Gln His Ser Asp Asp Leu Glu
            340                 345                 350

Arg Phe Met Glu Asn Gln Gly Ala Ser Ser Pro Gly Ile Leu Ile Leu
        355                 360                 365

Thr Thr Ser Leu Ser Lys Pro Phe Met Arg Leu Glu Lys Tyr Val Thr
    370                 375                 380

Leu Leu Gln Glu Leu Glu Arg His Met Glu Asp Thr His Pro Asp His
385                 390                 395                 400
```

Gln Asp Ile Leu Lys Ala Ile Ala Phe Lys Thr Leu Met Gly Gln
            405                 410                 415

Cys Gln Asp Leu Arg Lys Arg Lys Gln Leu Glu Leu Gln Ile Leu Ser
        420                 425                 430

Glu Pro Ile Gln Ala Trp Glu Gly Asp Asp Ile Lys Thr Leu Gly Asn
        435                 440                 445

Val Ile Phe Met Ser Gln Val Met Gln His Gly Ala Cys Glu Glu
    450                 455                 460

Lys Glu Glu Arg Tyr Phe Leu Leu Phe Ser Val Leu Ile Met Leu
465                 470                 475                 480

Ser Ala Ser Pro Arg Met Ser Gly Phe Met Tyr Gln Gly Lys Ile Pro
        485                 490                 495

Ile Ala Gly Met Val Val Asn Arg Leu Asp Glu Ile Glu Gly Ser Asp
        500                 505                 510

Cys Met Phe Glu Ile Thr Gly Ser Thr Val Glu Arg Ile Val Val His
        515                 520                 525

Cys Asn Asn Asn Gln Asp Phe Gln Glu Trp Met Glu Gln Leu Asn Arg
        530                 535                 540

Leu Thr Lys Gly Pro Thr Ser Cys Gly Ser Leu Ser Lys Thr Ser Ser
545                 550                 555                 560

Ser Ser Cys Ser Thr His Ser Ser Phe Ser Ser Thr Gly Gln Pro Arg
                565                 570                 575

Gly Pro Leu Glu Pro Pro Gln Ile Ile Lys Pro Trp Ser Leu Ser Cys
        580                 585                 590

Leu Arg Pro Ala Pro Pro Leu Arg Pro Ser Ala Ala Leu Gly Tyr Lys
        595                 600                 605

Glu Arg Met Ser Tyr Ile Leu Lys Glu Ser Ser Lys Ser Pro Lys Thr
        610                 615                 620

Met Lys Lys Phe Leu His Lys Arg Lys Thr Glu Arg Lys Ala Ser Glu
625                 630                 635                 640

Glu Glu Tyr Val Ile Arg Lys Ser Thr Ala Ala Leu Glu Glu Asp Ala
                645                 650                 655

Gln Ile Leu Lys Val Ile Glu Ala Tyr Cys Thr Ser Ala Ser Phe Gln
        660                 665                 670

Gln Gly Thr Arg Lys Asp Ser Val Pro Gln Val Leu Leu Pro Glu Glu
        675                 680                 685

Glu Lys Leu Ile Ile Glu Glu Thr Arg Ser Asn Gly Gln Thr Ile Ile
        690                 695                 700

Glu Glu Lys Ser Leu Val Asp Thr Val Tyr Ala Leu Lys Asp Glu Val
705                 710                 715                 720

Lys Glu Leu Lys Gln Glu Asn Lys Lys Met Lys Gln Cys Leu Glu Glu
                725                 730                 735

Glu Leu Lys Ser Arg Lys Asp Leu Glu Lys Leu Val Arg Lys Leu Leu
        740                 745                 750

Lys Gln Thr Asp Glu Cys Ile Arg Ser Glu Ser Ser Lys Thr Ser
        755                 760                 765

Ile Leu Gln
    770

<210> SEQ ID NO 24
<211> LENGTH: 10
<212> TYPE: PRT
<213> ORGANISM: Homo sapiens

```
<400> SEQUENCE: 24

Leu Lys Glu Ile Ser Leu Ser Ala Val Arg
1               5                   10
```